(12) United States Patent
Kazuki et al.

(10) Patent No.: US 12,063,913 B2
(45) Date of Patent: Aug. 20, 2024

(54) HUMAN ANTIBODY-PRODUCING NON-HUMAN ANIMAL AND METHOD FOR PREPARING HUMAN ANTIBODIES USING SAME

(71) Applicants: NATIONAL UNIVERSITY CORPORATION TOTTORI UNIVERSITY, Tottori (JP); TRANS CHROMOSOMICS, INC., Yonago (JP)

(72) Inventors: Yasuhiro Kazuki, Yonago (JP); Satoshi Abe, Yonago (JP); Mitsuo Oshimura, Yonago (JP)

(73) Assignees: National University Corporation Tottori University, Tottori (JP); Trans Chromosomics, Inc., Tottori (JP)

( * ) Notice: Subject to any disclaimer, the term of this patent is extended or adjusted under 35 U.S.C. 154(b) by 368 days.

(21) Appl. No.: 16/346,077

(22) PCT Filed: Oct. 31, 2017

(86) PCT No.: PCT/JP2017/039441
§ 371 (c)(1),
(2) Date: Apr. 29, 2019

(87) PCT Pub. No.: WO2018/079857
PCT Pub. Date: May 3, 2018

(65) Prior Publication Data
US 2019/0254264 A1    Aug. 22, 2019

(30) Foreign Application Priority Data
Oct. 31, 2016  (JP) .................................. 2016-213844

(51) Int. Cl.
| | | |
|---|---|---|
| A01K 67/027 | (2024.01) | |
| C07K 16/06 | (2006.01) | |
| C12N 15/00 | (2006.01) | |
| C12N 15/09 | (2006.01) | |
| C12N 15/85 | (2006.01) | |
| C12P 21/00 | (2006.01) | |

(52) U.S. Cl.
CPC ............ *A01K 67/027* (2013.01); *C07K 16/06* (2013.01); *C12N 15/00* (2013.01); *C12N 15/09* (2013.01); *C12N 15/85* (2013.01); *C12P 21/005* (2013.01); *A01K 2207/15* (2013.01); *A01K 2227/105* (2013.01); *A01K 2267/01* (2013.01); *C12N 2015/8518* (2013.01)

(58) Field of Classification Search
CPC .............. A01K 67/027; A01K 67/0278; A01K 2207/15; A01K 2227/105; A01K 2267/01; C12N 15/85; C07H 21/04
See application file for complete search history.

(56) References Cited

U.S. PATENT DOCUMENTS

| | | |
|---|---|---|
| 2002/0088016 A1 | 7/2002 | Bruggemann |
| 2002/0106629 A1 | 8/2002 | Murphy et al. |
| 2004/0073957 A1 | 4/2004 | Tomizuka et al. |
| 2006/0130157 A1 | 6/2006 | Wells et al. |
| 2012/0272342 A1 | 10/2012 | Oshimura et al. |

FOREIGN PATENT DOCUMENTS

| | | |
|---|---|---|
| CN | 101333516 A | 12/2008 |
| CN | 101389214 A | 3/2009 |
| EP | 0 972 445 A1 | 1/2000 |
| EP | 2 502 992 A1 | 9/2012 |
| EP | 3 252 074 A1 | 12/2017 |
| JP | 2007-312792 A | 12/2007 |
| JP | 2008-200042 A | 9/2008 |
| WO | WO-2011/083870 A1 | 7/2011 |
| WO | WO-2011/163314 A1 | 12/2011 |
| WO | WO-2016/121908 A1 | 8/2016 |

OTHER PUBLICATIONS

Katagiri et al., 2018, US 20180118835 A1, effective filing date, Jan. 30, 2015.*
Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Bruggemann, Marianne, 2002, US 20020088016 A1.*
Brueggemann et al., "Human Antibody Production in Transgenic Animals," Arch. Immunol. Ther. Exp., 2015, 63:101-108.
Supplementary European Search Report dated Jun. 24, 2020 in EP 17864055.3.
International Search Report dated Feb. 6, 2018, in PCT/JP2017/039441.
Takiguchi et al., "A Novel and Stable Mouse Artificial Chromosome Vector," ACS Synthetic Biology, 2014, vol. 3, pp. 903-914.
Office Action dated Jun. 21, 2021 in Indian Patent Application 201947021195.

* cited by examiner

*Primary Examiner* — Shin Lin Chen
(74) *Attorney, Agent, or Firm* — Foley & Lardner LLP

(57) ABSTRACT

This application provides: a non-human animal that comprises a mouse artificial chromosome comprising a human antibody heavy chain gene or gene locus, a human antibody light chain κ gene or gene locus, and/or a human antibody light chain λ gene or gene locus, and in which endogenous antibody genes or gene loci corresponding to at least 2 human antibody genes or gene loci have been knocked out, wherein the animal can be stably retained through generations and can produce human antibodies; a method for producing the non-human animal; and a method for producing human antibodies using the non-human animal.

7 Claims, 37 Drawing Sheets
Specification includes a Sequence Listing.

Fig. 28

| Sample | Human IgM | Human IgG |
|---|---|---|
| Wild-type rat | 0μg/mL | 0μg/mL |
| rTC #1 | 9.9μg/mL | 26.1μg/mL |
| rTC #2 | 10.6μg/mL | 25.5μg/mL |
| rTC #3 | 9.9μg/mL | 25.9μg/mL |

HUMAN ANTIBODY-PRODUCING NON-HUMAN ANIMAL AND METHOD FOR PREPARING HUMAN ANTIBODIES USING SAME

CROSS-REFERENCE TO RELATED APPLICATIONS

This application is the U.S. National Stage of PCT/JP2017/039441, filed Oct. 31, 2017, which claims priority to JP 2016-213844, filed Oct. 31, 2016.

The instant application contains a Sequence Listing which has been submitted in ASCII format via EFS-WEB and is hereby incorporated by reference in its entirety. Said ASCII copy, created on Apr. 29, 2019, is named 081356-0559_sequence.txt and is 16,505 bytes.

TECHNICAL FIELD

The present invention relates to a mouse artificial chromosome (MAC) comprising human antibody genes, and to a non-human animal comprising the MAC and capable of producing a human antibody.

The present invention also relates to a method for preparing the non-human animal.

The present invention further relates to a method for preparing a human antibody using the non-human animal.

BACKGROUND ART

An antibody is used as a therapeutic agent for cancer, rheumatic arthritis, or the like in the field of medicine. For example, Trastuzumab is used for treatment of breast cancer as a molecular targeting antibody medicine for HER2 (or ErbB2) on the cancer cell surface. Also, Tocilizumab is a humanized anti-IL-6 receptor antibody used as a therapeutic agent for rheumatic arthritis.

An antibody is preferably a humanized antibody or human antibody whose therapeutic effects and safety are enhanced when administered to humans. A humanized antibody is obtained by substituting the amino acid sequences of heavy chain and light chain complementarity-determining regions of an antibody derived from a non-human animal such as a mouse, with corresponding complementarity-determining regions (CDR1, CDR2, and CDR3) of human antibody, and the humanized antibody can be prepared by combining the technique of monoclonal antibody preparation with the technique of DNA recombination. In contrast, a human antibody consists of completely human-derived amino acid sequences and can be prepared by, for example, the technique involving the use of a mouse that carries human antibody genes and is capable of producing a human antibody (e.g., KM mice (Kyowa Hakko Kirin Co., Ltd.)) or the phage display method in which an antibody, such as ScFV, is presented in the form of a recombinant antibody on the surface of a fibrous phage.

The technique correlated with the present invention is a technique of preparing a non-human animal, such as mouse, capable of producing a human antibody, and such animal carries human antibody genes. Human antibody genes are separately present on different chromosomes, each of which comprises heavy chain gene, light chain κ gene, or a light chain λ gene, and the size of each gene is approximately 0.9 Mb or greater. In order to prepare a non-human animal capable of producing a human antibody, chromosome engineering techniques, such as use of artificial chromosome vectors, are needed when a human antibody-producing non-human animal is prepared.

Patent Literature 1 discloses a method for preparing a non-human animal, such as mouse, capable of producing a human antibody using a human artificial chromosome comprising human antibody genes, and a method for producing a human antibody using the animal.

Patent Literature 2 discloses a transgenic ungulate animal comprising one or more nucleic acids encoding a part of or the entire human immunoglobulin genes expressing one or more human immunoglobulin molecules through rearrangement, the animal being selected from the group consisting of cattle (or cow), sheep, and goat.

Patent Literature 3 discloses a human artificial chromosome vector comprising human antibody heavy chain gene, human antibody light chain gene, and alternative human antibody light chain gene, an animal comprising the human artificial chromosome vector, and a method for producing a human antibody.

Patent Literature 4 discloses a mouse artificial chromosome.

Non-Patent Literature 1 is a review concerning the production of human antibodies using a transgenic animal. This literature points out low efficiency for human antibody production using in previous transgenic animals as a problem to be solved. To this end, this literature proposes that endogenous antibody genes should be knocked out and that the V, D, and J segments of a human variable region should be bound to the endogenous C gene.

CITATION LIST

Patent Literature

Patent Literature 1: JP Patent No. 4,082,740
Patent Literature 2: JP Patent No. 3,797,974
Patent Literature 3: WO 2011/062206
Patent Literature 4: JP Patent No. 5,557,217

Non-Patent Literature

Non-Patent Literature 1: M. Bruggemann et al., Arc. Immunol. Ther. Exp., 2015, 63: 101-108

SUMMARY OF INVENTION

Technical Problem

An object of the present invention is to provide human antibody-producing non-human animals (e.g., mouse, rat, etc.) that is stably retained and is transmittable to progeny (or offsprings), and a method for producing human antibodies using the animals.

Solution to Problem

In short, the present invention includes the following characteristics.

(1) A non-human animal comprising a mouse artificial chromosome vector comprising a human antibody heavy chain gene or gene locus and a human antibody light chain κ gene or gene locus (hereafter, referred to as "hIGHK-MAC").

(2) A non-human animal comprising a mouse artificial chromosome vector comprising a human antibody heavy chain gene or gene locus and a human antibody light chain λ gene or gene locus (hereafter, referred to as "hIGHL-MAC").

(3) A non-human animal comprising a mouse artificial chromosome comprising a human antibody heavy chain gene or gene locus and a human antibody light chain κ gene or gene locus (hereafter, referred to as "hIGHK-MAC") and a mouse artificial chromosome vector comprising a human antibody heavy chain gene or gene locus and a human antibody light chain λ gene or gene locus (hereafter, referred to as "hIGHL-MAC").

(4) A non-human animal comprising a mouse artificial chromosome vector comprising a human antibody heavy chain gene or gene locus, a human antibody light chain κ gene or gene locus, and a human antibody light chain λ gene or gene locus (hereafter, referred to as "hIGHKL-MAC").

(5) The non-human animal according to any of (1) to (4), which is a mammal.

(6) The non-human animal according to (5), wherein the mammal is a rodent.

(7) The non-human animal according to (6), wherein the rodent is mouse or rat.

(8) The non-human animal according to any of (1) to (7), wherein at least two endogenous antibody genes or gene loci of the non-human animal are knocked out.

(9) A method for producing a non-human animal capable of producing a human antibody comprising: crossbreeding the non-human animal according to (1) with a same non-human animal species in which endogenous antibody genes or gene loci corresponding to the human antibody heavy chain gene or gene locus and the human antibody light chain κ and λ genes or gene loci have been knocked out; and selecting a non-human animal that comprises hIGHK-MAC and in which the endogenous antibody genes or gene loci have been knocked out.

(10) A method for producing a non-human animal capable of producing a human antibody comprising: crossbreeding the non-human animal according to (2) with a same non-human animal species in which endogenous antibody genes or gene loci corresponding to the human antibody heavy chain gene or gene locus and the human antibody light chain κ and λ genes or gene loci have been knocked out; and selecting a non-human animal that comprises hIGHL-MAC and in which the endogenous antibody genes or gene loci have been knocked out.

(11) A method for producing a non-human animal capable of producing a human antibody comprising: a step of crossbreeding the non-human animal according to (1) with the non-human animal according to (2) to produce a non-human animal comprising hIGHK-MAC and hIGHL-MAC; and a step of crossbreeding the produced non-human animal with a same non-human animal species in which endogenous antibody genes or gene loci that are corresponding to the human antibody heavy chain gene or gene locus and the human antibody light chain κ and λ genes or gene loci have been knocked out, and then selecting a non-human animal that comprises hIGHK-MAC and hIGHL-MAC and in which the endogenous antibody genes or gene loci have been knocked out.

(12) A method for producing a non-human animal capable of producing a human antibody comprising: crossbreeding a non-human animal that comprises a mouse artificial chromosome vector comprising a human antibody heavy chain gene or gene locus and a human antibody light chain κ gene or gene locus (hIGHK-MAC) and in which endogenous antibody genes or gene loci that are corresponding to the human antibody heavy chain gene or gene locus and the human antibody light chain κ and λ genes or gene loci have been knocked out, with a non-human animal that comprises a mouse artificial chromosome vector comprising a human antibody heavy chain gene or gene locus and a human antibody light chain λ gene or gene locus (hIGHL-MAC) and in which endogenous antibody genes or gene loci corresponding to the human antibody heavy chain gene or gene locus and the human antibody light chain κ and λ genes or gene loci have been knocked out; and selecting a non-human animal that comprises hIGHK-MAC and hIGHL-MAC and in which the endogenous antibody genes or gene loci have been knocked out.

(13) A method for producing a non-human animal capable of producing a human antibody comprising: crossbreeding the non-human animal according to (4) with a same non-human animal species in which endogenous antibody genes corresponding to the human antibody heavy chain gene or gene locus, the human antibody light chain κ gene or gene locus, and the human antibody light chain λ gene or gene locus have been knocked out; and selecting a non-human animal that comprises hIGHKL-MAC and in which the endogenous antibody genes or gene loci have been knocked out.

(14) A method for producing a human antibody comprising: a step of administering a antigenic substance to the non-human animal according to any of (1) to (8); and a step of collecting the produced human antibody that binds to the antigenic substance, from the human animal.

(15) The method according to (14), wherein the antigenic substance is a cell, a protein, a polypeptide, or a peptide.

(16) A method for producing a human monoclonal antibody comprising: a step of administering an antigenic substance to the non-human animal according to any of (1) to (8); a step of removing spleen cells from the non-human animal; a step of fusing the spleen cells to myeloma cells to produce hybridomas; and a step of collecting an antibody binding to the antigenic substance from the hybridomas.

(17) The method according to (16), wherein the antigenic substance is a cell, a protein, a polypeptide, or a peptide.

(18) A mouse artificial chromosome vector comprising a human antibody heavy chain gene or gene locus, a human antibody light chain κ gene or gene locus, and/or a human antibody light chain λ gene or gene locus.

According to the present invention, the non-human animal produces human antibodies, in which endogenous antibody heavy chain and light chain genes or gene loci have been knocked out, and which comprises human antibody heavy chain and light chain genes or gene loci. Even progeny of this animal can stably comprise human antibody genes or gene loci (i.e., heavy chain gene or gene locus, light chain κ gene or gene locus, and light chain λ gene or gene locus) and can produce human antibodies. Herein, the mouse artificial chromosome has substantially no mouse-derived genes, it comprises human antibody genes, and it is stably transmitted to offsprings of a rodent, such as mouse or rat.

The description of the present application includes the contents described in Japanese Patent Application No. 2016-213844, from which the present application claims priority.

BRIEF DESCRIPTION OF DRAWINGS

FIG. 28 shows the results of ELISA evaluation of rats, in which IGHK-MAC was transmitted to progeny, for production of human antibodies in blood serum.

EMBODIMENTS OF THE INVENTION

Figure 1:
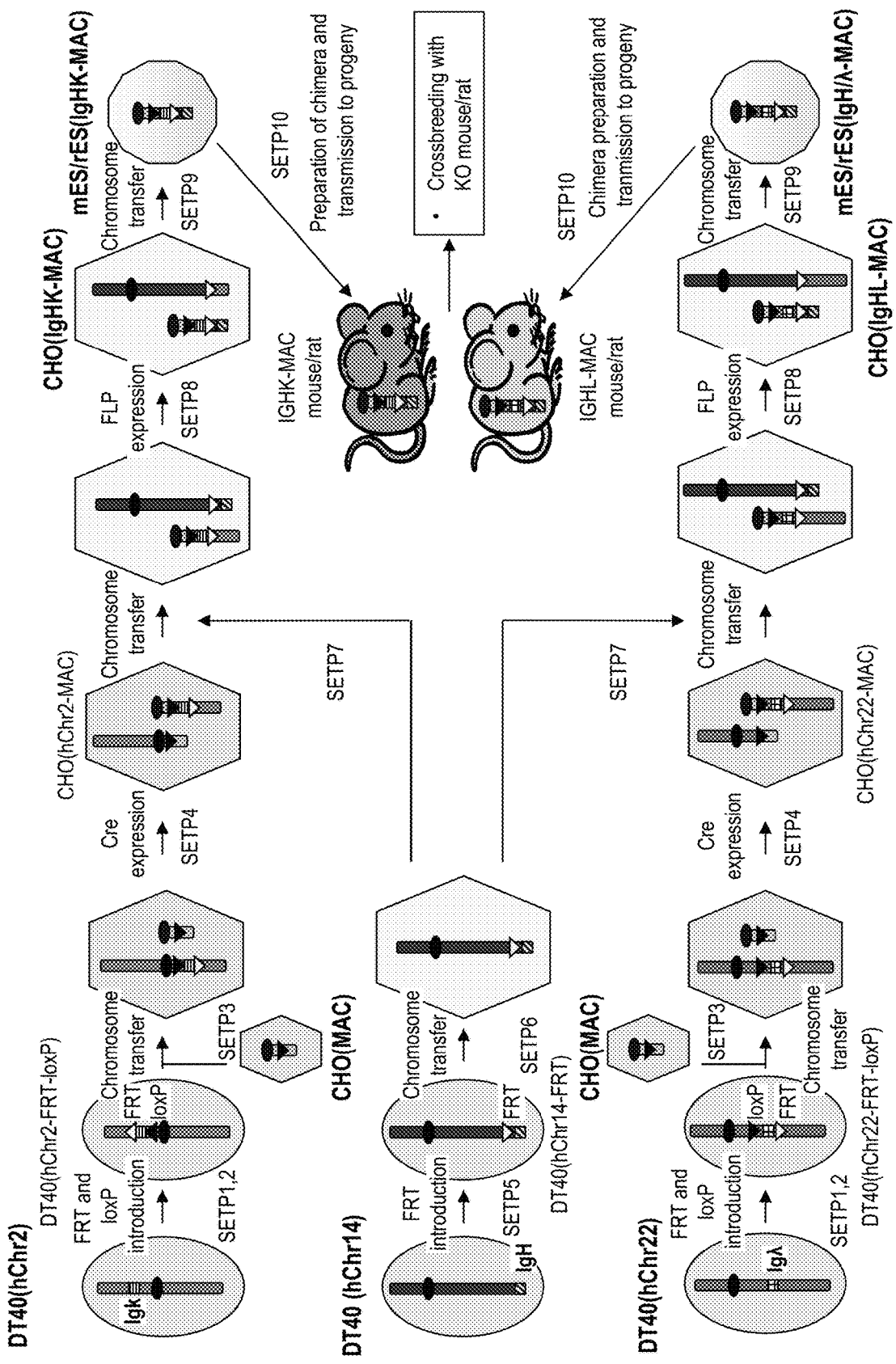
FIG. 1 schematically shows procedures for producing a human antibody-producing mouse or rat using mouse artificial chromosomes (MACs).

The present invention provides a non-human animal that comprises a mouse artificial chromosome (MAC) comprising human antibody heavy chain and light chain genes or gene loci and is capable of producing a human antibody, and a method for producing human antibodies using the non-human animal.

Hereafter, the present invention will be described in more detail.

1. Non-Human Animal Capable of Producing Human Antibody 1.1 Mouse Artificial Chromosome (MAC)

As used herein, the term "mouse artificial chromosome" (also, referred to as "mouse artificial chromosome vector") is an artificial chromosome constructed by top-down approach, and such artificial chromosome vector can comprise, in addition to a naturally-occurring centromere obtained by completely or substantially completely deleting gene regions from the mouse chromosome by chromosome modification, telomere sequences at both ends and a foreign element such as DNA sequence insertion site. Such vector can be constructed in accordance with, for example, the process for producing a mouse artificial chromosome vector developed by the present inventors (JP 2011-083870 A and JP Patent No. 5,557,217).

The mouse artificial chromosome can stably replicate and can be stably distributed as a chromosome independent from the native chromosome of a host cell. The mouse-derived chromosome fragment is a fragment of any of mouse chromosomes 1 to 19 and X and Y chromosomes, preferably a fragment of any of mouse chromosomes 1 to 19 (where the fragment is a long-arm fragment obtained by deleting at least 99.5%, preferably almost 100% of all endogenous genes from the long arm). This fragment includes a long-arm fragment obtained by deleting a long-arm distal region at a mouse chromosome long-arm site proximal to the centromere.

Sequence information of mouse chromosomes is available from DDBREMBL/GenBank, chromosome databases at Santa Cruz Biotechnology, Inc., and other organizations.

The term "long arm" of a chromosome refers to a chromosome region from the centromere side to the region containing a gene region in a mouse chromosome. Meanwhile, the mouse chromosome has almost no short arm.

The term "distal region" refers to a region distal from the centromere (i.e., a region of the telomere side). On the other hand, a region near the centromere (i.e., a region of the centromere side) is referred to as the "proximal region." The long-arm distal region is a region positioned on the telomere side than a specific site of the long arm, and the long-arm proximal region is a region positioned on the centromere side than a specific site of the long arm.

The mouse artificial chromosome vector is characterized by comprising a naturally-occurring centromere derived from a mouse chromosome, a long-arm fragment derived from a mouse chromosome formed by deleting a long-arm distal region from a mouse chromosome long-arm site proximal to the centromere, and a telomere sequence, and by being stably retained in cells and tissues of a mammal.

The term "naturally-occurring centromere derived from a mouse chromosome" refers to the entire centromere (or the intact centromere) of any one of mouse chromosomes. Accordingly, such centromere does not include: a structure having a centromere function which is obtained spontaneously or synthetically using a portion of the centromere sequence of a mouse chromosome; or the centromere of a chromosome derived from other animal species.

The "long-arm fragment derived from a mouse chromosome obtained by deleting a long-arm distal region from a mouse chromosome long-arm site proximal to the centromere" preferably eliminates influences of endogenous genes as much as possible, so as to stably keep the vector of the present invention in cells or tissues of a rodent, such as mouse or rat, and to refrain from disturbing the development of mice and the transmission to progeny (or offsprings). Thus, the long-arm fragment is obtained by deleting a long arm of the mouse chromosome at a long-arm site proximal to the centromere, so as to remove the endogenous genes from the long arm of the mouse chromosome. Such long-arm fragment is obtained by deleting at least 99.5%, preferably at least 99.7%, more preferably 99.8%, and most preferably 99.9% to 100% of total endogenous genes (the number of genes) at the long-arm site proximal to the centromere.

The term "retention rate" used herein refers to a rate of cells having an artificial chromosome in cultured cells or tissue cells of mammals, including rodents such as mouse and rat.

The term that the chromosome vector of the present invention is "stably retained" means that, during mitosis (or cell division), the chromosome vector dropout is difficult to cause, and, that is, the chromosome vector is stably retained in cells even after mitosis, and the chromosome vector is efficiently transmitted to daughter cells or offspring mice.

In the case of an artificial chromosome vector derived from, for example, a fragment of mouse chromosome 11, the long-arm fragment is formed by deleting a region distant from, for example, AL671968, or BX572640 (located at a position closer to the centromere side than AL671968), CR954170 (located at a position closer to the centromere side than AL671968 and BX572640), or AL713875 (located at a position closer to the centromere side than AL671968) of the long arm of the chromosome 11, although the long-arm fragment is not limited thereto. In another case of an artificial chromosome vector derived from a fragment of mouse chromosome 15, the long-arm fragment is formed by deleting a region distant from, for example, AC121307 or AC161799, although the long-arm fragment is not limited thereto. In further case of an artificial chromosome vector derived from a fragment of mouse chromosome 16, the long-arm fragment is formed by deleting a region distant from, for example, AC127687 or AC140982, although the long-arm fragment is not limited thereto. These basic structures can further comprise a DNA sequence insertion site, such as loxP, to insert a human antibody gene sequence.

The retention rate of the vector increases in cells or tissues of mammals including rodents such as mice, rats, and hamsters. Thus, the vector is stably retained in cells, a human antibody gene (a group of human antibody genes) of interest can be stably maintained for a long period of time, the amount of transgenes does not vary among rodent individuals or tissues, and the transgenes can be expressed for a long period of time. Compared with a human artificial chromosome (HAC), interestingly, a variation of the retention rate is extremely small among tissues including hematopoietic tissues in which the retention rate of a HAC is very low and is less than 20%, and the retention rate is 90% or more in any tissues tested (e.g., tissues derived from the liver, intestine, kidney, spleen, lung, heart, skeletal muscle, brain, or bone marrow).

The term "DNA sequence insertion site" used herein refers to a site of an artificial chromosome into which a desirable DNA (including a gene) sequence can be inserted, such as a recognition site for a site-directed recombinase. Examples of such recognition site include, but are not limited to, loxP (a Cre recombinase recognition site), FRT (a Flp recombinase recognition site), φC31attB and φC31attP (φC31 recombinase recognition sites), R4attB and R4attP (R4 recombinase recognition sites), TP901-1attB and TP901-1attP (TP901-1 recombinase recognition sites), and BxblattB and BxblattP (Bxb1 recombinase recognition sites).

The term "site-directed recombinase" used herein refers to an enzyme that induces recombination with a desirable DNA sequence specifically at the recognition site of the enzyme. Examples thereof include Cre integrase (also referred to as "Cre recombinase"), Flp recombinase, φC31 integrase, R4 integrase, TP901-1 integrase, and Bxb1 integrase.

The term "telomere sequence" used herein refers to a natural telomere sequence derived from the same or different species or an artificial telomere sequence. In the case of the same species, the animal is of the same species from which a chromosome fragment of an artificial chromosome vector is derived. In contrast, the different species is a mammal other than the mouse (including a human). Also, the artificial telomere sequence is a sequence having a telomere function, which is artificially prepared, such as a (TTAGGG)n sequence (where "n" indicates the number of repetitions). A telomere sequence can be introduced into an artificial chromosome by telomere truncation (i.e., substitution of a telomere sequence) as disclosed in, for example, WO 00/10383. The telomere truncation can be employed to shorten a chromosome during preparation of the artificial chromosome of the present invention.

The term "embryonic stem cell" or "ES cell" used herein refers to a semi-immortalized pluripotent stem cell that is established from an inner cell mass of a blastocyst of a fertilized egg derived from a mammal (M. J. Evans and M. H. Kaufman, 1981, Nature 292: 154-156; J. A. Thomson et al., 1999, Science 282: 1145-1147; J. A. Thomson et al., 1995, Proc. Natl. Acad. Sci. U.S.A., 92: 7844-7848; J. A. Thomson et al., 1996, Biol. Reprod., 55: 254-259; J. A. Thomson and V. S. Marshall, 1998, Curr. Top. Dev. Biol. 38: 133-165). Cells having properties equivalent to those of such cells and artificially induced by reprogramming of somatic cells are "induced pluripotent stem cells" or "iPS cells" (K. Takahashi and S. Yamanaka, 2006, Cell 126: 663-676; K. Takahashi et al., 2007, Cell 131: 861-872; J. Yu et al., 2007, Science 318:1917-1920).

Hereafter, production of the mouse artificial chromosome vector and applications thereof will be described.

The artificial chromosome vector of the present invention can be prepared in accordance with a method comprising the following steps of:
  (a) obtaining a cell comprising (or carrying) a mouse chromosome;
  (b) deleting a long-arm distal region of the mouse chromosome so as not to include a majority (i.e., 99.5% to 100%, and preferably 100%) of endogenous genes; and
  (c) inserting one or more DNA sequence insertion sites into a long-arm proximal region. The order of the steps (b) and (c) may be interchangeable.

Step (a):

In order to prepare the artificial chromosome vector according to the present invention, a cell comprising a mouse chromosome is first to be produced. For example, a mouse embryonic fibroblast (mChr11-BSr), which is a mouse fibroblast carrying a mouse chromosome labeled with a drug resistance gene (e.g., blasticidin S resistance gene (BSr)), is subjected to cell fusion to a mouse A9 (neo), which is a mouse A9 cell (ATCC VA20110-2209) with a neo gene (i.e., a G418-resistant gene) introduced therein. Next, the mouse A9 hybrid cell comprising the mouse chromosome labeled with a drug resistance gene; i.e. the mouse A9× mouse embryonic fibroblast (neo; mChr11-BSr), is used to transfer the chromosome into a cell having a high homologous recombination rate, thereby being able to prepare the cell comprising a mouse chromosome. The mouse fibroblast is available based on procedures described in literatures. For example, the mouse fibroblast can be established from C57B6 mouse commercially available from CLEA Japan, Inc. An example of an available cell having a high homologous recombination rate is a chicken DT40 cell (Dieken et al., Nature Genetics, 12, 1 74-182, 1996). Furthermore, the above-described transfer can be carried out using known chromosome transfer techniques, such as microcell fusion (Koi et al., Jpn. J. Cancer Res., 80, 413-418, 1973).

Step (b):

In a cell having a single mouse-derived chromosome, a long-arm distal region of the mouse chromosome is deleted. It is important to delete (or remove or cleave out) a majority of endogenous genes present in the long arm and then to construct an artificial chromosome comprising the mouse centromere. That is, it is important to determine a cleavage site so as to delete (or remove or cleave out) a region containing at least 99.5%, preferably at least 99.7%, more preferably at least 99.8%, and most preferably 99.9 to 100% of all endogenous genes (the number of the genes) present in the long arm. Thus, cells, tissues, or individuals, which carry the artificial chromosome and is derived from a mammal such as rodent (preferably mouse or rat), can stably retain the artificial chromosome at a high retention rate, and it can be used for precise analysis of a gene (a group of genes) of interest and for production of materials. The above-described endogenous genes can be deleted by, for example, telomere truncation. Specifically, a targeting vector comprising an artificial telomere sequence is constructed and is used to obtain a clone into which an artificial or natural telomere sequence has been inserted at a desirable position on the chromosome by homologous recombination in a cell comprising a mouse chromosome. Thus, a deletion mutant can be obtained by telomere truncation. That is, the desirable position (or site) is a cleavage position of a long-arm distal region to be deleted. The artificial telomere sequence is inserted into this position by substitution via the homologous recombination, so that the long-arm distal region is deleted. This position can be appropriately determined depending on a desirable sequence design when constructing a targeting vector. For example, a desirable sequence is designed based on the DNA sequence of the mouse chromosome long arm, so that the telomere truncation occurs at a position closer to the telomere side than the desirable sequence. As a result, a fragment of mouse chromosome 11 resulting from deletion of a majority of endogenous genes can be obtained. For other chromosomes, the telomere truncation can be carried out in the same manner.

Step (c):

As a DNA sequence insertion site, a recognition site for a site-specific recombinase can be preferably inserted. Specifically, the phenomenon such that a certain enzyme recognizes a specific recognition site and causes DNA recombination specifically at the recognition site is known. The mouse artificial chromosome vector according to the present invention can use a system having such an enzyme and its recognition site to insert or incorporate a gene or DNA sequence of interest. Examples of such system include, but are not limited to, a system having bacteriophage P1-derived Cre enzyme and its recognition site, i.e., the loxP sequence (a Cre/loxP system; B. Sauer in Methods of Enzymology, 1993, 225, 890-900), a system having budding yeast-derived Flp enzyme and its recognition site, i.e., FRT (Flp Recombination Target) sequence (a Flp/FRT system), a system having Streptomyces phage-derived φC31 integrase and its recognition site, i.e., φC31 attB/attP sequence, a system having R4 integrase and its recognition site, i.e., R4 attB/attP sequence, a system having TP901-1 integrase and its recognition site, TP901-1 attB/attP sequence, and a system having Bxb1 integrase and its recognition site, i.e., Bxb1 attB/attP sequence, provided that the system can function as a DNA sequence insertion site.

In order to insert a recognition site for such a site-specific recombinase, known methods, such as homologous recombination, can be employed. The position and the number of insertion can be appropriately determined in a long-arm proximal region and a short-arm proximal region.

Into the mouse artificial chromosome vector, a single type of recognition site(s) or different types of recognition sites can be inserted. The setting of a recognition site enables identification of an insertion position for a desirable gene or gene locus or DNA sequence (i.e., human antibody heavy chain gene or gene locus, human antibody light chain κ gene or gene locus, or human antibody light chain λ gene or gene locus). Thus, the insertion position is fixed, and no unexpected positional effects would be exerted.

Preferably, a reporter gene may be inserted into mouse artificial chromosome vector having a DNA sequence insertion site in advance while keeping (or maintaining) an insertion site for a desirable gene or DNA sequence. Examples of reporter genes include, but are not particularly limited to, fluorescent protein genes (e.g., a green fluorescent protein (GFP or EGFP) gene and a yellow fluorescent protein (YFP) gene), a tag-protein-encoding DNA, a β-galactosidase gene, and a luciferase gene, preferably GFP or EGFP.

The mouse artificial chromosome vector may further comprise a selection marker gene. A selection marker is effective when selecting a cell transformed with the vector. As a selection marker gene, either or both of a positive selection marker gene and a negative selection marker gene are exemplified. Examples of positive selection marker genes include drug-resistant genes such as neomycin-resistant gene, ampicillin-resistant gene, blasticidin S (BS)-resistant gene, puromycin-resistant gene, geneticin (G418)-resistant gene, and hygromycin-resistant gene. In addition, examples of negative selection marker genes include herpes simplex thymidine kinase (HSV-TK) gene and diphtheria toxin A fragment (DT-A) gene. In general, HSV-TK is used in combination with ganciclovir or acyclovir.

Homologous recombination can be preferably used as a technique for inserting a reporter gene or a desirable exogenous gene or DNA into the mouse artificial chromosome vector. The homologous recombination can be carried out using a targeting vector which is obtained by ligating an DNA cassette to be inserted between sequences (5' arm and 3' arm) homologous to nucleotide sequences of 5' and 3' regions (each having approximately 1 to 4 kb, preferably approximately 2 to 4 kb) at an insertion position of the mouse chromosome. Examples of vectors that can be used for this purpose include plasmid vectors, phage vectors, cosmid vectors, and viral vectors, preferably plasmid vectors. Examples of a basic plasmid for targeting vector construction include, but are not limited to, V907 and V913 (Lexicon Genetics). The basic vector may comprise one or two or more sequences or elements that are generally inserted for vector construction, such as a promoter, an enhancer, a selection marker gene, or a replication origin.

The mouse artificial chromosome vector prepared by the method described above comprises a mouse-derived chromosome fragment (which comprises a natural centromere, a long-arm fragment formed by deleting at least 99%, and preferably at least 99.5% to 100%, of endogenous genes, and a short arm (if present)), and an artificial telomere sequence. The above centromere constitutes the entire mouse chromosome centromere structure, which is used for the artificial chromosome construction. The DNA sequence insertion site, the selection marker gene, the exogenous gene (or DNA), or the like as described below can be inserted into the DNA structure of the vector.

The above mouse artificial chromosome vector preferably comprises one or more DNA sequence insertion sites, such as a recognition site for site-specific recombinase (e.g., a loxP sequence which is a Cre enzyme recognition site). Examples of recognition sites for the site-specific recombinase include, but are not limited to, loxP sequences of GFP-PGKneo-loxP-3' HPRT type, 5' HPRT-loxP-hyg type, PGKneo-loxP-3' HPRT type, and GFP-5' HPRT-loxP-PGKhyg type. In the above, "GFP" represents a green fluorescent protein gene, "PGKneo" represents a phosphoglycerate kinase promoter/neomycin-resistant gene cassette, "HPRT" represents a hypoxanthine guanine phosphoribosyltransferase gene, and "hyg" represents a hygromycin-resistant gene.

The above-described mouse artificial chromosome vector may further comprise a reporter gene or a selection marker gene (e.g., a positive selection marker gene or a negative selection marker gene). The vector may further comprise a desirable exogenous gene or DNA sequence.

The advantages of the mouse artificial chromosome vector according to the present invention include advantages of conventional artificial chromosome vectors as follows: 1) the vector is not inserted into a host chromosome but is independently maintained, so that a host gene is not destroyed; 2) the vector is stably retained at a certain copy number (which may be a plurality of (or multiple) copies) and is exposed to the physiological expression regulation of a host cell, so that the overexpression of or the loss of expression of an inserted gene is not caused; 3) a size of DNA that can be introduced is not limited, so that an expression regulatory region-containing gene or a plurality of genes/isoforms can be introduced; 4) a retention rate of the vector in a rodent cell or individual is increased, compared with that of conventional artificial chromosomes; 5) a transgene can be stably expressed for a long period of time and a rate of transmission of the vector to offsprings (or progeny) is improved, so that efficiency for transgenic mouse production is improved; and 6) because of less variation among tissues after introduction of the vector, that is, a retention rate is 90% or higher in any tissue, and it is 90% or higher even in a hematopoietic tissue, which usually has a retention rate of less than 20% in the case of the HAC.

As described below, the mouse artificial chromosome vector can comprise a human antibody heavy chain gene or gene locus, a human antibody light chain κ gene or gene locus, and/or a human antibody light chain λ gene or gene locus. Specifically, a mouse artificial chromosome vector comprising a human antibody heavy chain gene or gene locus and a human antibody light chain κ gene or gene locus (hIGHK-MAC), a mouse artificial chromosome vector comprising a human antibody heavy chain gene or gene locus and a human antibody light chain λ gene or gene locus (hIGHL-MAC), and a mouse artificial chromosome vector comprising a human antibody heavy chain gene or gene locus, a human antibody light chain κ gene or gene locus, and a human antibody light chain λ gene or gene locus (hIGHKL-MAC) are comprised within the scope of the mouse artificial chromosome vector.

1.2 Human Antibody Gene

A human antibody gene can be introduced into the mouse artificial chromosome vector according to the present invention.

The term "human antibody gene or gene locus" used herein refers to the human antibody heavy chain gene or gene locus derived from human chromosome 14, the human antibody light chain κ gene or gene locus derived from human chromosome 2, and/or the human antibody light chain λ gene or gene locus derived from human chromosome 22, unless otherwise specified. Specifically, the human antibody gene or gene locus is represented by the nucleotide sequence as shown in, for example, the immunoglobulin heavy locus (human) NC_000014.9 (nucleotide numbers 105586437 . . . 106879844) or (nucleotide numbers 105264221 . . . 107043718)) of human chromosome 14, the immunoglobulin kappa locus (human) NC_000002.12 (nucleotide numbers 88857361 . . . 90235368) or (nucleotide numbers 88560086 . . . 90265666) of human chromosome 2, or the immunoglobulin lambda locus (human) NC_000022.11 ((nucleotide numbers 22026076 . . . 22922913) or (nucleotide numbers 21620362 . . . 23823654) of human chromosome 22. The nucleotide length of the human antibody heavy chain gene or gene locus is approximately 1.3 Mb, that of the human antibody light chain κ gene or gene locus is approximately 1.4 Mb, and that of the human antibody light chain λ gene or gene locus is approximately 0.9 Mb.

The mouse antibody heavy chain gene or gene locus is present on mouse chromosome 12, the mouse antibody light chain κ gene or gene locus is present on mouse chromosome 6, and the mouse antibody light chain λ gene or gene locus is present on mouse chromosome 16. Specifically, the mouse antibody heavy chain gene or gene locus is represented by, for example, the nucleotide sequence of Chromosome 12, NC_000078.6 (113258768 . . . 116009954, complement), the mouse antibody light chain κ gene or gene locus is represented by the nucleotide sequence of Chromosome 6, NC_000072.6 (67555636 . . . 70726754), and the mouse antibody light chain λ gene or gene locus is represented by the nucleotide sequence of Chromosome 16, NC_000082.6 (19026858 . . . 19260844, complement).

The rat antibody heavy chain gene or gene locus is present on rat chromosome 6, the rat antibody light chain κ gene or gene locus is present on rat chromosome 4, and the rat antibody light chain λ gene or gene locus is present on rat chromosome 11. The nucleotide sequences of these genes or gene loci are available from, for example, U.S. NCBI (e.g., GenBank) and known literature.

In the present invention, the mouse artificial chromosome vector comprising the human antibody genes is: a mouse artificial chromosome vector comprising the human antibody heavy chain gene or gene locus derived from human chromosome 14 and the human antibody light chain κ gene or gene locus derived from human chromosome 2 (hIGHK-MAC); or a mouse artificial chromosome vector comprising the human antibody heavy chain gene or gene locus derived from human chromosome 14 and the human antibody light chain λ gene or gene locus derived from human chromosome 22 (hIGHL-MAC); or a mouse artificial chromosome vector comprising all of the human antibody heavy chain gene or gene locus derived from human chromosome 14, the human antibody light chain κ gene or gene locus derived from human chromosome 2, and the human antibody light chain λ gene or gene locus derived from human chromosome 22 (hIGHKL-MAC). Such vectors can be prepared by chromosome engineering techniques described herein.

The non-human animal according to the present invention described below is: an animal that carries (or comprises) a mouse artificial chromosome vector comprising the human antibody heavy chain gene or gene locus derived from human chromosome 14 and the human antibody light chain κ gene or gene locus derived from human chromosome 2 and a mouse artificial chromosome vector comprising the human antibody heavy chain gene or gene locus derived from human chromosome 14 and the human antibody light chain λ gene or gene locus derived from human chromosome 22; or an animal that carries (or comprises) a mouse artificial chromosome vector comprising the human antibody heavy chain gene or gene locus derived from human chromosome 14, the human antibody light chain κ gene or gene locus derived from human chromosome 2, and the human antibody light chain λ gene or gene locus derived from human chromosome 22. Thus, the non-human animal enables production of a human antibody to an antigenic substance when such antigenic substance is administered.

As used herein, the term "human antibody" may be of any class and subclass of human immunoglobulin (Ig). Examples of classes include IgG, IgA, IgM, IgD, and IgE, and examples of subclasses include IgG1, IgG2, IgG3, IgG4, IgA1, and IgA2. These classes and subclasses can be classified in accordance with differences in heavy chains, IgG chains are referred to as γ chains, IgG1 to IgG4 chains are referred to as γ1, γ2, γ3, and γ4 chains, respectively, and IgA, IgM, IgD, and IgE chains are referred to as α chains (α1 and α2), μ chain, δ chain, and ε chain, respectively. It is known that each antibody light chain comprises a κ chain and a λ chain and that, when reconstitution of the κ chain gene is not successfully completed during rearrangement of the immunoglobulin gene, the λ chain gene is reconstituted. The human antibody heavy chain gene locus comprises, in the 5' to 3' direction, a V (variable) region gene comprising VH1, VH2 . . . VHm (where m is, for example, 38 to 46), a D (diversity) region gene comprising DH1, DH2 . . . DHn (where n is, for example, 23), a J (joining) region gene comprising JH1, JH2 . . . JHr (where r is 6), and a C (constant) region gene comprising Cμ, Cδ, γ3, Cγ1, Cα1, Cγ2, Cγ4, Cε, and Cα2. An antibody that is produced by rearrangement of the human immunoglobulin genes in the immune system is a human antibody.

A human antibody molecule is composed of 2 human antibody heavy chains and 2 human antibody light chains, wherein each heavy chain is bound to each light chain by 2 disulfide bonds, and 2 heavy chains are bound to each other by 2 disulfide bonds between constant (C) regions. In each variable (V) region of an antibody molecule, there are 3 complementarity-determining regions (CDRs) with particularly high degrees of mutations (i.e., being hypervariable) referred to as CDR1, CDR2, and CDR3 from the N terminus. Antibody-antigen binding properties vary depending on differences in sequences of the CDRs. It is known that antibody diversity arises from reconstitution of the immunoglobulin gene.

1.3 Production of Non-Human Animal

As described above, the non-human animal according to the present invention is: an animal that carries (or comprises) a mouse artificial chromosome vector comprising the human antibody heavy chain gene or gene locus derived from human chromosome 14 and the human antibody light chain κ gene or gene locus derived from human chromosome 2 and a mouse artificial chromosome vector comprising the human antibody heavy chain gene or gene locus derived from human chromosome 14 and the human antibody light chain λ gene or gene locus derived from human chromosome 2; or an animal that carries (or comprises) a mouse artificial chromosome vector comprising the human antibody heavy chain gene or gene locus derived from human chromosome 14, the human antibody light chain κ gene or gene locus derived from human chromosome 2, and the human antibody light chain λ gene or gene locus derived from human chromosome 22.

Specifically, the non-human animal according to the present invention (a mouse and a rat) capable of producing a human antibody can be prepared in accordance with the procedures shown in, for example, FIG. 1.

Hereafter, examples of the production of non-human animals using mouse artificial chromosomes are described.

Each of an animal cell carrying the human antibody light chain κ gene or gene locus derived from human chromosome 2 (e.g., DT40) and an animal cell carrying the human antibody light chain λ gene or gene locus derived from human chromosome 22 (e.g., DT40), both being modified by introduction of recognition sites for site-directed recombinases (e.g., loxP and FRT; Steps 1, 2 of FIG. 1), is transferred into a rodent cell (e.g., CHO) carrying the mouse artificial chromosome (MACs) by cell fusion (Step 3 of FIG. 1), and expression of a site-directed recombinase (e.g., Cre) is induced to prepare a rodent cell carrying a MAC comprising the human antibody light chain κ gene or gene locus, or a rodent cell carrying a MAC comprising the human antibody light chain λ gene or gene locus (Step 4 of FIG. 1).

The site-directed recombinase recognition site (e.g., FRT) is introduced into an area in the vicinity of the human antibody heavy chain gene or gene locus on human chromosome 14 carried in an animal cell (e.g., DT40) (Step 5 of FIG. 1), and the animal cell carrying the modified human antibody heavy chain gene or gene locus is transferred into a rodent cell (e.g., CHO) carrying MAC by cell fusion. Thus, a rodent cell carrying a MAC comprising the human antibody heavy chain gene or gene locus is prepared (Step 6 of FIG. 1).

Each of the rodent cell carrying a MAC comprising the human antibody light chain κ gene or gene locus and the rodent cell carrying a MAC comprising the human antibody light chain λ gene or gene locus is subjected to fusion to the rodent cell carrying the human antibody heavy chain gene or gene locus, thereby to transfer the MAC comprising the human antibody light chain κ gene or gene locus or the MAC comprising the human antibody light chain λ gene or gene locus into the rodent cell carrying the human antibody heavy chain gene or gene locus (Step 7 of FIG. 1). Then, by inducing the expression of a site-directed recombinase (e.g., FLP), the rodent cell carrying a MAC comprising the human antibody heavy chain gene or gene locus derived from human chromosome 14 and the human antibody light chain κ gene or gene locus derived from human chromosome 2, or the rodent cell carrying a MAC comprising the human antibody heavy chain gene or gene locus derived from human chromosome 14 and the human antibody light chain λ gene or gene locus derived from human chromosome 22, is prepared (Step 8 of FIG. 1).

Each of the rodent cell carrying a MAC comprising the human antibody heavy chain gene or gene locus derived from human chromosome 14 and the human antibody light chain κ gene or gene locus derived from human chromosome 2 and the rodent cell carrying a MAC comprising the human antibody heavy chain gene or gene locus derived from human chromosome 14 and the human antibody light chain λ gene or gene locus derived from human chromosome 22 is subjected to fusion to a pluripotent stem cell (e.g., an ES or iPS cell) of a non-human animal (e.g., a mouse or rat) by the microcell fusion technique, thereby producing a non-human animal pluripotent stem cell that carries a MAC comprising the human antibody heavy chain gene or gene locus derived from human chromosome 14 and the human antibody light chain κ gene or gene locus derived from human chromosome 2, or a non-human animal pluripotent stem cell that carries a MAC comprising the human antibody heavy chain gene or gene locus derived from human chromosome 14 and the human antibody light chain λ gene or gene locus derived from human chromosome 22 (Step 9 of FIG. 1).

Each of the non-human animal pluripotent stem cell that carries a MAC comprising the human antibody heavy chain gene or gene locus derived from human chromosome 14 and the human antibody light chain κ gene or gene locus derived from human chromosome 2 and the pluripotent stem cell induced from a non-human animal that carries a MAC comprising the human antibody heavy chain gene or gene locus derived from human chromosome 14 and the human antibody light chain λ gene or gene locus derived from human chromosome 22 is transferred into an early embryo of a non-human animal (e.g., 8-cell-stage embryo or blastocyst stage embryo), thereby producing chimeric animals carrying each of the above-described MACs, and then offspring animals thereof (Step 10 of FIG. 1). In addition, offspring animals are subjected to crossbreeding to each other to prepare offspring animals carrying the relevant MACs.

By using similar ways to the above, a non-human animal that comprises a mouse artificial chromosome vector comprising the human antibody heavy chain gene or gene locus, the human antibody light chain κ gene or gene locus, and the human antibody light chain λ gene or gene locus (hIGHKL-MAC) can be produced.

The non-human animal that carries a MAC comprising the human antibody heavy chain gene or gene locus derived from human chromosome 14 and the human antibody light chain κ gene or gene locus derived from human chromosome 2, or the non-human animal that carries a MAC comprising the human antibody heavy chain gene or gene locus derived from human chromosome 14 and the human antibody light chain λ gene or gene locus derived from human chromosome 22, is subjected to crossbreeding with a same non-human animal species in which endogenous antibody genes or gene loci that are corresponding to the human antibody heavy chain gene or gene locus and the human antibody light chain κ and λ genes or gene loci have been knocked out, thereby producing: a non-human animal that carries a MAC comprising the human antibody heavy chain gene or gene locus derived from human chromosome 14 and the human antibody light chain κ gene or gene locus derived from human chromosome 2 and in which the endogenous antibody genes or gene loci that are corresponding to the human antibody heavy chain gene or gene locus and the human antibody light chain κ and λ genes or gene loci have been knocked out; or a non-human animal that carries a MAC comprising the human antibody heavy chain gene or gene locus derived from human chromosome 14 and the human antibody light chain λ gene or gene locus derived from human chromosome 22 and in which the endogenous antibody genes or gene loci corresponding to the human antibody heavy chain gene or gene locus and the human antibody light chain κ and λ genes or gene loci have been knocked out.

Alternatively, the non-human animal that carries a MAC comprising the human antibody heavy chain gene or gene locus derived from human chromosome 14 and the human antibody light chain κ gene or gene locus derived from human chromosome 2 and the non-human animal that carries a MAC comprising the human antibody heavy chain gene or gene locus derived from human chromosome 14 and the human antibody light chain λ gene or gene locus derived from human chromosome 22 are subjected to crossbreeding with a same non-human animal species in which endogenous antibody genes or gene loci that are corresponding to the human antibody heavy chain gene or gene locus and the human antibody light chain κ and λ genes or gene loci have been knocked out, thereby producing a non-human animal that carries a MAC comprising the human antibody heavy chain gene or gene locus derived from human chromosome 14 and the human antibody light chain κ gene or gene locus derived from human chromosome 2 and carries a MAC comprising the human antibody heavy chain gene or gene locus derived from human chromosome 14 and the human antibody light chain λ gene or gene locus derived from human chromosome 22, and in which the endogenous antibody genes or gene loci corresponding to the human antibody heavy chain gene or gene locus and the human antibody light chain κ and λ genes or gene loci have been knocked out.

Alternatively, the non-human animal that carries a mouse artificial chromosome vector comprising the human antibody heavy chain gene or gene locus, the human antibody light chain κ gene or gene locus, and the human antibody light chain λ gene or gene locus (hIGHKL-MAC) is subjected to crossbreeding with a same non-human animal species in which endogenous antibody genes or gene loci that are corresponding to the human antibody heavy chain gene or gene locus and the human antibody light chain κ and λ genes or gene loci have been knocked out, thereby producing a non-human animal carrying hIGHKL-MAC in which the endogenous antibody genes or gene loci of the animal have been knocked out.

The procedures described above will be described in more detail.

The term "non-human animal" used herein refers to a mammal other than a human, such as a rodent (e.g., mouse, rat, or guinea pig) or an ungulate (e.g., cattle (or cow) or goat), preferably a rodent, and more preferably rat.

The mouse artificial chromosome vector comprising human antibody genes according to the present invention can be transferred or introduced into any cell. Examples of the method to achieve that goal include microcell fusion, lipofection, a calcium phosphate method, microinjection, and electroporation, preferably microcell fusion.

The microcell fusion technique is a method for transferring a mouse artificial chromosome vector into a desirable cell by microcell fusion between a donor cell (e.g., mouse A9 cell or CHO cell) capable of forming microcells and comprising the mouse artificial chromosome vector and a receptor cell of interest. The cell capable of forming microcells is treated with a polyploid inducer (e.g., colcemid or colchicine) to form multinucleated micronucleate cells, which are then treated with cytochalasin to form microcells, followed by cell fusion of the microcells to a receptor cell of interest.

Examples of receptor cells into which the above mouse artificial chromosome vector can be introduced include animal cells, preferably mammalian cells including human cells, such as germline cells (e.g., oocytes and spermatocytes), stem cells (e.g., embryonic stem (ES) cells, germline stem (GS) cells, somatic stem cells), somatic cells, embryonal cells, adult cells, normal cells, disease cells, primary cultured cells, subcultured cells, and established cell lines. Examples of the stem cells include pluripotent stem cells (e.g., ES cells, embryonic germline (EG) cells, embryonic carcinoma (EC) cells, mGS cells, and human mesenchymal stem cells), induced pluripotent stem (iPS) cells, and nuclear transfer clone embryo-derived embryonic stem (ntES) cells. The preferred cells are selected from the group consisting of somatic cells derived from mammals (preferably rodents including mice and rats), non-human germline cells, stem cells, and precursor cells. When the cell is derived from a mammal such as a rodent, the vector of the present invention is more stably retained in the cell or tissue of the mammal (e.g., a rodent such as a mouse or rat) into which the vector of the present invention has been introduced. That is, drop-out of the vector from the cell is significantly decreased, or the drop-out would not take place.

Examples of cells include hepatocytes, enterocytes, renal cells, splenocytes, lung cells, cardiac cells, skeletal muscle cells, brain cells, bone marrow cells, lymphocytes, megakaryocytes, spermatocytes, and oocytes.

Examples of tissues include liver, intestine, kidney, spleen, lung, heart, skeletal muscle, brain, bone marrow, testis, and ovary tissues.

ES cells can be established and maintained as follows. That is, an inner cell mass is first removed from the blastocyst of a fertilized egg of an animal of interest, and the inner cell mass is then cultured using a mitomycin C-treated mouse embryonic fibroblast as a feeder. Thus, ES cells can be established and maintained (M. J. Evans and M. H. Kaufman, 1981, Nature 292, 154-156).

Induced pluripotent stem (iPS) cell colonies are generated in about 3 to 5 weeks by introducing specific reprogramming factors (DNAs or proteins) into a somatic cell (including a somatic stem cell) and subjecting the cell to culture and subculture in an appropriate medium. Examples of known combinations of reprogramming factors include a combination of Oct3/4, Sox2, Klf4, and c-Myc; a combination of Oct3/4, Sox2, and Klf4; a combination of Oct4, Sox2, Nanog, and Lin28; and a combination of Oct3/4, Sox2, Klf4, c-Myc, Nanog, and Lin28 (K. Takahashi and S. Yamanaka, Cell 126, 663-676, 2006; WO 2007/069666; M. Nakagawa et al., Nat. Biotechnol., 26, 101-106, 2008; K. Takahashi et al., Cell 131, 861-872, 2007; J. Yu et al., Science 318, 1917-1920, 2007; J. Liao et al., Cell Res. 18, 600-603, 2008) For example, culture is conducted using a mitomycin C-treated mouse embryonic fibroblast cell line (e.g., STO) as a feeder cell, and culturing a somatic cell into which the vector has been introduced (approximately $10^4$ to $10^5$ cells/$cm^2$) at about 37° C. using an ES cell culture medium on the feeder cell layer. The feeder cell is not always necessary (Takahashi, K. et al., Cell 131, 861-872, 2007). Examples of the basic medium include Dulbecco's Modified Eagle's Medium (DMEM), Ham's F-12 medium, and a mixture thereof. As the ES cell culture medium, for example, a mouse ES cell culture medium or a primate ES cell culture medium (Reprocell Inc.) can be used.

ES cells and iPS cells are known to contribute to the germline transmission. Accordingly, a non-human animal (or a transgenic animal (excluding a human)) can be generated by a method comprising: introducing the mouse artificial chromosome vector according to the present invention comprising the human antibody gene or gene locus of interest into the ES cells or iPS cells; injecting the cells into the blastocyst of an embryo derived from the same mammalian species as that from which the cells are derived; transplanting the embryo into the uterus of a surrogate mother; and allowing the surrogate mother to give birth to offsprings. In addition, a male and a female of the resulting transgenic animals are subjected to crossbreeding with each other, so that homozygous animals and their offsprings can be further produced.

The human antibody gene or gene locus can be introduced into pluripotent cells, such as ES cells or iPS cells, and other cells described above, via the mouse artificial chromosome vector according to the present invention, thereby producing a human antibody-producing non-human animal.

With regard to the human antibody gene or gene locus comprised in the mouse artificial chromosome vector in such non-human animal, the endogenous genes or gene loci corresponding to the human antibody heavy chain and light chain (κ and λ) genes or gene loci are preferably knocked out (destroyed or deleted). Examples of knockout techniques that can be employed include gene targeting and genome editing using the CRISPR/Cas9 system (e.g., M. Jinek et al., Science 337: 816-821, 2012). A non-human animal in which the endogenous genes have been knocked out and which carries the human antibody gene or gene locus, can be produced by subjecting a chimeric non-human animal that carries a mouse artificial chromosome vector comprising human antibody genes (gene locus) or an offspring thereof to crossbreeding with a chimeric animal or offspring thereof that deletes the entire cluster of corresponding endogenous genes, and further subjecting the resulting animals, which heterozygously delete the endogenous genes, to crossbreeding.

In accordance with the procedures described above, the following cells and animals can be produced: 1) a cell and a transgenic non-human animal that comprises a non-human animal mouse artificial chromosome vector comprising a MAC comprising the human antibody heavy chain gene or gene locus derived from human chromosome 14 and the human antibody light chain κ gene or gene locus derived from human chromosome 2, and in which endogenous antibody genes or gene loci corresponding to the human antibody heavy chain gene or gene locus and the human antibody light chain κ and λ genes or gene loci have been knocked out, 2) a cell and a transgenic non-human animal that comprises a non-human animal mouse artificial chromosome vector comprising a MAC comprising the human antibody heavy chain gene or gene locus derived from human chromosome 14 and the human antibody light chain λ gene or gene locus derived from human chromosome 22, and in which endogenous antibody genes or gene loci corresponding to the human antibody heavy chain gene or gene locus and the human antibody light chain κ and λ genes or gene loci have been knocked out, 3) a cell and a transgenic non-human animal that comprises a non-human animal mouse artificial chromosome vector comprising a MAC comprising the human antibody heavy chain gene or gene locus derived from human chromosome 14 and the human antibody light chain κ gene or gene locus derived from human chromosome 2, and a MAC comprising the human antibody heavy chain gene or gene locus derived from human chromosome 14 and the human antibody light chain λ gene or gene locus derived from human chromosome 22, and in which endogenous antibody genes or gene loci corresponding to the human antibody heavy chain gene or gene locus and the human antibody light chain κ and λ genes or gene loci have been knocked out, or 4) a cell and a transgenic non-human animal that comprises a non-human animal mouse artificial chromosome vector comprising a MAC comprising the human antibody heavy chain gene or gene locus derived from human chromosome 14, the human antibody light chain κ gene or gene locus derived from human chromosome 2, and the human antibody light chain λ gene or gene locus derived from human chromosome 22, and in which endogenous antibody genes or gene loci corresponding to the human antibody heavy chain gene or gene locus and the human antibody light chain κ and λ genes or gene loci have been knocked out. Examples of the non-human animals are rodents, such as mouse and rat, that carry the mouse artificial chromosome vector.

It may occasionally be impossible to prepare a transgenic rat capable of producing a human antibody in accordance with the method described above. The methods (A), (B), and (C) described below are alternatives to the methods described above.

(A) Preparation of Rat ES Cells (Male Lineage)

As with the case of mouse ES cells (M. J. Evans and M. H. Kaufman, Nature 1981; 292 (5819): 154-156), rat ES cells are established from the inner cell mass of the rat blastocyst stage embryo or 8-cell-stage embryo, and are pluripotent and self-reproducible cell lines. For example, rat blastocysts with egg zona pellucida dissolved are cultured on mouse embryonic fibroblast (MEFF) feeder using a medium containing leukemia inhibitory factor (LIF), the outgrowth formed from the blastocysts is dispersed 7 to 10 days later and is then transferred to MEF feeder and cultured on the feeder. After 7 days, the ES cells appear. Preparation of rat ES cells is described in, for example, K. Kawaharada et al., World J. Stem Cells 2015; 7(7): 1054-1063.

ES cells are classified into female cell lines and male cell lines. In the present invention, use of male rat ES cells is preferable, and use of male rat ES cells prepared from hybrid rats is more preferable. Using such ES cells and the ROSI technique and the fluorescence selection, rat models transmittable to offsprings can be obtained. Male ES cells can be selected by analyzing the XY karyotype of the prepared ES cell lines using a XY chromosome probe (e.g., available from Chromosome Science Labo Inc.). The term "male ES cell" or "ES cell (male lineage)" used herein refers to an ES cell having the XY karyotype.

The induced pluripotent stem (iPS) cells described above are known as stem cells similar to ES cells, and rat iPS cells (W. Li et al., Cell Stem Cell 2009; 4: 16-19; S. Hamanaka et al., PLoS One 2011; 6: e22008) can be used as the alternative to ES cells.

(B) Microcell Fusion (MMCT)

As described above, the microcell fusion technique enables transfer of a macronucleic acid of appropriately 0.9 Mg or larger, such as a single or a small number of chromosomes or a fragment thereof (herein, a chromosome or a fragment thereof, comprising the human antibody heavy chain gene or gene locus, the human antibody light chain κ gene or gene locus, or the human antibody light chain λ gene or gene locus), from a donor cell to a recipient cell. This technique comprises: Step 1 of converting donor cells into micronucleated cells; Step 2 of denucleating the micronucleated cells; Step 3 of isolating microcells; Step 4 of fusing the microcells to recipient cells; and Step 5 of selecting viable microcell hybrid clones.

MMCT is described in more detail, in addition to the above.

Donor cells can be converted into micronucleated cells by culture of animal cells in a medium containing a microcell inducer, such as colcemid, for a long period of time. The microcells inducer is capable of inducing decondensation of chromosomes and reconstitution of nuclear membranes. The concentration of a microcell inducer is not limited as long as the microcell formation occurs. In the case of colcemid, for example, the concentration of a microcell inducer is about 0.01 μg/ml to about 1 μg/ml, and preferably 0.05 to 0.5 μg/ml, relative to about $5\times10^6$ recipient cells. As a result of the microcell formation, microcell-containing cells that comprise a small amount of cytoplasm and one (1) or a small number of chromosomes, that is, microcells, are formed from donor cells. Culture is conducted under culture conditions for donor cells, and the culture media for animal cells are generally used. Examples of animal cell culture media include Eagle's Medium (MEM), Eagle's minimum essential medium (EMEM), Dulbecco's Modified Eagle's Medium (DMEM), and Ham's F12 medium. Media may be supplemented with, for example, fetal bovine serum (FBS) or a fetal bovine serum replacement (e.g., StemSure® Serum Replacement). Temperature is from room temperature to about 37° C., and an appropriate culture period is about 40 to 80 hours.

Micronucleated cells are denucleated using cytochalasin B. A culture solution containing the micronucleated cells is put in a centrifuge tube, cytochalasin B is added at a concentration of approximately 10 μg/ml, and centrifugation is carried out at 34° C. and approximately 11,900×g. The precipitated microcells are suspended in a serum-free medium and then recovered or collected. Microcells can be purified by ultrafiltration. Three types of membranes with pore diameters of 8 μm, 5 μm, and 3 μm are prepared, and the microcells are filtered through the filters in order.

Fusion between microcells and recipient cells is carried out by layering purified microcells on the recipient cells whose culture was terminated before complete confluency, followed by culturing the layered cells. Microcell-fused cells can be selected by, for example, a method for selecting drug resistant cell lines.

Such fusion can be carried out by techniques, such as the polyethylene glycol (PEG) method, the retro method (T. Suzuki et al., PLOS ONE, DOI: 10.1371/journal.pone.0157187, 2016), or the MV method (M. Katoh et al., BMC Biotechnology 2010, 10: 37). According to the retro method, the fusion between microcells and recipient cells is carried out using ecotropic or amphotropic MLV-derived R-peptide-deleted Env (EnvAR). This method gives the highest efficiency in rodent cells. According to the MV method, the microcell fusion is accelerated using a hemagglutinin protein (MV-H), which is measles virus fusogen, and a fusion protein (MV-F). Microcells prepared from donor cells that have been transformed with MV-H plasmid and MV-F plasmid in advance, easily cause the cell-cell fusion to recipient cells, because of the presence of fusogen expressed on the cell membrane surface.

Preferably, the above-described human chromosomes or fragments thereof, which are exogenous nucleic acids, are introduced in advance into donor cells. In such a case, the human chromosomes migrate to microcells and are introduced into recipient cells by microcell fusion. As a result, the recipient cells are transformed by the human chromosomes.

(C) Round Spermatid Injection (ROSI)

The round spermatid injection (ROSI) method comprises cutting the seminiferous tubule removed from the testis of the chimera rat (male) into pieces, preparing a suspension of the cut seminiferous tubule, suctioning the round spermatid into a pipette, separating the nuclei and the cytoplasm from each other in the pipette, injecting the resultant into a rat oocyte, and performing micro-insemination (C. Tsurumaki et al., J. Mamm. Ova Res., 2009; 26: 86-93 (Jp)). In addition, the impregnated oocyte is transplanted into the uterus of a surrogate mother, allowing the surrogate mother to give birth to chimera rats, and subjecting a female rat (or a male rat) carrying the human antibody genes or gene loci to crossbreeding with a pure or hybrid (preferably a hybrid) male rat (or a female rat). Thus, a rat carrying the human antibody genes or gene loci in various rat tissues can be obtained.

Instead of the ROSI method, oocyte and sperm can also be subjected to micro-insemination by intracytoplasmic sperm injection (ICSI).

In summary, the non-human animal according to the present invention includes the animals described below.

1) A non-human animal comprising a mouse artificial chromosome comprising a human antibody heavy chain gene or gene locus and a human antibody light chain κ gene or gene locus (hIGHK-MAC).
2) A non-human animal comprising a mouse artificial chromosome comprising a human antibody heavy chain gene or gene locus and a human antibody light chain λ gene or gene locus (hIGHL-MAC).
3) A non-human animal comprising a mouse artificial chromosome comprising a human antibody heavy chain gene or gene locus and a human antibody light chain κ gene or gene locus (hIGHK-MAC) and a mouse artificial chromosome comprising a human antibody heavy chain gene or gene locus and a human antibody light chain λ gene or gene locus (hIGHL-MAC).
4) A non-human animal comprising a mouse artificial chromosome comprising a human antibody heavy chain gene or gene locus, a human antibody light chain κ gene or gene locus, and a human antibody light chain λ gene or gene locus (hIGHKL-MAC).
5) A non-human animal which comprises a mouse artificial chromosome comprising a human antibody heavy chain gene or gene locus and a human antibody light chain κ gene or gene locus (hIGHK-MAC), and in which endogenous antibody genes or gene loci corresponding to the human antibody heavy chain gene or gene locus and the human antibody light chain κ and λ genes or gene loci have been knocked out.
6) A non-human animal which comprises a mouse artificial chromosome comprising a human antibody heavy chain gene or gene locus and a human antibody light chain λ gene or gene locus (hIGHL-MAC), and in which endogenous antibody genes or gene loci corresponding to the human antibody heavy chain gene or gene locus and the human antibody light chain κ and λ genes or gene loci have been knocked out.
7) A non-human animal which comprises a mouse artificial chromosome comprising a human antibody heavy chain gene or gene locus and a human antibody light chain κ gene or gene locus (hIGHK-MAC) and a mouse artificial chromosome comprising a human antibody heavy chain gene or gene locus and a human antibody light chain λ gene or gene locus (hIGHL-MAC), and in which endogenous antibody genes or gene loci corresponding to the human antibody heavy chain gene or gene locus, the human antibody light chain κ gene or gene locus, and the human antibody light chain λ gene or gene locus have been knocked out.
8) A rat which comprises a mouse artificial chromosome comprising a human antibody heavy chain gene or gene locus, a human antibody light chain κ gene or gene locus, and a human antibody light chain λ gene or gene locus (hIGHKL-MAC), and in which endogenous antibody genes corresponding to the human antibody heavy chain gene or gene locus, the human antibody light chain κ gene or gene locus, and the human antibody light chain λ gene or gene locus have been knocked out.

Examples of the non-human animals include mammals, such as rodents and ungulates, and birds. Examples of rodents include mice, rats, and hamsters. Examples of ungulates include cattles (or cows) and goat. Examples of birds include poultries (e.g., chickens). Preferable non-human animals are mice, rats, and cattles (or cows), preferably rats.

Methods for producing a non-human animal capable of producing a human antibody include the methods described below.

1) A method for producing a non-human animal capable of producing a human antibody comprising: crossbreeding a non-human animal comprising a mouse artificial chromosome that comprises a human antibody heavy chain gene or gene locus and a human antibody light chain κ gene or gene locus (hIGHK-MAC), with a same non-human animal species in which endogenous antibody genes or gene loci corresponding to the human antibody heavy chain gene or gene locus and the human antibody light chain κ gene or gene locus have been knocked out; and selecting a non-human animal that comprises hIGHK-MAC and in which the endogenous antibody genes or gene loci corresponding to the human antibody heavy chain gene or gene locus and the human antibody light chain κ and λ genes or gene loci have been knocked out.

2) A method for producing a non-human animal capable of producing a human antibody comprising: crossbreeding a non-human animal comprising a mouse artificial chromosome that comprises a human antibody heavy chain gene or gene locus and a human antibody light chain λ gene or gene locus (hIGHL-MAC), with a same non-human animal species in which endogenous antibody genes or gene loci corresponding to the human antibody heavy chain gene or gene locus and the human antibody light chain κ and λ genes or gene loci have been knocked out; and selecting a non-human animal that comprises hIGHL-MAC and in which the endogenous antibody genes or gene loci have been knocked out.

3) A method for producing a non-human animal capable of producing a human antibody comprising: crossbreeding a non-human animal comprising a mouse artificial chromosome that comprises a human antibody heavy chain gene or gene locus and a human antibody light chain κ gene or gene locus (hIGHK-MAC), with a non-human animal comprising a mouse artificial chromosome that comprises a human antibody heavy chain gene or gene locus and a human antibody light chain λ gene or gene locus (hIGHL-MAC), thereby producing a non-human animal comprising hIGHK-MAC and hIGHL-MAC; crossbreeding the produced non-human animal with a same non-human animal species in which endogenous antibody genes or gene loci corresponding to the human antibody heavy chain gene or gene locus, the human antibody light chain κ gene or gene locus, and the human antibody light chain λ gene or gene locus have been knocked out; and selecting a non-human animal that comprises hIGHK-MAC and hIGHL-MAC and in which the endogenous antibody genes or gene loci have been knocked out.

4) A method for producing a non-human animal capable of producing a human antibody comprising: crossbreeding a non-human animal that comprises a mouse artificial chromosome comprising a human antibody heavy chain gene or gene locus and a human antibody light chain κ gene or gene locus (hIGHK-MAC) and in which endogenous antibody genes or gene loci corresponding to the human antibody heavy chain gene or gene locus and the human antibody light chain κ and λ genes or gene loci have been knocked out, with a non-human animal that comprises a mouse artificial chromosome comprising a human antibody heavy chain gene and a human antibody light chain λ gene or gene locus (hIGHL-MAC) and in which endogenous antibody genes or gene loci corresponding to the human antibody heavy chain gene and the human antibody light chain κ and λ genes or gene loci have been knocked out; and selecting a non-human animal that comprises hIGHK-MAC and hIGHL-MAC and in which the endogenous antibody genes or gene loci have been knocked out.

5) A method for producing a non-human animal capable of producing a human antibody comprising: crossbreeding a non-human animal that comprises a mouse artificial chromosome comprising a human antibody heavy chain gene or gene locus, a human antibody light chain κ gene or gene locus, and a human antibody light chain λ gene or gene locus (hIGHKL-MAC), with a sames non-human animal species in which endogenous antibody genes corresponding to the human antibody heavy chain gene or gene locus, the human antibody light chain κ gene or gene locus, and the human antibody light chain λ gene or gene locus have been knocked out; and selecting a non-human animal that comprises hIGHKL-MAC and in which the endogenous antibody genes or gene loci have been knocked out.

2. Production of Human Antibody

The present invention provides a method for producing a human antibody comprising: administering an antigen substance to the above-described non-human animal; and collecting the produced human antibody binding to the antigen substance.

According to the method described above, the antibody can be collected by a column chromatography technique comprising: applying an anti-serum containing the antibody to a column filled with a support (e.g., agarose gel or silica gel) bound to the antigen substance; and eluting the human antibody bound to the support from the support.

The present invention also provides a method for producing a human monoclonal antibody comprising: a step of administering an antigen substance to the above-described non-human animal; a step of removing spleen cells from the spleen of the non-human animal; a step of fusing the spleen cells to myeloma cells to produce hybridomas; and a step of collecting the antibody binding to the antigen substance from the hybridomas.

The human monoclonal antibody can be purified by the column chromatography technique as described above.

In general, the antigen substance is a cell, protein, polypeptide, or peptide. At present, human antibodies are used as therapeutic drugs for cancer, osteoporosis, rheumatic arthritis, and the like. In addition, many other human antibodies are under clinical studies as therapeutic agents for hypercholesterolemia, autoimmune diseases, inflammatory diseases, tumors, allergic diseases, aches, cardiovascular diseases, metabolic disorders, and the like. Such antigen substances are exemplified in Non-Patent Literature 1. An example of the cells as antigen substances is tumor cells. The present invention is applicable to many antigensubstances including the antigen substances as described above.

EXAMPLES

The present invention is described in more detail with reference to the following examples, although the scope of the present invention is not limited to these examples. Production of human antibody-producing mice and rats is summarized (FIG. 1).

Example 1

Modification of Human Chromosome 2

Figure 2:
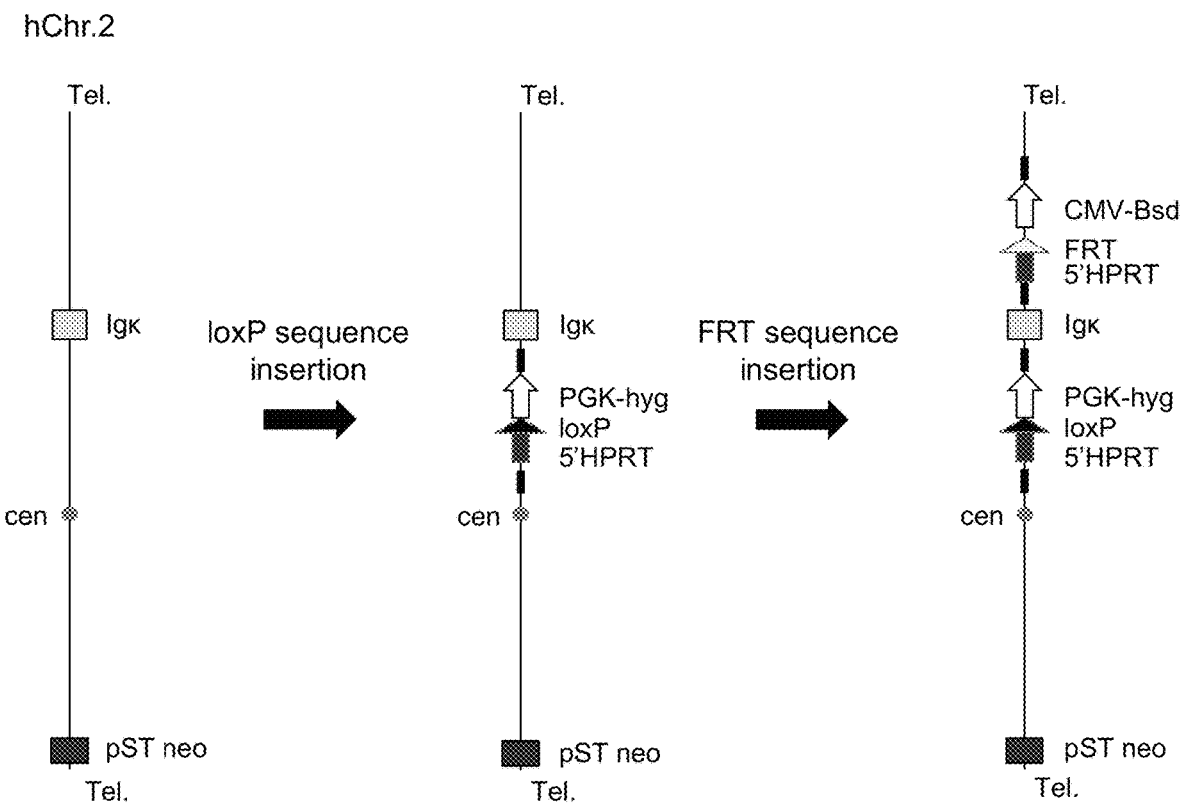
FIG. 2 shows modification of human chromosome 2 comprising inserting a loxP sequence into a region on the centromere (cen) side of the light chain κ gene of human chromosome 2 and inserting an FRT sequence into a region on the telomere (Tel) side of the same gene.

In order to clone IGK and IGH regions into the mouse artificial chromosome vector (MAC) by translocation, recombinant sequences; i.e., the loxP sequence and the FRT sequence, are introduced into human chromosome 2 (FIG. 2).

[A] Insertion of loxP Sequence into Human Chromosome 2

In order to clone the IGK region of the human chromosome 2 into the mouse artificial chromosome vector (MAC) by reciprocal translocation using the Cre/Lox system, the loxP sequence is inserted into human chromosome 2 in the chicken DT40 cells exhibiting high frequency of homologous recombination.

[A.1] Preparation of Vector for loxP Insertion into Human Chromosome 2

As a basic plasmid used for inserting the loxP sequence into the DT40 521D4(#2) cells carrying human chromosome 2, v901 (Lexicon genetics) was used. The DNA sequence of human chromosome 2 as a loxP insertion site was obtained from the GenBank database (NC_000002.12).

Genomic DNA extracted from DT40 (#2) was used as a template, and the target sequence of homologous recombination was amplified using primer sequences shown below.

cos138-F6B:
(SEQ ID NO: 1)
5'-TCGAGGATCCCACATAGACATTCAACCGCAAAGCAG-3' cos138-R6B:
(SEQ ID NO: 2)
5'-TCGAGGATCCAGGCCCTACACATCAAAAAGTGAAGCA-3'

PCR was carried out using TP600 thermal cycler (Takara, Kyoto, Japan), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 12 minutes was conducted for 30 cycles. The PCR product was digested with BamHI (NEB), separated and purified by agarose gel electrophoresis, and cloned into the v901 BamHI site (vector name: v901-cos138). In order to confirm cloning of the target sequence, the vector was digested with EcoRV (NEB), BglII (NEB), and AvrII (NEB) restriction enzymes and subjected to electrophoresis, followed by sequence analysis.

As a basic plasmid of a cassette containing PGKhygro, loxP, and PGK HPRT exons 1-2, v913 (Lexicon genetics) was used. Concerning 5'HPRT-loxP, the oligo-synthesized loxP sequence was cloned into the XbaI site of V820 (Lexicon genetics). 5'HPRT-loxP was cloned into ClaI and AscI of V907 (Lexicon genetics), and PGKhygro was cloned into the ClaI and KpnI sites (vector name: pX6.1).

Figure 3:
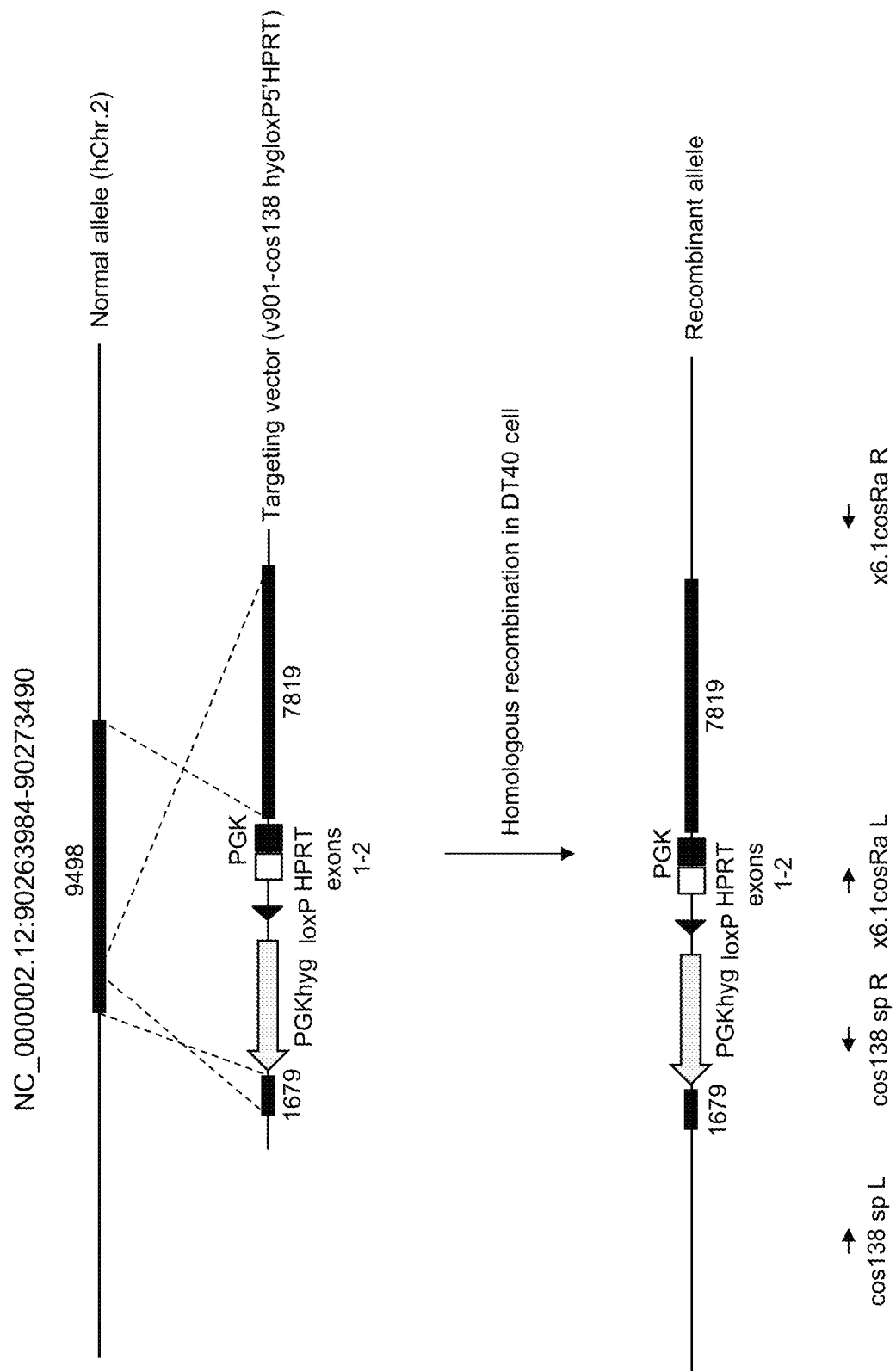
FIG. 3 shows production of a loxP-carrying recombinant allele obtained by modifying the alle of human chromosome 2 by homologous recombination using a targeting vector indicated therein.

PGKhygro-loxP-PGK HPRT exons 1-2 of pX6.1 was digested with KpnI (NEB) and AscI (NEB), the product was blunt-ended with the Blunting high kit (TOYOBO), and the SpeI site of v901-cos138 was blunt-ended with the Blunting high kit, followed by ligation (vector name: v901-cos138 hygloxP5'HPRT). FIG. 3 shows the targeting vector, the target sequence, and the chromosome allele resulting from homologous recombination.

[A.2] Insertion of loxP into Human Chromosome 2 in Chicken DT40 Cell

Chicken DT40 cells were cultured in RPMI 1640 culture medium (Gibco) supplemented with 10% fetal bovine serum (hereafter abbrebyted as FBS, Gibco), 1% chicken serum (Gibco), and 10-4 M 2-mercaptoethanol (Sigma). Approximately $10^7$ DT40 (#2) cells were washed once with additive-free RPMI 1640 culture medium and suspended in 0.5 ml of additive-free RPMI 1640 culture medium. The targeting vector v901-cos138 hygloxP5'HPRT (25 μg) linearized with the restriction enzyme NotI (NEB) was added thereto, then transferred into a cuvette (Bio-Rad Laboratories, Inc.) for electroporation, and the cuvette was allowed to stand at room temperature for 10 minutes. The cuvette was set on Gene Pulser (Bio-Rad Laboratories, Inc.) and voltage was applied under the conditions of 550 V and 25 μF. The cuvette was allowed to stand at room temperature for 10 minutes, the cell suspension was dispensed to twelve 96-well culture plates, and culture was then conducted for 24 hours. The culture medium was exchanged with a culture medium containing Hygromycin (1.5 mg/ml) (Wako, Osaka, Japan) and then subjected to selection culture for about 2 weeks. As a result of the reactions repeated 5 times, 191 drug-resistant cell lines were obtained, and 44 clones selected at random were subjected to the subsequent analysis.

[A.3] Selection of Homologous Recombinant

For extraction of genomic DNA from the hygromycin-resistant cell line and use thereof as a template for selection of a recombinant, PCR was carried out using the primers shown below, and whether or not site-directed recombination had occurred on human chromosome 2 was confirmed. The primer sequences are shown below.

(SEQ ID NO: 3)
cos138 sp L: 5'-CTGAGAAGAGTCATTGTTTATGGTAGACT-3'

(SEQ ID NO: 4)
cos138 sp R: 5'-ATCCCCATGTGTATCACTGGCAAACTGT-3'

(SEQ ID NO: 5)
x6.1cosRa L: 5'-GGGGAATAAACACCCTTTCCAAATCCTC-3'

(SEQ ID NO: 6)
x6.1cosRa R: 5'-ACCAAGTAACCGATCAAACCAACCCTTG-3'

When using the primers cos138 sp L and cos138 sp R, PCR was carried out using Accuprime Taq DNA polymerase (Thermo Fisher Scientific) and buffers and dNTPs (dATP, dCTP, dGTP, and dTTP) included in the kit under the recommended conditions. Temperature and cycle conditions were as follows: after thermal denaturation at 94° C. for 2 minutes, the cycle of 94° C. for 15 seconds, 60° C. for 15 seconds, and 68° C. for 5 minutes was conducted for 35 cycles.

When using the primers x6.1cosRa L and x6.1cosRa R, PCR was carried out using KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 12 minutes was conducted for for 30 cycles.

In addition, whether or not a region of interest on human chromosome 2 was retained was confirmed using the primers shown below. The primer sequences are shown below.

```
                                              (SEQ ID NO: 7)
D2S177 F: 5'-AGCTCAGAGACACCTCTCCA-3'

(SEQ ID NO: 8)
D2S177 R: 5'-CTGTATTAGGATACTTGGCTATTGA-3'

(SEQ ID NO: 9)
FABP1-F: 5'-TATCAAGGGGGTGTCGGAAATCGTG-3'

(SEQ ID NO: 10)
FABP1-R: 5'-ACTGGGCCTGGGAGAACCTGAGACT-3'

(SEQ ID NO: 11)
EIF2AK3-F: 5'-AGGTGCTGCTGGGTGGTCAAGT-3'

(SEQ ID NO: 12)
EIF2AK3-R: 5'-GCTCCTGCAAATGTCTCCTGTCA-3'

(SEQ ID NO: 13)
RPIA-F: 5'-CTTACCCAGGCTCCAGGCTCTATT-3'

(SEQ ID NO: 14)
RPIA-R: 5'-CTCTACCTCCCTACCCCATCATCAC-3'

(SEQ ID NO: 15)
IGKC-F: 5'-TGGAAGGTGGATAACGCCCT-3'

(SEQ ID NO: 16)
IGKC-R: 5'-TCATTCTCCTCCAACATTAGCA-3'

(SEQ ID NO: 17)
IGKV-F: 5'-AGTCAGGGCATTAGCAGTGC-3'

(SEQ ID NO: 18)
IGKV-R: 5'-GCTGCTGATGGTGAGAGTGA-3'

(SEQ ID NO: 19)
Vk3-2 F: 5'-CTCTCCTGCAGGGCCAGTCA-3'

(SEQ ID NO: 20)
Vk3-2 R: 5'-TGCTGATGGTGAGAGTGAACTC-3'

(SEQ ID NO: 21)
D2S159_1 F: 5'-CTCTAACTGAATCAAGGGAATGAAC-3'

(SEQ ID NO: 22)
D2S159_1 R: 5'-AGCAGTTTGAGTTTAGGATGAAGG-3'
```

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

As a result of PCR, 3 clones found to be positive were subjected to the subsequent analysis.

[A.4] Two-Color FISH Analysis

Figure 4:
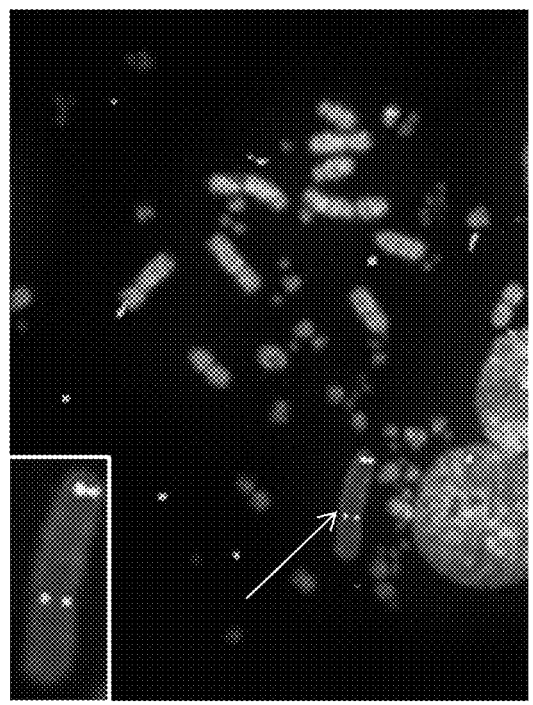
FIG. 4 is a figure obtained by two-color FISH analysis indicating site-directed insertion of PGKhygloxP5'HPRT (indicated by an arrow) into human chromosome 2.

On the basis of the above results, the 3 clones were subjected to two-color FISH analysis according to Matsubara et al. (FISH experimental protocol, Shujunsha Co., Ltd., 1994). FISH analysis was carried out using Human cot-1 DNA and pX6.1 as probes. As a result, one copy of human chromosome 2 was retained and aPGKhygloxP5'HPRT-derived signal was observed in all the 3 clones (at 100%), but no signal was detected on human chromosome 2 as a negative control before site-directed insertion of PGKhygloxP5'HPRT. Thus, site-directed insertion of PGKhygloxP5'HPRT was confirmed (FIG. 4). The 2 clones 521D4 loxP1-28 and 521D4 loxP4-6 were selected from among the 3 clones and subjected to the subsequent experiment.

[B] Insertion of FRT Site in Human Chromosome 2 Carrying loxP

For cloning of the IGK region of the human chromosome 2 and the IGH region of the human chromosome 14 into MAC with the aid of loxP by translocation, the FRT site is inserted into human chromosome 2 into which loxP has been inserted.

[B.1] Preparation of Vector for FRT Insertion into Human Chromosome 2

As a basic plasmid for inserting the FRT sequence into DT40 (#2), pMA-RQ (Life technologies) was used. An artificial gene synthesizing sequence (PGK5'HPRTFRT, Life technologies) was cloned into the vector (vector name: pMA-kD9FRT). At the outset, pCMV/Bsd (Invitrogen) was digested with XhoI and EcoRI and electrophoresed. Thereafter, the CMVBsd sequence was subjected to gel extraction, and the resultant was ligated to the protruding end formed by digestion of pMA-kD9FRT with EcoRI and XhoI (vector name: pMA-kD9FRTBsd).

The DNA sequence of human chromosome 2 as an FRT insertion site was obtained from the GenBank database (NC_000002.12). Genomic DNA was extracted from DT40 (#2) and used as a template to amplify the target sequence of homologous recombination. The primer sequences used are shown below.

```
kD-R9La L:
                                              (SEQ ID NO: 23)
5'-TCGAGCGGCCGCAGGATCTTTGGGGGACTGAATGGGGTGTGCT-3' kD-R9La R:
                                              (SEQ ID NO: 24)
5'-TCGAACGCGTTGGAACCCTCATACGTTGCTGGTGGAATGT-3'

KD-F9Ra L:
                                              (SEQ ID NO: 25)
5'-CGAGGATCCATTTCTCCACATCCTAGCCAACACTTGACATTTCCT-3'

KD-F9Ra R:
                                              (SEQ ID NO: 26)
5'-TCGAGGATCCGCCAGGGAGACAGATGCCAAGTACGGTTTAG-3'
```

When using the primers kD-R9La L and kD-R9La R, PCR was carried out using KOD FX (TOYOBO) and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 2.5 minutes was conducted for 30 cycles. The resulting PCR product was digested with NotI (NEB) and MluI (NEB), electrophoresed, subjected to gel extraction, and then ligated to the protruding end formed by digestion of pMA-kD9FRTBsd with NotI and MluI (vector name: pMA-kD9FRTL).

Figure 5:
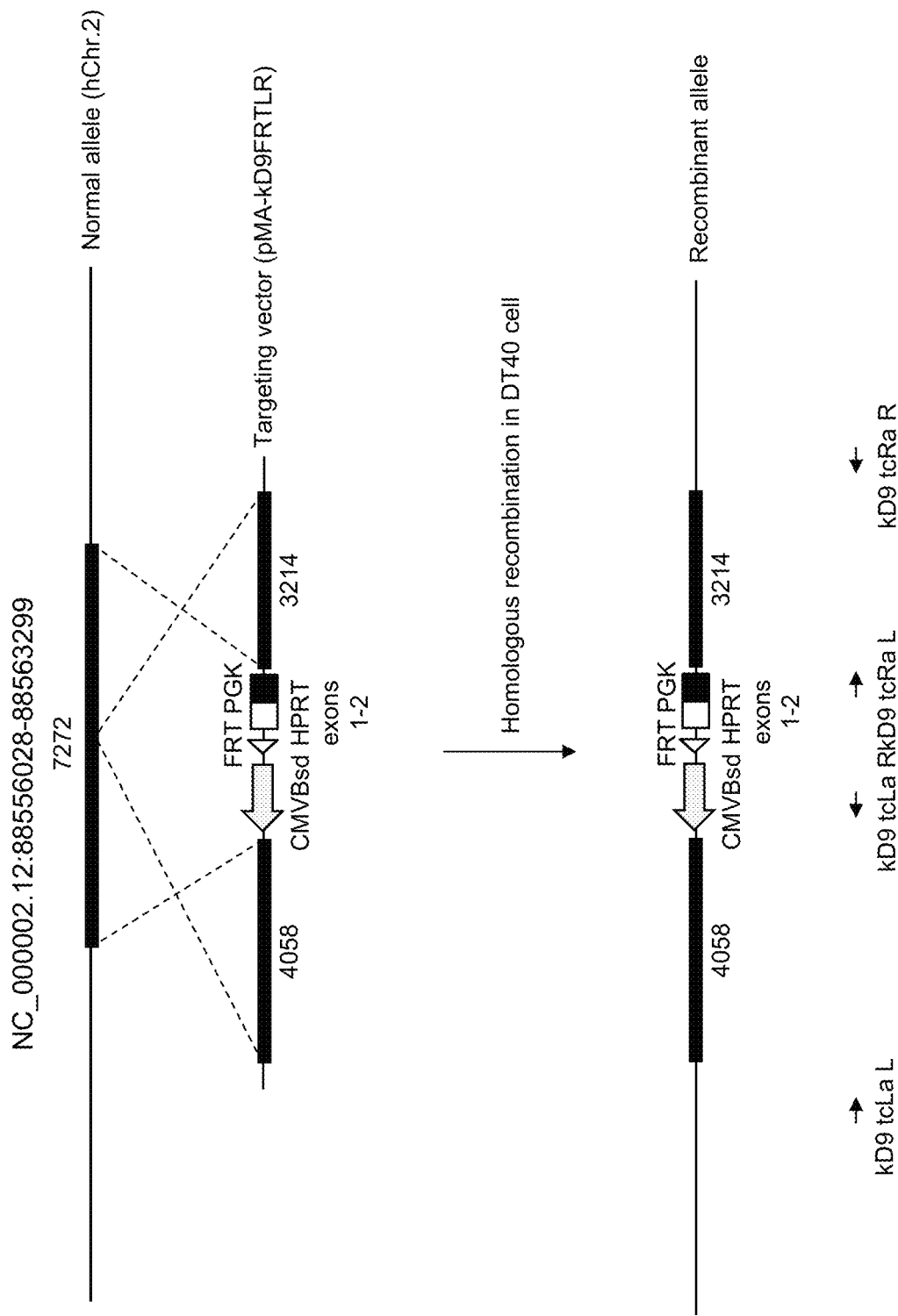
FIG. 5 shows a procedure of inserting the FRT site into the human chromosome 2 allele by homologous recombination using a targeting vector indicated.

When using the primers KD-F9Ra L and KD-F9Ra R, PCR was carried out using KOD FX (TOYOBO) and buffers and dNTPs (dATP, dCTP, dGTP, and dTTP) included in the kit under the recommended conditions. Temperature and cycle conditions were as follows: thermal denaturation at 98° C. for 1 minute was followed by 30 cycles of 98° C. for 15 seconds and 68° C. for 2.5 minutes. The resulting PCR product was digested with BamHI and cloned into the BamHI site of pMA-kD9FRTL (vector name: pMAkD9FRTLR). FIG. 5 shows the targeting vector, the target sequence, and the chromosome allele obtained by homologous recombination.

[B.2] Insertion of FRT into loxP-Carrying Human Chromosome 2 in Chicken DT40 Cell Chicken DT40 cells were cultured in RPMI 1640 culture medium (Gibco) supplemented with 10% FBS, 1% chicken serum (Gibco), and 10-4M 2-mercaptoethanol (Sigma). Approximately $10^7$ DT40 (#2) cells, i.e., 521D4 loxP1-28 and 521D4 loxP4-6 cells, were washed once with additive-free RPMI 1640 culture medium and suspended in 0.5 ml of additive-free RPMI 1640 culture medium. The targeting vector pMA-kD9FRTLR (25 μg) linearized with the restriction enzyme NotI (NEB) was added thereto, the resultant was transferred into a cuvette (Bio-Rad Laboratories, Inc.) for electroporation, and the cuvette was allowed to stand at room temperature for 10 minutes. The cuvette was set on Gene Pulser (Bio-Rad Laboratories, Inc.) and voltage was applied under the conditions of 550 V and 25 μF. The cuvette was allowed to stand at room temperature for 10 minutes, the cell suspension was dispensed to twelve 96-well culture plates, and culture was then conducted for 24 hours. Drug selection was carried out with the aid of 15 μg/ml blasticidin (Funakoshi). As a result of the reactions repeated 3 times, 86 and 82 drug resistant clones were obtained from 521D4 loxP1-28 and 521D4 loxP4-6, respectively, 24 clones were selected at random from both thereof, and genomic DNAs were extracted therefrom. In order to select recombinants with the use thereof as templates, PCR was carried out using the primers shown below, and whether or not site-directed recombination had occurred in human chromosome 2 was examined. The primer sequences are shown below.

```
                                             (SEQ ID NO: 27)
kD9 tcLa L:  5'-TGAGAACACAGGGGTCTCCATTCTGACT-3'

(SEQ ID NO: 28)
kD9 tcLa R:  5'-ACAATCAACAGCATCCCCATCTCTGAAG-3'

(SEQ ID NO: 29)
kD9 tcRa L:  5'-GACGTGCTACTTCCATTTGTCACGTCCT-3'

(SEQ ID NO: 30)
kD9 tcRa R:  5'-TGGTCACTGAAGCTTTCCATCTGCTCTT-3'
```

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

In addition, the loxP sequence and the human chromosome 2 regions were confirmed by PCR. The primers are shown below.

Primers for Confirmation of loxP Sequence on Human Chromosome 2 cos138 sp L (described above)
cos138 sp R (described above)
x6.1cosRa L (described above)
x6.1cosRa R (described above)

When using the primers cos138 sp L and cos138 sp R, PCR was carried out using Accuprime Taq DNA polymerase (Thermo Fisher Scientific) and buffers and dNTPs (dATP, dCTP, dGTP, and dTTP) included in the kit under the recommended conditions. Temperature and cycle conditions were as follows: after thermal denaturation at 94° C. for 2 minutes, the cycle of 94° C. for 15 seconds, 60° C. for 15 seconds, and 68° C. for 5 minutes was conducted for 35 cycles.

When using the primers x6.1cosRa L and x6.1cosRa R, PCR was carried out using KOD FX (TOYOBO) and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 12 minutes was conducted for 30 cycles. In addition, PCR analysis was carried out to confirm the human chromosome 2 region. The primer sequences are shown below.

D2S177 F (described above)
D2S177 R (described above)
FABP1-F (described above)
FABP1-R (described above)
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)
D2S159_1 F (described above)
D2S159_1 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

As a result, 7 positive clones and 3 positive clones were obtained from 521D4 loxP1-28 and 521D4 loxP4-6, respectively.

[B.3] Two-Color FISH Analysis

Figure 6:
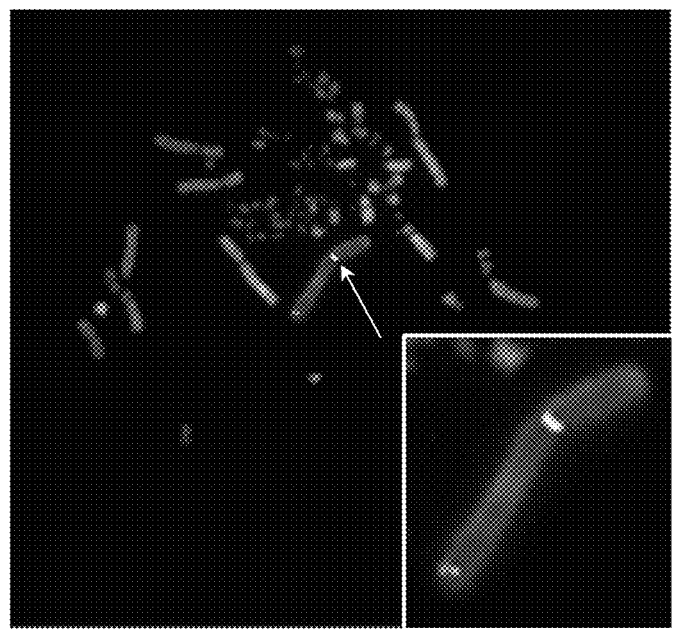
FIG. 6 is a figure obtained by two-color FISH analysis indicating retention of a copy of human chromosome 2 and insertion of PGK5'HPRTFRTBsd (indicated by an arrow).

On the basis of the above results, the 7 clones and the 3 clones were subjected to two-color FISH analysis according to Matsubara et al. (FISH experimental protocol, Shujunsha Co., Ltd., Tokyo, Japan, 1994). FISH analysis was carried out using Human cot-1 DNA and pMA-kD9FRTBsd as probes. As a result, one copy of human chromosome 2 was retained and PGK5'HPRTFRTBsd-derived signal was observed in 87% or more of all the clones, but no signal was detected on human chromosome 2 as a negative control before site-directed insertion of PGK5'HPRTFRTBsd. Thus, site-directed insertion of PGK5'HPRTFRTBsd was confirmed (FIG. 6). The two clones 521D4 loxP1-28 FRT1-23 and 521D4 loxP4-6 FRT1-15 were selected therefrom and subjected to the subsequent experiment.

Example 2

Figure 7:
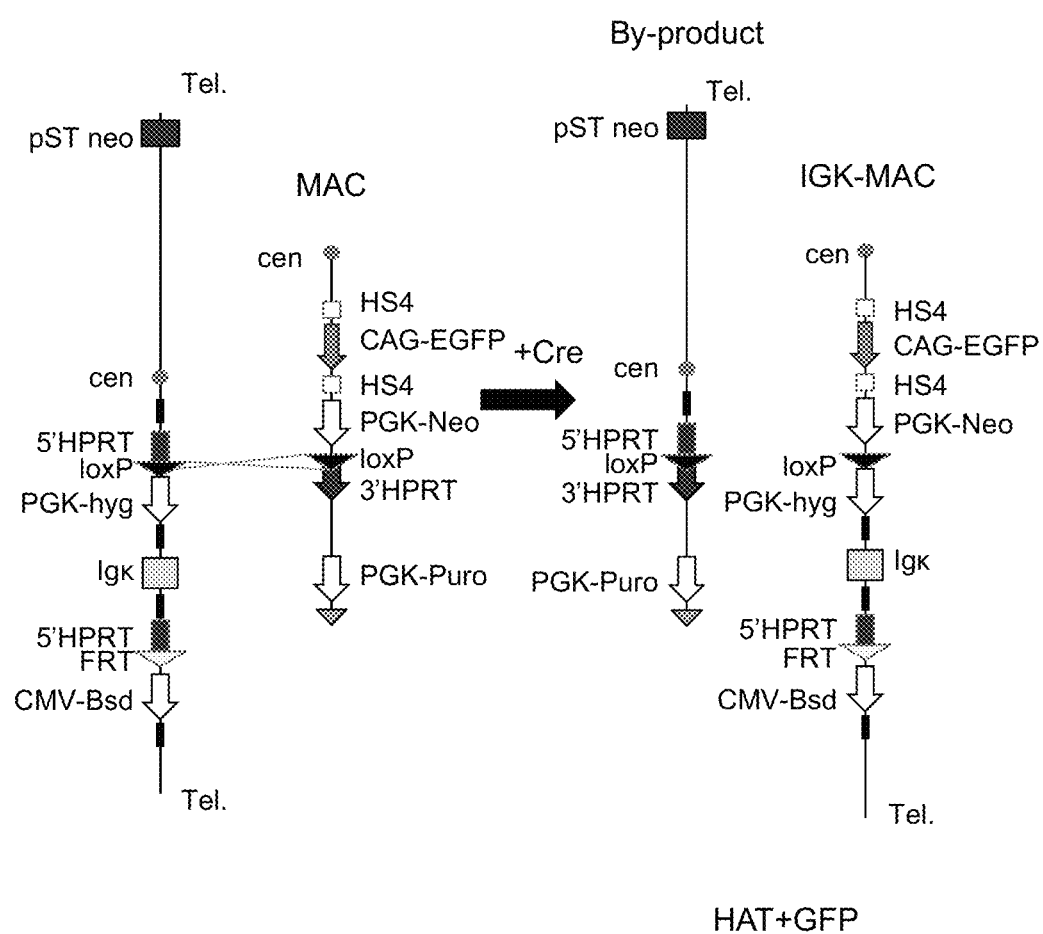
FIG. 7 shows production of IGK-MAC by cloning an IGK region of human chromosome 2 into MAC by translocation using the Cre/loxP system.

Incorporating IGK Region of Human Chromosome 2 into Mouse Artificial Chromosome Vector (MAC) by Translocation Cloning In MAC-carrying CHO cells, the IGK region of the human chromosome 2 is cloned into MAC by translocation. The IGK region is incorporated into MAC by subjecting human chromosome 2 and MAC to reciprocal translocation using the Cre/loxP system (FIG. 7).

[A] Introduction of the Modified Human Chromosome 2 into MAC-Carrying CHO Cells (CHO MAC)

In order to clone the human chromosome 2 region into MAC by translocation using the Cre/Lox system in CHO cells, the modified human chromosome 2 is transferred into MAC-carrying CHO cells.

[A.1] Microcell Fusion and Isolation of Drug Resistant Clone

DT40 521D4 loxP1-28 FRT1-23 and 521D4 loxP4-6 FRT1-15 as donor cells were subjected to microcell fusion to CHO (HPRT⁻) as a CHO hprt-deficient cell carrying the MAC vector (obtained from the Health Science Research Resources Bank; Registration number: JCRB0218) in the same manner as described above.

When the donor cells reached confluency, the cells were incubated for 12 hours with the addition of 20% FBS and 0.025 μg/ml colcemid to form microcells, which were then recovered and suspended in a serum-free DMEM medium, the resulting cell suspension was put into a centrifuge flask coated with poly-L lysine (Wako), incubation was carried out for 30 minutes, and the cells were allowed to adhere to the flask. The serum-free DMEM medium was removed, the centrifuge flask was filled with a cytochalasin B (10 μg/ml, Sigma) solution kept warm at 37° C. in advance, and centrifugation was then carried out at 34° C. and 8,000 rpm for 1 hour. The microcells were suspended in the serum-free DMEM medium and purified using 8-μm, 5-μm, and 3-μm filters. The purified microcells were suspended in 2 ml of a solution of 0.05 mg/ml PHA-P (Sigma) in DMEM, the culture medium was removed from the cell suspension, and the resultant cells was then added to the recipient CHO MAC cells that had reached confluency in a 6-cm cell culture dish. After incubation was carried out for 15 minutes, the microcells were allowed to adhere to the CHO cells. Thereafter, cell fusion was carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells were washed 4 times with 5 ml of serum-free DMEM to remove PEG, and the CHO culture solution was then added. The cells were seeded in ten 10-cm cell culture dishes 24 hours later, 800 μg/ml G418 (Promega) and 6 μg/ml blasticidin were added thereto, and selection culture was then conducted for 10 days. These reactions were repeated 2 times, 26 and 49 drug resistant clones were obtained from the donor cells DT40 521D4 loxP1-28 FRT1-23 and 521D4 loxP4-6 FRT1-15, respectively, and 21 clones and 24 clones selected at random therefrom were subjected to the subsequent analysis. It was confirmed by fluorescence detection that the MAC comprised the EGFP expression cassette incorporated therein and was retained in the drug-resistant clones.

[A.2] Selection of Drug Resistant Clones by PCR Analysis

DNAs were extracted from drug resistant clones and used as templates for PCR in order to confirm that the modified human chromosome 2 had been transferred into CHO MAC cells. The primers are shown below.

Primers for Confirmation of loxP Sequence on the Modified Human Chromosome 2:

cos138 sp L (described above)
cos138 sp R (described above)
x6.1cosRa L (described above)
x6.1cosRa R (described above)

When using the primers cos138 sp L and cos138 sp R, PCR was carried out using Accuprime Taq DNA polymerase (Thermo Fisher Scientific) and buffers and dNTPs (dATP, dCTP, dGTP, and dTTP) included in the kit under the recommended conditions. Temperature and cycle conditions were as follows: after thermal denaturation at 94° C. for 2 minutes, the cycle of 94° C. for 15 seconds, 60° C. for 15 seconds, and 68° C. for 5 minutes was conducted for 35 cycles.

When using the primers x6.1cosRa L and x6.1cosRa R, PCR was carried out using KOD FX (TOYOBO) and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 12 minutes was conducted for 30 cycles.

Primers for Confirmation of Human Chromosome 2 Region:

D2S177 F (described above)
D2S177 R (described above)
FABP1-F (described above)
FABP1-R (described above)
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)
D2S159_1 F (described above)
D2S159_1 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

Primers for Confirmation of FRT Sequence on Modified Human Chromosome 2:

kD9 tcLa L (described above)
kD9 tcLa R (described above)
kD9 tcRa L (described above)
kD9 tcRa R (described above)

PCR was carried out using the primers, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

As a result, 3 positive cell clones and 4 positive cell clones were obtained, respectively.

[A.3] Two-Color FISH Analysis

Figure 8:
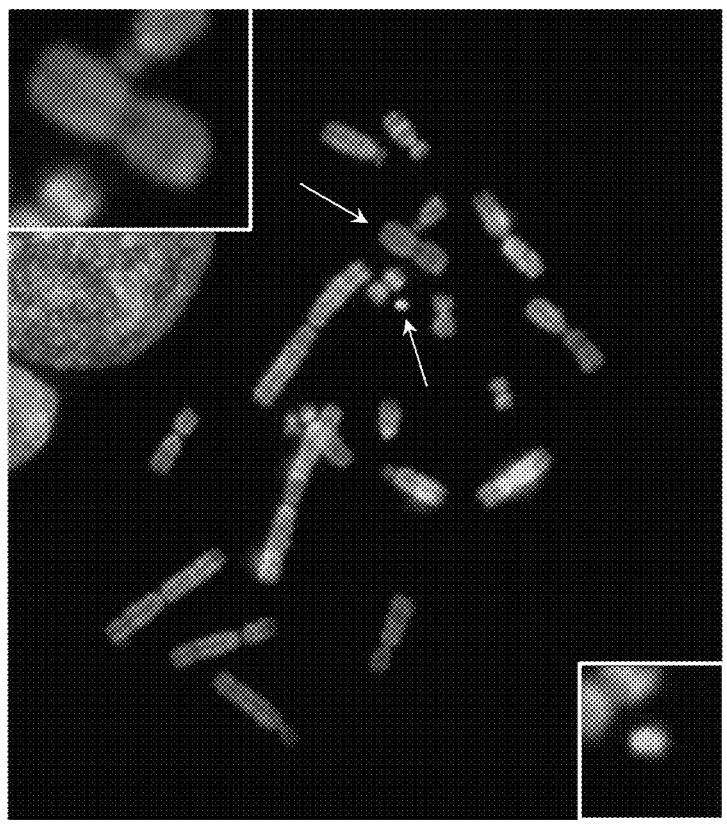
FIG. 8 is a figure obtained by two-color FISH analysis, indicating independently retaining the MAC (indicated by a lower arrow) and the modified human chromosome 2 (indicated by an upper arrow) in CHO cell.

The 3 clones and the 4 clones were subjected to FISH analysis using Human cot-1 DNA and Mouse cot-1 DNA as probes. As a result, the positive cells, i.e. CHO(MAC)hChr.2 LF1-15 #9 and CHO(MAC)hChr.2 LF1-15 #16, that independently carry the MAC and the modified human chromosome 2 (FIG. 8), were obtained.

[B] Cloning of Human Chromosome 2 Region into MAC by Translocation

A human chromosome 2 fragment containing the IGK region is translocated into MAC using the Cre/Lox system.

[B.1] Obtaining HAT Resistant Recombinant Chromosome by Cre Expression

The MAC comprises a loxP site incorporated therein so that recombination is caused with the loxP site of the modified human chromosome 2 in the presence of a Cre recombinase. When the recombination takes place, 5'HPRT in the human chromosome 2 region that is not incorporated in MAC and becomes a by-product is ligated to 3'HPRT at the terminus of the MAC that is a by-product, thereby resulting in reconstruction of the HPRT gene, and CHO (hprt−/−) acquires HAT resistance.

When CHO(MAC)hChr.2 LF1-15 #9 and CHO(MAC) hChr.2 LF1-15 #16 reached confluency in 10-cm cell culture dishes, 18 μg of a Cre expression plasmid (vector name: pBS185) was added using Lipofectamine 2000 (Thermo Fisher Scientific) with reference to the manufacturer's instructions. The culture medium was exchanged with a fresh culture medium 6 hours after the addition, the cells were seeded in ten 10-cm cell culture dishes 24 hours later, and drug selection was then carried out using 1× HAT (Sigma) and 4 μg/ml blasticidin.

The 23 and 24 HAT resistant clones obtained from the above-mentioned cells, respectively, were subjected to the subsequent analysis.

[B.2] Selection of Drug Resistant Clone by PCR Analysis

Genomic DNAs extracted from the HAT resistant cell lines were used as templates, PCR was carried out using the primers shown below in order to select clones in which reciprocal translocation occurred, and whether or not the reciprocal translocation had occurred between the human chromosome 2 fragment and MAC was examined. The primer sequences are shown below.

```
                                        (SEQ ID NO: 31)
TRANS L1 5'-TGGAGGCCATAAACAAGAAGAC-3'

(SEQ ID NO: 32)
TRANS R1: 5'-CCCCTTGACCCAGAAATTCCA-3'

(SEQ ID NO: 33)
KJneo: 5'-CATCGCCTTCTATCGCCTTCTTGACG-3'

(SEQ ID NO: 34)
PGKr-2: 5'-ATCTGCACGAGACTAGTGAGACGTGCTA-3'
```

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.

In addition, PCR was carried out to examine whether or not the human chromosome 2 region and the FRT sequence were also maintained. The primers are shown below.

Primers for Confirmation of Human Chromosome 2 Region:
  D2S177 F (described above)
  D2S177 R (described above)
  FABP1-F (described above)
  FABP1-R (described above)
  EIF2AK3-F (described above)
  EIF2AK3-R (described above)
  RPIA-F (described above)
  RPIA-R (described above)
  IGKC-F (described above)
  IGKC-R (described above)
  IGKV-F (described above)
  IGKV-R (described above)
  Vk3-2 F (described above)
  Vk3-2 R (described above)
  D2S159_1 F (described above)
  D2S159_1 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

Primers for Confirmation of FRT Sequence on Human Chromosome 2:
  kD9 tcLa L (described above)
  kD9 tcLa R (described above)
  kD9 tcRa L (described above)
  kD9 tcRa R (described above)

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

As a result, 23 PCR-positive clones and 24 PCR-positive clones were obtained, respectively.

[B.3] Two-Color FISH Analysis

Figure 9:
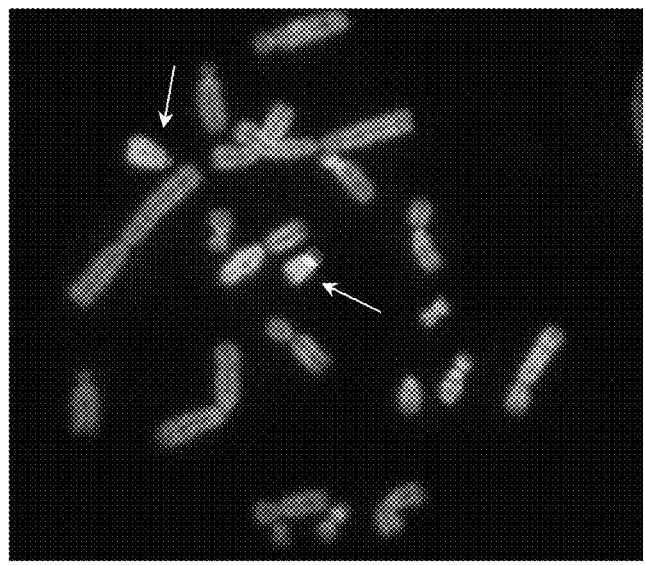
FIG. 9 is a figure obtained by two-color FISH analysis, indicating independently retaining the IGK-MAC (indicated by a lower arrow) comprising the IGK region incorporated in the MAC and a by-product (indicated by an upper arrow).

The 6 clones selected at random were subjected to FISH analysis using Human cot-1 DNA and Mouse cot-1 DNA as probes, and, as a result, it was confirmed that reciprocal translocation occurred between the MAC and the modified human chromosome 2 and that the IGK-MAC, in which the IGK region is inserted into the MAC, and a by-product were independently retained, with respect to the 5 clones and 1 clone (FIG. 9). The two clones, i.e. CHO IGK-MAC #9-3 and CHO IGK-MAC #16-1, were selected and subjected to the subsequent experiment.

Example 3

Modification of Human Chromosome 14 and Transfer Thereof to CHO (hprt−/−) Cell

Figure 10:
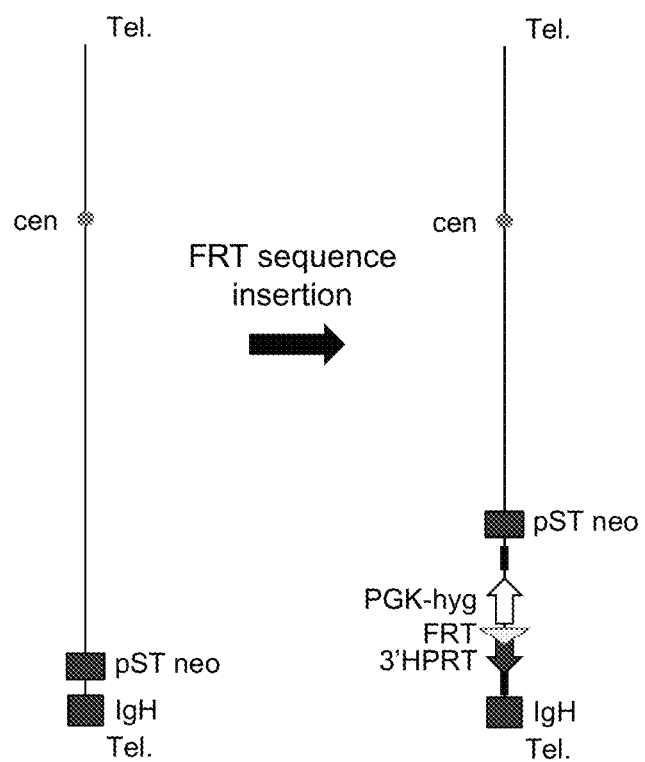
FIG. 10 shows a modified human chromosome 14 in which an FRT sequence has been inserted in order that the IGK-MAC has the IGH region.

The human chromosome 14 was modified and was transferred into CHO (hprt−/−) that was a host cell to incorporate the IGH region into the IGK-MAC (FIG. 10).

[A] Modification of Human Chromosome 14

In order to incorporate the IGH region of the human chromosome 14 into IGK-MAC by translocation cloning, the FRT sequence, which is a recombinant sequence, was inserted into the human chromosome 14.

[A.1] Preparation of Vector for FRT Insertion into Human Chromosome 14

As a basic plasmid for inserting the FRT sequence into DT40 (#14), pMA-RQ (Life technologies) was used. An artificial gene synthesizing sequence (FRT site, Life technologies) was cloned into the vector (vector name: pMA-14SC355). At the outset, the pX6.1 vector was digested with KpnI and ClaI and electrophoresed. Thereafter, the PGKhyg sequence was subjected to gel extraction, and the resultant was ligated to the protruding end formed by digestion of pMA-14SC355 with KpnI and ClaI (vector name: pMA-14SC355hyg). In addition, a plasmid (vector name: pX3.1), in which the loxP sequence and 3'HPRT were inserted into the v907 plasmid (Lexicon genetics), was digested with XbaI and AscI, and the resulting 3'HPRT sequence was ligated to the protruding end formed by digestion of pMA-SC355hyg with NheI (NEB) and MluI (NEB) (vector name: pMA-SC355hyg3'HPRT).

The DNA sequence of human chromosome 14 as an FRT insertion site was obtained from the GenBank database (NC_000014.9). Genomic DNA was extracted from DT40 (#14) and used as a template to amplify the target sequence of homologous recombination. The primer sequences used are shown below.

```
NotISC355-F:
                                     (SEQ ID NO: 35)
5'-TCGAGCGGCCGCGTACAATCTTGGATCACTACAACCTCTGCCTA-3'

AscISC355-R:
                                     (SEQ ID NO: 36)
5'-TCGAGGCGCGCCAGGATTATAGATGTGAGCCATCACTAAGACTCC

T-3'

SalISC355-F4:
                                     (SEQ ID NO: 37)
5'-TCGAGTCGACAGCACGTTGGGAGGCCAAGGCAGGAGAATA-3'

BamHISC355-R4:
                                     (SEQ ID NO: 38)
5'-TCGAGGATCCTGGCTGACACAGCCAGTCCCGGATT-3'
```

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

Figure 11:
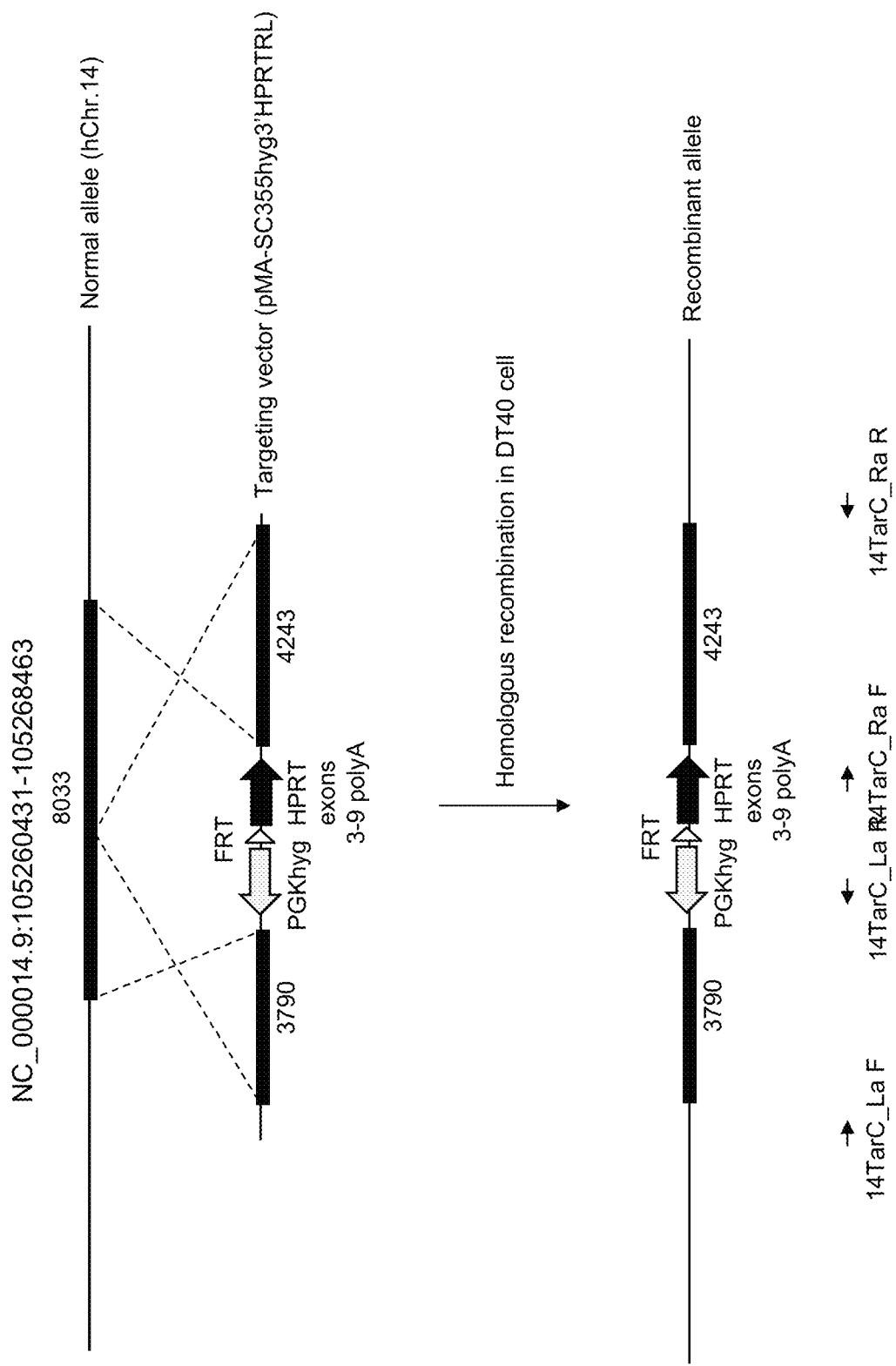
FIG. 11 shows production of an FRT-inserted recombinant allele obtained by modifying the human chromosome 14 allele by homologous recombination using a targeting vector indicated.

The PCR product obtained using the SalISC355-F4 and BamHISC355-R4 primers was digested with SalI and BamHI, and the resultant was ligated to the protruding end formed by digestion of pMA-SC355hyg3'HPRT with SalI and BamHI (pMA-SC355hyg3'HPRTR). Subsequently, the PCR product obtained using the NotISC355-F and AscISC355-R primers was digested with NotI and AscI, and the resultant was ligated to the protruding end formed by digestion of pMA-SC355hyg3'HPRTR with NotI and AscI (vector name: pMA-SC355hyg3'HPRTRL). FIG. 11 shows the targeting vector, the target sequence, and the chromosome allele obtained by homologous recombination.

[A.2] Insertion of FRT into Human Chromosome 14 in Chicken DT40 Cell

Chicken DT40 cells were cultured in RPMI 1640 culture medium (Gibco) supplemented with 10% FBS, 1% chicken serum (Gibco), and 10-4M 2-mercaptoethanol (Sigma). Approximately $10^7$ DT40 (#14) cells were washed once with additive-free RPMI 1640 culture medium and suspended in 0.5 ml of additive-free RPMI 1640 culture medium. The targeting vector pMA-SC355hyg3'HPRTRL (25 µg) linearized with the restriction enzyme NotI (NEB) was added thereto, the resultant was transferred into a cuvette (Bio-Rad Laboratories, Inc.) for electroporation, and the cuvette was allowed to stand at room temperature for 10 minutes. The cuvette was set on Gene Pulser (Bio-Rad Laboratories, Inc.) and voltage was applied under the conditions of 550 V and 25 µF. The cuvette was allowed to stand at room temperature for 10 minutes, the cell suspension was dispensed to twelve 96-well culture plates, and culture was then conducted for 24 hours. Drug selection was carried out with the aid of 15 µg/ml hygromycin. As a result of the reactions repeated 3 times, 73 drug resistant clones were obtained, 23 clones were selected therefrom at random, and genomic DNAs were extracted. Using the genomic DNAs as templates, whether or not site-directed recombination had occurred on human chromosome 14 was examined by PCR. The primer sequences are shown below.

```
                                     (SEQ ID NO: 39)
14TarC_La F: 5'-AGCAATTAGGGCCTGTGCATCTCACTTT-3'

(SEQ ID NO: 40)
14TarC_La R: 5'-CCAGCTCATTCCTCCCACTCATGATCTA-3'

(SEQ ID NO: 41)
14TarC_Ra F: 5'-CATCTGGAGTCCTATTGACATCGCCAGT-3'

(SEQ ID NO: 42)
14TarC_Ra R: 5'-CTTATTCCTCCTTCTGCCCACCCTTCAT-3'
```

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 6 minutes was conducted for 35 cycles.

In addition, the chromosome 14 region was analyzed by PCR. The primer sequences are shown below.

```
                                     (SEQ ID NO: 43)
MTA1-F3: 5'-AGCACTTTACGCATCCCAGCATGT-3'

(SEQ ID NO: 44)
MTA1-R3: 5'-CCAAGAGAGTAGTCGTGCCCCTCA-3'

(SEQ ID NO: 45)
ELK2P2-F: 5'-CCCACTTTACCGTGCTCATT-3'

(SEQ ID NO: 46)
ELK2P2-R: 5'-ATGAAGGTCCGTGACTTTGG-3'

(SEQ ID NO: 47)
g1(g2)-F: 5'-ACCCCAAAGGCCAAACTCTCCACTC-3'

(SEQ ID NO: 48)
g1(g2)-R: 5'-CACTTGTACTCCTTGCCATTCAGC-3'

(SEQ ID NO: 49)
VH3-F: 5'-AGTGAGATAAGCAGTGGATG-3'

(SEQ ID NO: 50)
VH3-R: 5'-CTTGTGCTACTCCCATCACT-3'

(SEQ ID NO: 51)
CH3F3: 5'-AGGCCAGCATCTGCGAGGAT-3'

(SEQ ID NO: 52)
CH4R2: 5'-GTGGCAGCAAGTAGACATCG-3'
```

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles.

As a result of PCR, 10 clones found to be positive were subjected to the subsequent analysis.

[A.3] Two-Color FISH Analysis

Figure 12:
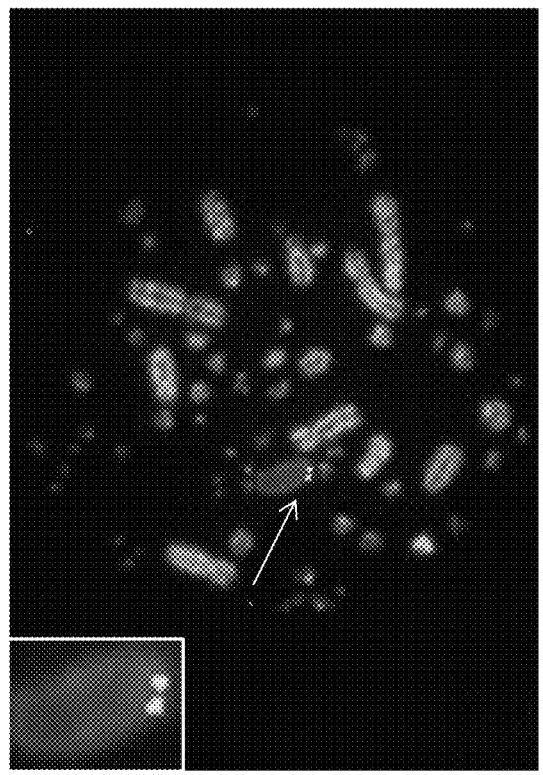
FIG. 12 is a figure obtained by two-color FISH analysis, indicating retention of a copy of human chromosome 14 and insertion of PGKhyg3'FRTHPRT (indicated by an arrow).

The 6 clones selected at random were subjected to FISH analysis using Human cot-1 DNA and pMA-SC355hyg3'HPRT as probes. As a result, one copy of human chromosome 14 was retained and a PGKhyg3'FRTHPRT-derived signal was observed in 90% or more of all the clones, but no signal was detected on human chromosome 14 as a negative control before site-directed insertion of PGKhyg3'FRTHPRT. Thus, site-directed insertion of PGKhygFRT3'HPRT was confirmed (FIG. 12). The 2 clones, i.e. 14DT40#2-4_FRT 3-17 and 3-19, were selected and subjected to the subsequent experiment.

[B] Transfer of Modified Human Chromosome 14 into CHO (hprt−/−) Cell Line

In order to incorporate the IGH region of chromosome 14 into the IGK-MAC in the CHO (hprt−/−) cell line, the modified human chromosome 14 was transferred into the CHO (hprt−/−) cell line.

[B.1] Microcell Fusion and Isolation of Drug Resistant Clone

14DT40#2-4_FRT 3-17 and 3-19 were used as donor cells to subject to microcell fusion to CHO (HPRT⁻).

When the donor cells reached confluency, the cells were incubated for 12 hours with the addition of 20% FBS and 0.025 µg/ml colcemid to form microcells, which were then recovered and suspended in a serum-free DMEM medium, the resulting cell suspension was put into a centrifuge flask coated with poly-L lysine (Wako), and incubation was carried out for 30 minutes, whereby the cells were allowed to adhere to the flask. The serum-free DMEM medium was removed, the centrifuge flask was filled with a cytochalasin B (10 µg/ml, Sigma) solution kept warm at 37° C. in advance, and centrifugation was then carried out at 34° C. and 8,000 rpm for 1 hour. The microcells were suspended in the serum-free DMEM medium and purified using 8-µm, 5-µm, and 3-µm filters. The purified microcells were suspended in 2 ml of a solution of 0.05 mg/ml PHA-P (Sigma) in DMEM, the culture medium was removed from the cell suspension, and the resultant was then added to the recipient CHO (hprt−/−) cells that had reached confluency in a 6-cm cell culture dish. After incubation was carried out for 15 minutes, the microcells were allowed to adhere to the CHO cells. Thereafter, cell fusion was carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells were washed 4 times with 5 ml of serum-free DMEM to remove PEG, and the CHO culture solution was then added. The cells were seeded in ten 10-cm cell culture dishes 24 hours later, 400 µg/ml G418 was added thereto, and selection culture was then conducted for 10 days. These reactions were repeated 2 times, and the obtained 15 drug resistant clones and 2 drug resistant clones were subjected to the subsequent analysis.

[B.2] Selection of Drug Resistant Clones by PCR Analysis

PCR was carried out to examine whether or not the modified human chromosome 14 had been transferred into the CHO (hprt−/−) cell line. The primers are shown below.

Primers for Confirmation of FRT Sequence on Modified Human Chromosome 14:
  14TarC_La F (described above)
  14TarC_La R (described above)
  14TarC_Ra F (described above)
  14TarC_Ra R (described above)

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 6 minutes was conducted for 35 cycles.

Primers for Confirmation of Human Chromosome 14 Region:
  MTA1-F3 (described above)
  MTA1-R3 (described above)
  ELK2P2-F (described above)
  ELK2P2-R (described above)
  g1(g2)-F (described above)
  g1(g2)-R (described above)
  VH3-F (described above)
  VH3-R (described above)
  CH3F3 (described above)
  CH4R2 (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles.

As a result, 14 PCR-positive clones and 2 PCR-positive clones were obtained.

[B.3] Two-Color FISH Analysis

Figure 13:
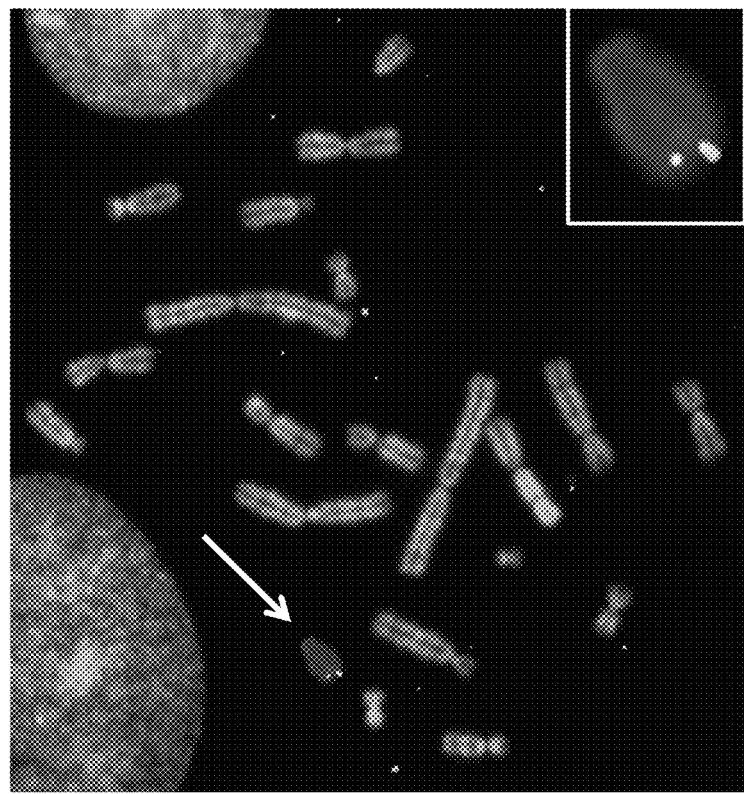
FIG. 13 is a figure obtained by two-color FISH analysis, indicating retention of a copy of human chromosome 14 showing a PGKhygFRT3'HPRT-derived signal in CHO cell.

The 6 clones and the 2 clones selected at random were subjected to FISH analysis using Human cot-1 DNA and pMA-SC355hyg3'HPRT as probes. As a result, positive cells retaining one copy of chromosome 14 exhibiting a PGKhygFRT3'HPRT-derived signal were detected (FIG. 13). The positive cells, i.e. CHO hprt−/− 14FRT #3-17_8 and CHO hprt−/− 14FRT #3-17_14, were subjected to the subsequent experiment.

Example 4

Figure 14:
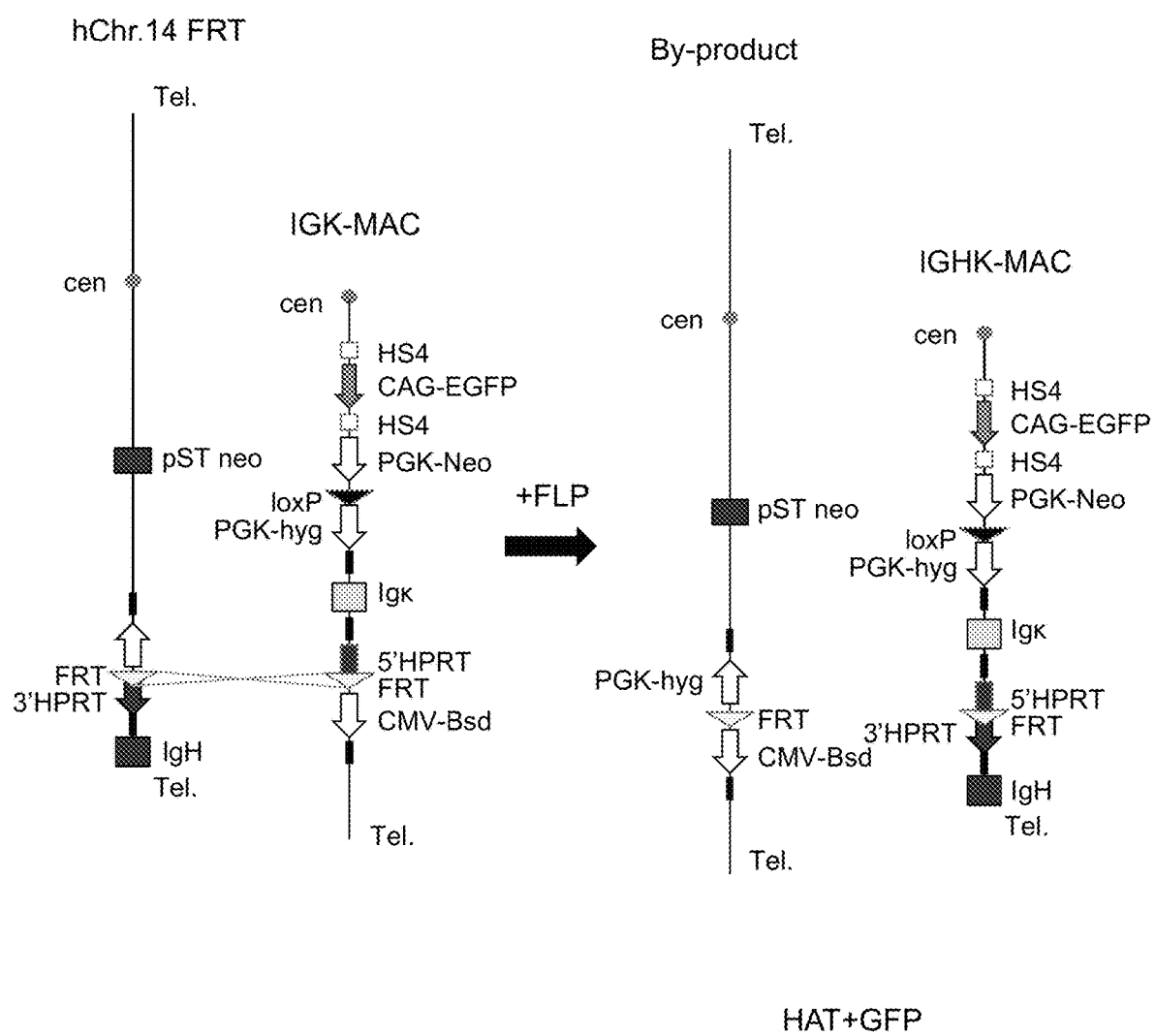
FIG. 14 shows a procedure for producing the IGHK-MAC in which the IGH region was comprised in the IGK-MAC.

Incorporating IGH Region of Human Chromosome 14 into IGK-MAC by Reciprocal Translocation The prepared IGK-MAC was transferred into the CHO (hprt−/−) cell line carrying the modified human chromosome 14, thereby incorporating the IGH region into the IGK-MAC by recombination using the FRT/Flp system. Thus, IGHK-MAC was prepared (FIG. 14).

[A] Transfer of IGK-MAC into CHO CHO (hprt−/−) Cell Line Carrying Modified Human Chromosome 14

[A.1] Microcell Fusion and Isolation of Drug Resistant Clone

The donor cells (CHO IGK-MAC #9-3) were cultured in a cell culture dish, the culture medium was exchanged with an F12 medium supplemented with 20% FBS and 0.1 µg/ml colcemid when the cells reached confluency, the culture medium was further exchanged with a fresh F12 medium supplemented with 20% FBS and 0.1 µg/ml colcemid after 48-hr culture, and the culture was incubated overnight to form microcells. The culture medium was removed, the centrifuge flask was filled with a cytochalasin B (10 µg/ml, Sigma) solution kept warm at 37° C. in advance, and centrifugation was then carried out at 34° C. and 8,000 rpm for 1 hour. Microcells were suspended in the serum-free DMEM medium and purified using 8-µm, 5-µm, and 3-µm filters. Thereafter, the microcells were suspended in 2 ml of a solution of 0.05 mg/ml PHA-P (Sigma) in DMEM, the culture medium was removed from the cell suspension, and the resultant was then added to the recipient CHO hprt−/− 14FRT #3-17_8 and CHO hprt−/− 14FRT #3-17_14 cells that had reached confluency in 6-cm cell culture dishes. After incubation was carried out for 15 minutes, the microcells were allowed to adhere to the CHO cells. Thereafter, cell fusion was carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells were washed 4 times with 5 ml of serum-free DMEM to remove PEG, and the CHO culture solution was then added. The cells were seeded in ten 10-cm cell culture dishes 24 hours later, 600 µg/ml G418 and 6 µg/ml blasticidin were added thereto, and selection culture was then conducted for 10 days. The resulting 18 drug-resistant clones and 15 drug-resistant clones were subjected to the subsequent analysis.

[A.2] Selection of Drug Resistant Clones by PCR Analysis

PCR was carried out in order to examine whether or not the IGK-MAC had been transferred into the CHO (hprt−/−) cell line carrying the modified human chromosome 14 and whether or not the modified human chromosome 14 was retained. The primers used are shown below.

Primers for Confirmation of IGK-MAC:
  KJneo (described above)
  PGKr-2 (described above)

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.

Primers for Confirmation of FRT Insertion Site on IGK-MAC:
  kD9 tcLa L (described above)
  kD9 tcLa R (described above)
  kD9 tcRa L (described above)
  kD9 tcRa R (described above)

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

Primers for Confirmation of Human Chromosome 2 Region:
  D2S177 F (described above)
  D2S177 R (described above)
  EIF2AK3-F (described above)
  EIF2AK3-R (described above)
  RPIA-F (described above)
  RPIA-R (described above)
  IGKC-F (described above)
  IGKC-R (described above)
  IGKV-F (described above)
  IGKV-R (described above)
  Vk3-2 F (described above)
  Vk3-2 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: for thermal denaturation at 95° C. for 10 minutes, the cycle of 95° C. for 30 seconds, 60° C. for 30 seconds, and 72° C. for 1 minute was conducted for 35 cycles.

Primers for Confirmation of FRT Insertion Site on Modified Human Chromosome 14:
  14TarC_La F (described above)
  14TarC_La R (described above)
  14TarC_Ra F (described above)
  14TarC_Ra R (described above)

PCR was carried out using the primers described above, KOD FX (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 6 minutes was conducted for 35 cycles.

Primers for Confirmation of Human Chromosome 14 Region:
  MTA1-F3 (described above)
  MTA1-R3 (described above)
  ELK2P2-F (described above)
  ELK2P2-R (described above)
  g1(g2)-F (described above)
  g1(g2)-R (described above)
  VH3-F (described above)
  VH3-R (described above)
  CH3F3 (described above)
  CH4R2 (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles.

As a result, 12 clones and 15 clones were found to be PCR positive, respectively.

[A.3] Two-Color FISH Analysis

Figure 15:
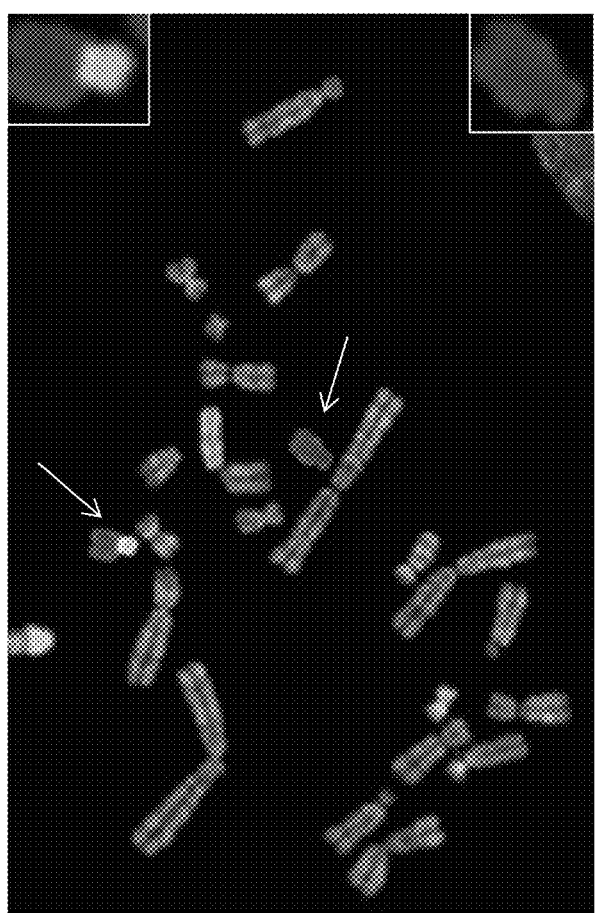
FIG. 15 is a figure obtained by two-color FISH analysis, indicating that a copy of IGK-MAC (indicated by a lower arrow) and a copy of the modified human chromosome 14 (indicated by an upper arrow) was independently comprised in a clone confirmed.

The 6 clones and the 5 clones selected at random were subjected to FISH analysis using Human cot-1 DNA and Mouse cot-1 DNA as probes. As a result, clones, in which a copy of IGK-MAC and a copy of the modified human chromosome 14 were independently maintained, were detected (FIG. 15). The two clones CHO Igk-MAC #9-3 8-5 and CHO Igk-MAC #9-3 14-9 were selected and subjected to the subsequent experiment.

[B] Construction of IGHK-MAC Using FRT/Flp Recombination System

IGK-MAC and the modified human chromosome 14 were subjected to reciprocal translocation using the FRT/Flp system to clone the IGH region derived from human chromosome 14 into IGK-MAC by translocation. Thus, IGHK-MAC was constructed.

[B.1] Obtaining HAT Resistant Recombinant Chromosome by FLP Expression

The FRT site on IGK-MAC was subjected to reciprocal translocation with the FRT site on the modified human chromosome 14 in the presence of FLP recombinase. When recombination took place, 5'HPRT was ligated to 3'HPRT on IGHK-MAC, the HPRT gene was reconstructed, and HAT resistance was acquired. When CHO Igk-MAC #9-3 8-5 and CHO Igk-MAC #9-3 14-9 reached confluency in 10-cm cell culture dishes, 18 µg of an FLP expression plasmid was added using Lipofectamine 2000 (Thermo Fisher Scientific) with reference to the manufacturer's instructions. The culture medium was exchanged with a fresh culture medium 6 hours after the addition, the cells were seeded in ten 10-cm cell culture dishes 24 hours later, and drug selection was then carried out using 1× HAT and 6 µg/ml blasticidin.

The resulting 24 HAT resistant clones were subjected to the subsequent analysis.

[B.2] Selection of Drug Resistant Clones by PCR Analysis

In order to confirm the occurrence of expected reciprocal translocation and the construction of IGHK-MAC using the FRT/FLP system, DNAs were extracted from the drug resistant clones and used as templates for PCR analysis. The primers are shown below.

Primers for Confirmation of Site of Ligation by Reciprocal Translocation:

TRANS L1 (described above)
TRANS R1 (described above)

```
                                           (SEQ ID NO: 53)
CMVr-1: 5'-CCTATTGGCGTTACTATGGGAACATACG-3'
```

PGKr-2 (described above)
KJneo (described above)
PGKr-2 (described above)

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.

Primers for Confirmation of Human Chromosome 2 Region:

D2S177 F (described above)
D2S177 R (described above)
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

Primers for Confirmation of Human Chromosome 14 Region:

MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles. As a result, 22 clones and 24 clones were found to be positive, respectively.

[B.3] Two-Color FISH Analysis

Figure 16:
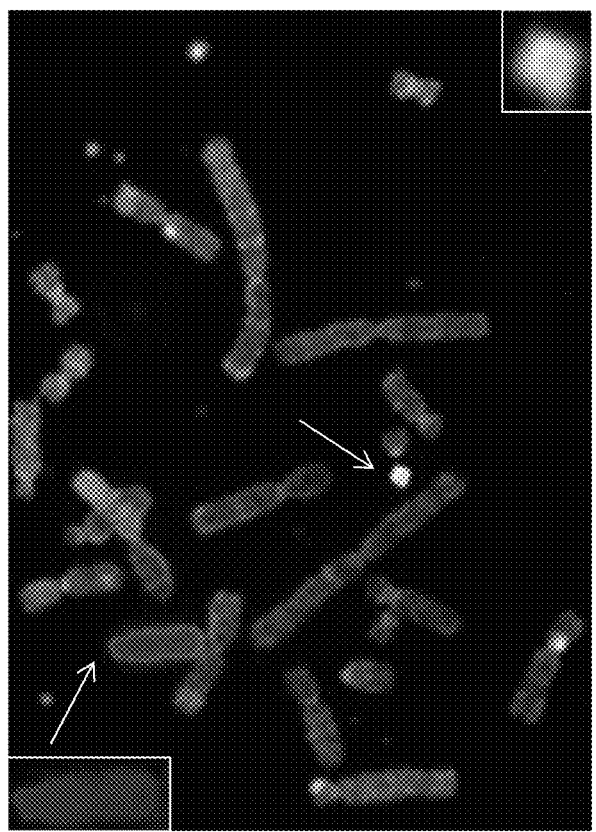
FIG. 16 is a figure obtained by two-color FISH analysis, indicating the independent presence of a copy of IGHK-MAC (indicated by an upper arrow). A lower arrow indicates a by-product resulting from FRT/FLP recombination.

The 6 clones each selected at random were subjected to FISH analysis using Human cot-1 DNA and Mouse cot-1 DNA as probes. As a result, it was confirmed that the length of the chromosome 14, as a by-product, that was not be inserted in the MAC was su increased by translocation of an excessive chromosome 2 region, suggesting the occurrence of reciprocal translocation, and that a copy of a chromosome which is presumed to be IGHK-MAC was independently present (FIG. 16). The two clones, i.e. CHO IGHK-MAC 8-1 and CHO IGHK-MAC 14-7, were selected and subjected to the following experiment.

Figure 17:
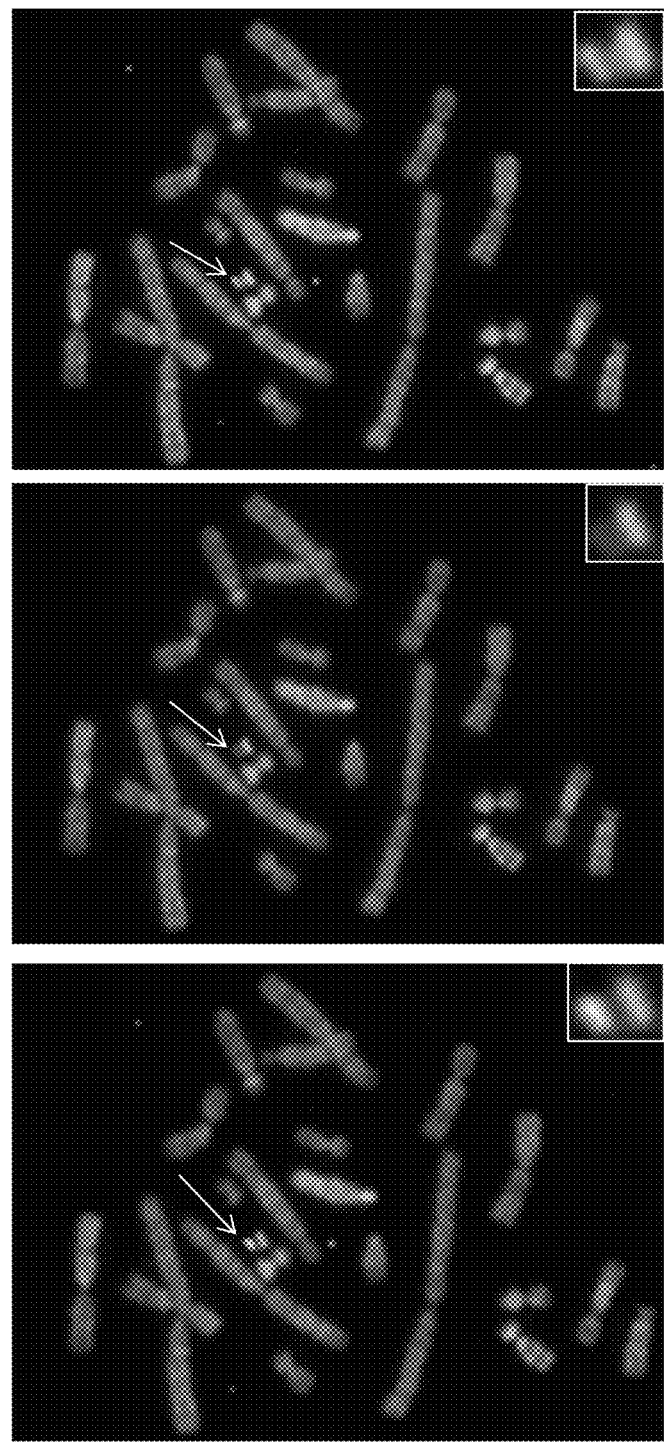
FIG. 17 is a figure obtained by two-color FISH analysis of a CHO IGHK-MAC clone using BAC clones, i.e. CH17-405H5 (IGK region) and CH17-262H11 (IGH region), as probes, and indicates that signals showing the presence of the IGK region and the IGH region were observed on the MAC in the clone and that it was confirmed that the IGHK-MAC (indicated by an arrow) was constructed, where the left panel shows marged signals, the center panel shows only the signal of CH17-405H5 (IGK region), and the right panel shows only the signal of CH17-262H11 (IGH region).
Figure 18:
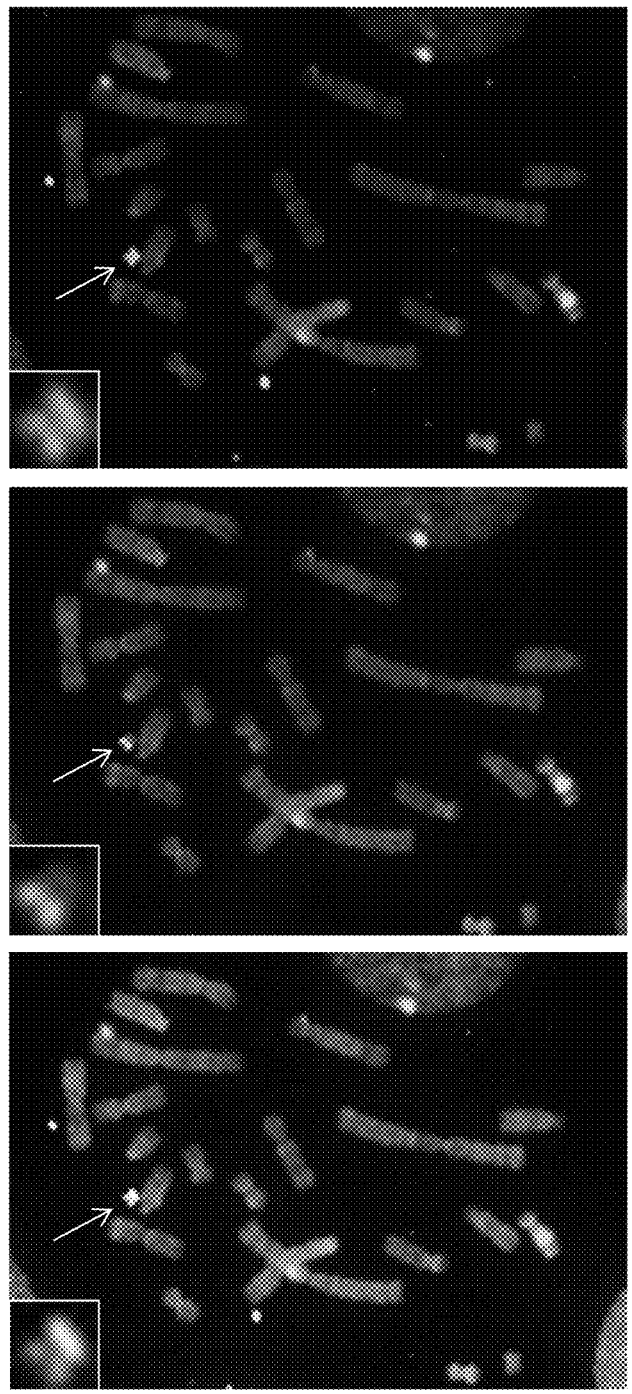
FIG. 18 is a figure obtained by two-color FISH analysis of a CHO IGHK-MAC clone using a combination of BAC clones, i.e. CH17-216K2 (IGK region) and CH17-212P11 (IGH region) as probes, and indicates that signals showing the presence of the IGK region and the IGH region were observed on MAC in the clone and that it was confirmed that IGHK-MAC (indicated by an arrow) was constructed, where the left panel shows marged signals, the center panel shows only the signal of CH17-216K2 (IGK region), and the right panel shows only the signal of CH17-212P11 (IGH region).

These 2 clones were subjected to two-color FISH analysis using a combination of BAC clones CH17-405H5 (IGK region: CHORI) and CH17-262H11 (IGH region: CHORI) and a combination of BAC clones CH17-216K2 (IGK region: CHORI) and CH17-212P11 (IGH region: CHORI), as probes, in order to thoroughly analyze whether or not IGHK-MAC had been actually constructed. As a result, signals indicating the presence of the IGK region and the IGH region were observed on MACs of both the two clones. Thus, construction of IGHK-MAC was confirmed (FIG. 17, FIG. 18).

Example 5

Transfer of IGHK-MAC into CHO K1 Cell Line

Both of IGHK-MAC and a by-product, which was formed upon reciprocal translocation for constructing IGHK-MAC, comprise a Neo-resistant gene inserted therein. When the IGHK-MAC and the by-product are transferred into the target cells by microcell fusion, a cell into which either or both of IGHK-MAC and the by-product has/have been transferred can be obtained by drug selection with G418. Because the MAC comprises EGFP inserted therein, whether or not IGHK-MAC has been transferred into a target cell can be determined. In order to prepare a donor cell capable of efficient chromosome transfer and carrying only IGHK-MAC, the IGHK-MAC was transferred into the CHO K1 cell line.

[A] Microcell Fusion and Isolation of Drug Resistant Clone

A cell line carrying only IGHK-MAC was prepared by chromosome transfer.

[A.1] Transfer of IGHK-MAC into CHO K1 Cell Line

The donor cells (CHO IGHK-MAC 8-1 and CHO IGHK-MAC 14-7) were cultured in cell culture dishes, the culture medium was exchanged with an F12 medium supplemented with 20% FBS and 0.1 μg/ml colcemid when the cells reached confluency, the culture medium was further exchanged with a fresh F12 medium supplemented with 20% FBS and 0.1 μg/ml colcemid after the 48-hr culture, and the culture was incubated overnight to form microcells. The culture medium was removed, the centrifuge flask was filled with a cytochalasin B (10 μg/ml, Sigma) solution kept warm at 37° C. in advance, and centrifugation was then carried out at 34° C. and 8,000 rpm for 1 hour. Microcells were suspended in the serum-free DMEM medium and purified using 8-μm, 5-μm, and 3-μm filters. Thereafter, the microcells were suspended in 2 ml of a solution of 0.05 mg/ml PHA-P (Sigma) in DMEM, the culture medium was removed from the cell suspension, and the resultant was then added to the recipient CHO K1 cell line that had reached confluency in a 6-cm cell culture dish. After incubation was carried out for 15 minutes, the microcells were allowed to adhere to the CHO cells. Thereafter, cell fusion was carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells were washed 4 times with 5 ml of serum-free DMEM to remove PEG, and the CHO culture solution was then added. The cells were seeded in ten 10-cm cell culture dishes 24 hours later, 800 µg/ml G418 was added, and selection culture was then conducted for 10 days. The resulting 20 and 13 drug-resistant clones were subjected to the subsequent analysis. Concerning these clones, GFP fluorescent protein expression was observed on IGHK-MAC.

[A.2] Selection of Drug Resistant Clones by PCR Analysis

In order to confirm that IGHK-MAC had been transferred into the CHO K1 cell line, DNAs were extracted from the drug resistant clones and used as templates to perform PCR analysis. The primers are shown below.

Primers for Confirmation of Site of Ligation by Reciprocal Translocation:
TRANS L1 (described above)
TRANS R1 (described above)
CMVr-1 (described above)
PGKr-2 (described above)
KJneo (described above)
PGKr-2 (described above)

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.

Primers for Confirmation of Human Chromosome 2 Region:
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles.

As a result, 14 and 10 positive clones were obtained.

[A.3] Two-Color FISH Analysis

Figure 19:
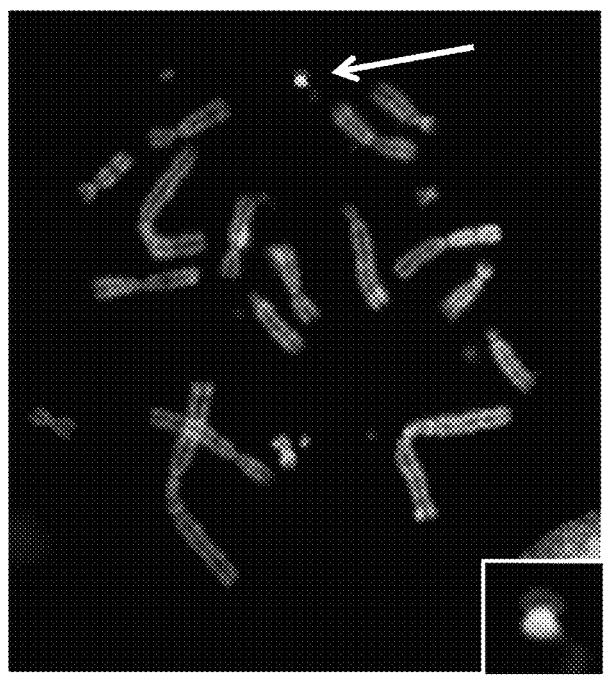
FIG. 19 is a figure obtained by two-color FISH analysis, indicating transfer of IGHK-MAC (indicated by an arrow) into the CHO K1 cell line.

The 6 clones each selected from among the 14 and 10 positive clones at random were subjected to FISH analysis using Human cot-1 DNA and Mouse cot-1 DNA as probes. As a result, two of the 6 clones were observed to carry only IGHK-MAC as expected (FIG. 19).

Figure 20:
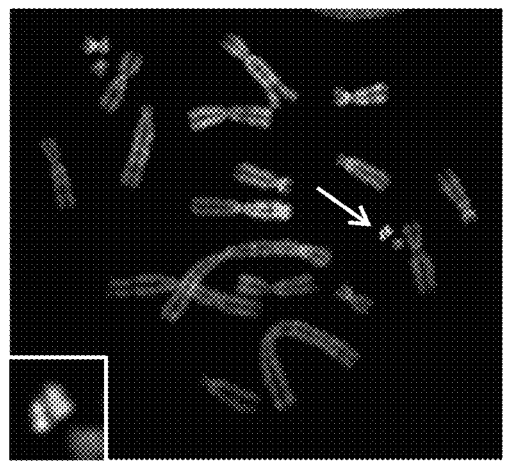
FIG. 20 is a figure obtained by two-color FISH analysis of the IGHK-MAC (indicated by an arrow) in CHO K1 cell line using BAC clone CH17-216K2 (IGK region) and CH17-212P11 (IGH region) as probes.
Figure 21:
FIG. 21 is a figure obtained by two-color FISH analysis of the IGHK-MAC (indicated by an arrow) in CHO K1 cell line using the BAC clones, i.e. CH17-405H5 (IGK region) and RP11-731F5 (IGH region), as probes.

Two clones were selected therefrom and subjected to two-color FISH analysis using a combination of BAC clones CH17-216K2 (IGK region) and CH17-212P11 (IGH region) and a combination of BAC clones CH17-405H5 (IGK region) and RP11-731F5 (IGH region), as probes. As a result, CHO K1 IGHK-MAC 8-1 #1 and CHO K1 IGHK-MAC 14-7 #9 maintaining the IGHK-MAC structure as expected were subjected to the subsequent experiment (FIG. 20, FIG. 21).

Example 6

Transfer of IGHK-MAC into Mouse ES Cell and Rat ES Cell

[A] Transfer of IGHK-MAC into Mouse ES Cell

When producing a human antibody-producing mouse, it is needed: to transfer IGHK-MAC into mouse ES cells; to inject the resultant cells into an 8-cell-stage fertilized egg; to prepare a chimeric mouse; and to allow the IGHK-MAC to transmit to offsprings.

[A.1] Microcell Fusion and Isolation of Drug Resistant Clone

As donor cells, CHO K1 IGHK-MAC 8-1-1 and CHO K1 IGHK-MAC 14-7-9 were used. The donor cells were cultured in cell culture dishes, the culture medium was exchanged with an F12 medium supplemented with 20% FBS and 0.1 µg/ml colcemid when the cells reached confluency, the culture medium was further exchanged with a fresh F12 medium supplemented with 20% FBS and 0.1 µg/ml colcemid 48 hours after the initiation of culture, and the culture was incubated overnight to form microcells. The culture medium was removed, the centrifuge flask was filled with a cytochalasin B (10 µg/ml, Sigma) solution kept warm at 37° C. in advance, and centrifugation was then carried out at 34° C. and 8,000 rpm for 1 hour. Microcells were suspended in the serum-free DMEM medium and purified using 8-µm, 5-µm, and 3-µm filters. Thereafter, centrifugation was carried out at 2,000 rpm for 10 minutes, and thereafter the resultant was suspended in 5 ml of the serum-free DMEM medium. The suspension was further centrifuged at 2,000 rpm for 10 minutes. As recipient cells, the mouse ES cell lines HKD31 6TG-9 (where the mouse Igh and Igk genes have been destroyed; disclosed in WO 98/37757) and XO ES9 (where the antibody gene is not destroyed) were used. Culture was conducted in DMEM (Dulbecco's Modified Eagle's Medium-high glucose; Sigma) supplemented with 10% FCS, LIF (murine leukemia inhibitory factor), $1\times10^{-5}$ M 2-ME (2-mercaptoethanol; Sigma), L-glutamine (3.5 g/ml: GIBCO), a sodium pyruvate solution (3.5 g/ml: GIBCO), and MEM non-essential amino acids (0.125 mM; GIBCO) in the presence of 5% $CO_2$ at 37° C. The surface of the mouse ES cells that had reached confluency in a 10-cm cell culture dish was washed twice with PBS(-). Thereafter, the cells were dispersed by trypsin treatment, recovered in a DMEM medium supplemented with 10% FBS, and centrifuged at 1,500 rpm. The supernatant was removed therefrom, the cells were resuspended in 5 ml of the serum-free culture solution, and the cell suspension was gently added to a serum-free medium containing the microcell pellet after centrifugation, followed by centrifugation at 1,200 rpm. The supernatant was removed, cell fusion was carried out exactly for 1 minute and 30 seconds using 0.5 ml of a PEG1000 (Wako) solution (prepared by completely dissolving 5 g of PEG1000 in the serum-free DMEM medium and adding 1 ml of dimethyl sulfoxide thereto, followed by sterilization by filtration). The serum-free culture solution (DMEM) (13 ml) was gently added thereto, and centrifugation was then conducted at 1,200 rpm. The supernatant was removed, a general culture solution for mouse ES cell was added, mitomycin-treated G418-resistant mouse embryonic fibroblasts were used as the feeder cell, the cells were seeded in two 10-cm cell culture dishes, and the cells were then incubated overnight. G418 was added at a concentration of 250 µg/ml, and selection culture was conducted for 3 to 4 weeks. As a result of the reactions repeated 4, 4, 6, and 6 times, respectively, 6, 4, 7, and 4 EGFP-positive and drug-resistant clones were obtained, and these clones were subjected to the subsequent analysis.

[A.2] Selection of Drug Resistant Clones by PCR Analysis

In order to confirm that IGHK-MAC had been transferred into the mouse ES cell line, DNAs of the drug resistant clones were extracted and used as templates to perform PCR analysis. The primers are shown below.

Primers for Confirmation of Site of Ligation by Reciprocal Translocation:
  TRANS L1 (described above)
  TRANS R1 (described above)
  CMVr-1 (described above)
  PGKr-2 (described above)
  KJneo (described above)
  PGKr-2 (described above)

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.

Primers for Confirmation of Human Chromosome 2 Region:
  EIF2AK3-F (described above)
  EIF2AK3-R (described above)
  RPIA-F (described above)
  RPIA-R (described above)
  IGKC-F (described above)
  IGKC-R (described above)
  IGKV-F (described above)
  IGKV-R (described above)
  Vk3-2 F (described above)
  Vk3-2 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

Primers for Confirmation of Human Chromosome 14 Region:
  MTA1-F3 (described above)
  MTA1-R3 (described above)
  ELK2P2-F (described above)
  ELK2P2-R (described above)
  g1(g2)-F (described above)
  g1(g2)-R (described above)
  VH3-F (described above)
  VH3-R (described above)
  CH3F3 (described above)
  CH4R2 (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles.

When HKD31 6TG-9 was used, as a result, CHO K1 IGHK-MAC 8-1-1-derived 4 clones and CHO K1 IGHK-MAC 14-7-9-derived 2 clones were found to be PCR-positive. When XO ES9 was used, CHO K1 IGHK-MAC 8-1-1-derived 4 clones and CHO K1 IGHK-MAC 14-7-9-derived 2 clones were found to be PCR-positive. These clones were subjected to the subsequent analysis.

[A.3] Two-Color FISH Analysis

Figure 22:
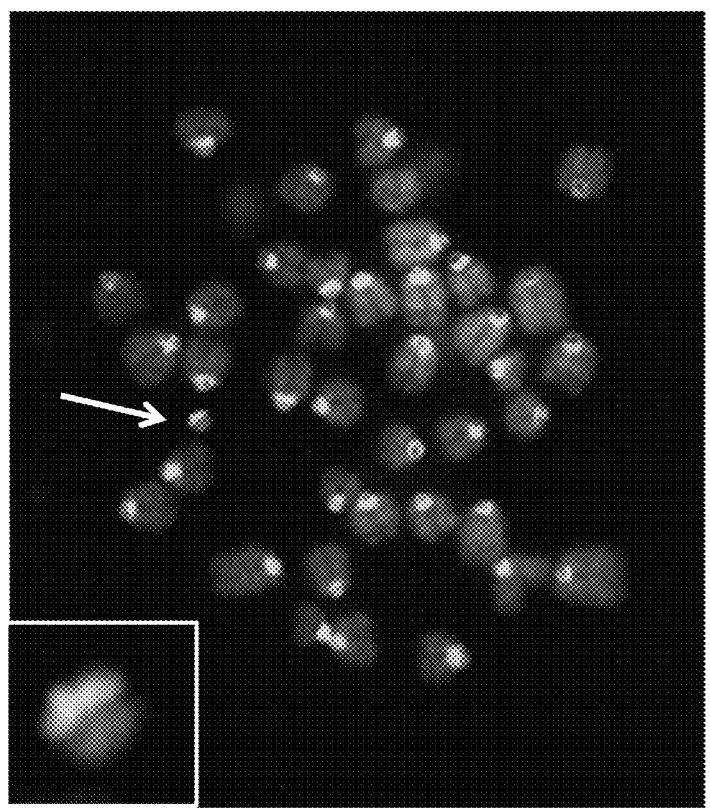
FIG. 22 is a figure obtained by FISH analysis of the IGHK-MAC-carrying Mouse ES (indicated by an arrow).

FISH analysis was carried out using Human cot-1 DNA and Mouse cot-1 DNA as probes. When HKD31 6TG-9 was used, as a result, CHO K1 IGHK-MAC 8-1-1-derived 4 clones and a CHO K1 IGHK-MAC 14-7-9-derived clone were found to carry only IGHK-MAC as expected. When XO ES9 was used, CHO K1 IGHK-MAC 8-1-1-derived 3 clones and a CHO K1 IGHK-MAC 14-7-9-derived clone were found to carry only IGHK-MAC as expected. Thus, these clones were found to retain the mouse ES normal karyotype (FIG. 22).

These clones were subjected to the following experiment.

[B] Transfer of IGHK-MAC into Rat ES Cells

When producing a human antibody-producing rat, it is needed: to transfer IGHK-MAC into rat ES cells; to inject the resultant cells into an 8-cell-stage embryo; to prepare a chimeric rat; and to allow the IGHK-MAC to transmit to offsprings.

[B.1] Microcell Fusion and Isolation of Drug Resistant Clone

IGHK-MAC was introduced into rat ES cells in the same manner as with microcell fusion to mouse ES cells as described in A.1 above. As donor cells, CHO IGHK-MAC 8-1, CHO IGHK-MAC 14-7, CHO K1 IGHK-MAC 8-1-1, and CHO K1 IGHK-MAC 14-7-9 were used. Following fusion, the cells were incubated overnight, G418 was added thereto to a concentration of 150 µg/ml, and selection culture was conducted for 3 to 4 weeks. The reaction was repeated twice, and the K1 cells were subjected to the reaction 8 times. As a result, GFP-positive and drug-resistant clones; i.e., CHO IGHK-MAC 8-1-derived 9 clones, CHO IGHK-MAC 14-7-derived 12 clones, CHO K1 IGHK-MAC 8-1 #1-derived 90 clones, and CHO K1 IGHK-MAC 14-7 #9-derived 34 clones, were obtained. The CHO IGHK-MAC 8-1-derived 9 clones and CHO IGHK-MAC 14-7-derived 12 clones were subjected to the subsequent analysis.

[B.2] Selection of Drug Resistant Clones by PCR Analysis

In order to confirm that IGHK-MAC had been transferred into the rat ES cell line, DNAs were extracted from the drug resistant clones and used as templates to perform PCR analysis. The primers are shown below.
Primers for Confirmation of Site of Ligation by Reciprocal Translocation:
TRANS L1 (described above)
TRANS R1 (described above)
CMVr-1 (described above)
PGKr-2 (described above)
KJneo (described above)
PGKr-2 (described above)

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.
Primers for Confirmation of Human Chromosome 2 Region:
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.
Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

Figure 23:
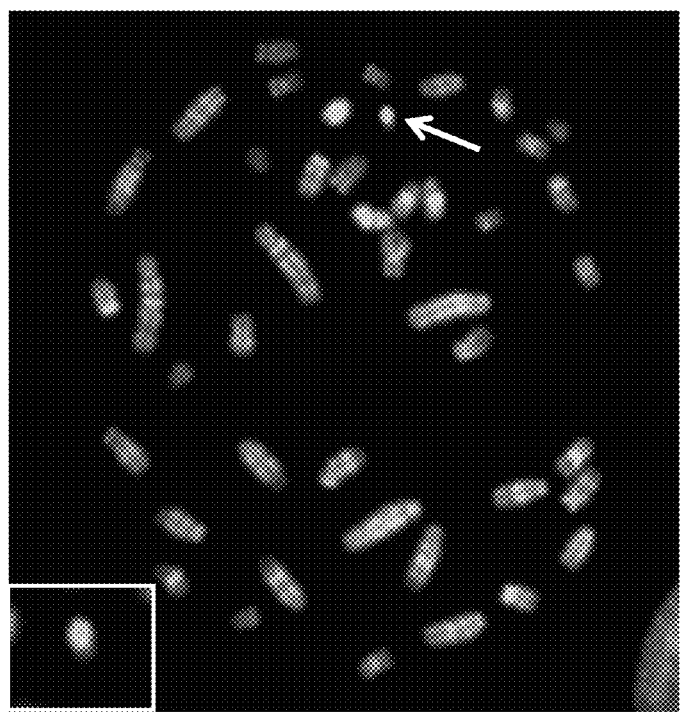
FIG. 23 is a figure obtained by FISH analysis of IGHK-MAC-carrying Rat ES (indicated by an arrow).

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles. The 6 positive clones and 9 clones obtained were subjected to the subsequent analysis.
[B.3] Two-Color FISH Analysis FISH analysis was carried out using Human cot-1 DNA and Mouse cot-1 DNA as probes. As a result, the 4 clones; i.e., rES14-7 #4, rES14-7#6, rES8-1 #3, and rES8-1#8, were found to carry only IGHK-MAC as expected and maintain the rat ES normal karyotype (42 chromosomes) (FIG. 23). These 4 clones were subjected to the subsequent experiment.

Example 7

Preparation of Chimeric Mice and Rats and Transmission to Offspring

Chimeric mice and rats were prepared using ES cells carrying IGHK-MAC to allow the IGHK-MAC to transmit to offsprings.
[A] Preparation of IGHK-MAC-Carrying Mice IGHK-MAC-carrying mice were prepared and analyzed. Chimeric mice obtained during the process were also analyzed.
[A.1] Preparation of Chimeric Mice Using the mouse ES cells carrying IGHK-MAC, chimeric mice are prepared in accordance with the techniques described in Gene Targeting, Experimental Medicine, 1995. As host cells, the morula obtained by sexual crossbreeding of MCH (ICR) (white, purchased from CLEA Japan, Inc.) and the 8-cell-stage embryo were used. Whether or not the newborn mice obtained though transplantation of the injected embryo into a surrogate mother are chimeric mice, can be determined based on the coat color.

Embryos into which HKD31 6TG-9 and XO ES9 mouse ES (IGHK-MAC) female clones were transplanted into surrogate mothers and chimeric mice (a dark brown color area was observed in coat color) were obtained. Chimeric mice were prepared using mouse ES cells of HKD31 6TG-9 IGHK-MAC8-1-1 #1, 3, 5, and 6, HKD31 6TG-9 IGHK-MAC 14-7-9 #1, and XO ES9 IGHK-MAC 8-1-1 #1 and 2. As a result of transplantation of 51 embryos into which HKD31 6TG-9 IGHK-MAC 14-7-9 #1 had been injected into 3 surrogate mothers, in particular, three 100% chimeric mice and a 90% chimeric mouse (determined based on a coat color) were obtained. As a result of transplantation of 140 embryos into which XO ES9 IGHK-MAC 8-1-1 #1 had been injected into 8 surrogate mothers, six 100% chimeric mice and seven 80-90% chimeric mice were obtained.
[A.2] Analysis of Retention of IGHK-MAC on Chimeric Mice The tails were obtained from chimeric mice aged 3 weeks or older in accordance with the method described in Motoya Katsuki, A Laboratory Manual of Development Engineering, Kodansha Scientific, 1987, and genomic DNAs were extracted using the Puregene DNA Isolation Kit (Qiagen). PCR analysis was carried out using the primers and the PCR conditions as described in Example 6 to confirm the retention of IGHK-MAC.

Figure 24:
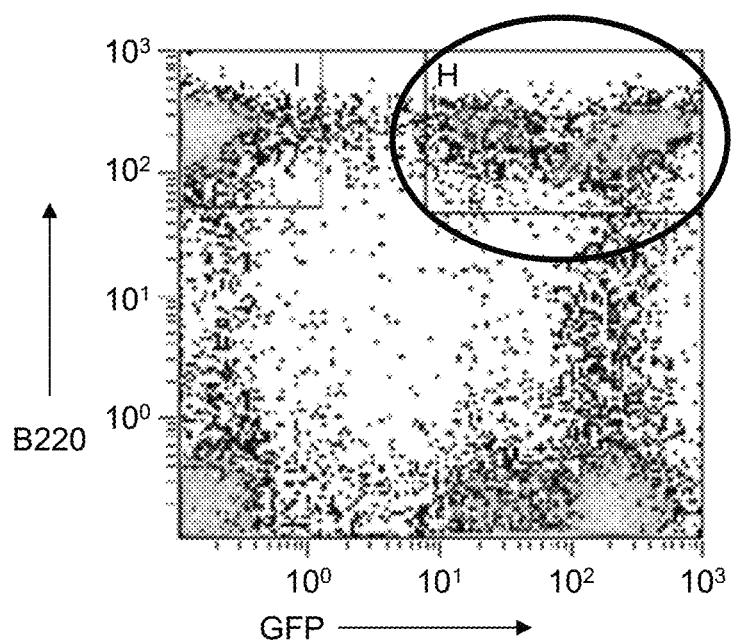
FIG. 24 shows the results of flow cytometry analysis of a chimeric mouse that was derived from an ES cell carrying IGHK-MAC and that mouse Igh and Igk were destroyed.

In addition, after blood samples are obtained from the chimeric mice, blood cells are fixed to prepare specimens, and FISH analysis is carried out using Human Cot-1 and Mouse minor satellite DNAs as probes. Thus, the cells carrying IGHK-MAC are identified at the chromosome level.
[A.3] Evaluation of Human IGM Expression in Chimeric Mice Derived from ES Cells Carrying IGHK-MAC In HKD31 mouse ES cells, mouse Igh and Igk genes have been destroyed. A mouse in which the antibody μ chain genes necessary for generation of B lymphocytes is knocked out is deficient in mature B lymphocytes that serve for the humoral immunity, and thus the mouse is incapable of antibody production. Accordingly, the HKD31 mouse ES cells cannot serve as mature B cells in chimeric mice. Concerning HKD31 mouse cells carrying IGHK-MAC that are used for preparation of chimeric mice, if human IGM is expressed from IGHK-MAC then such deficiency can be rescued, thereby enabling detection of GFP-positive B cells. Thus, the functional expression of the IGM gene on the IGHK-MAC can be proved indirectly. Blood was obtained from the chimeric mice, and mouse B cells are detected by using a flow cytometer and staying with an antibody to mouse CD45R (B220). By analyzing whether cells are co-positive for CD45R and GFP, it is possible to confirm the functional expression of the IGHK-MAC-derived IGM. Blood cells were stained with an antibody to mouse CD45R (B220) to confirm human IGM-, CD45R-, and GFP-positive cells. Peripheral blood was obtained, transferred into a tube containing heparin PBS, and subjected to inversion mixing, followed by ice cooling. After the blood was centrifuged at 2,000 rpm and 4° C. for 3 minutes, the supernatant was removed, various antibodies were added, the reaction was allowed to proceed at 4° C. for 30 minutes, and the resultant was washed with PBS supplemented with 5% fetal bovine serum (5% FBS/PBS). After the final centrifugation, 1.2% dextran/physiological saline was added to the pellet and, after tapping, the resultant was allowed to stand at room temperature for 45 minutes, so that red blood cells naturally precipitated. Then the supernatant was transferred to a new tube, centrifugation was carried out at 2,000 rpm and 4° C. for 3 minutes, the supernatant was removed, hemolytic agent (0.17 M NH$_4$Cl) was added to the pellet at room temperature, and then the resultant was allowed to stand for 5 minutes. The cells were centrifuged at 2,000 rpm and 4° C. for 3 minutes, washed with 5% FBS/PBS, and suspended in 500 µl of 5% FBS/PBS. The suspension, a sample for analysis, was analyzed by flow cytometry. For the peripheral lymphocytes of chimeric mice from HKD31 6TG-9 IGHK-MAC 14-7-9 #1, analyses were conducted in the manner described above. As a result, because GFP- and B220-positive cells were observed, the function of the constructed IGHK-MAC was suggested (FIG. 24).

[A.4] Detection of Human Antibody in Chimeric Mouse Serum

In order to confirm the expression of the human antibody gene light chain, the human antibody gene heavy chain, and various isotypes in chimeric mice, the human antibody concentration in the blood serum is determined by the enzyme linked immunosorbent assay (ELISA). ELISA is carried out in accordance with the method described in the following documents: Experimental Manual for Monoclonal Antibody, Toyama and Ando, Kodansha, 1987; Introduction of Experiment for Monoclonal Antibody, Ando and Chiba, Kodansha, 1991; Ultrasensitive Enzyme Immunoassays, Ishikawa, Gakkai Shuppan Center, 1993; Ed Harlow and David Lane, Antibodies: A Laboratory Manual, Cold Spring Harbor Laboratory, 1988; and A. Doyle and J. B. Griffiths, Cell & Tissue Culture: Laboratory Procedures, John Wiley & Sons Ltd., 1996. With reference to the methods described in these documents, the reaction time and temperature are improved so that they are carried out, for example, at 4° C. overnight, depending on assay systems. A certain type of antibody is detected using a kit. Expression of human antibodies (hγ, hµ, hκ, hγ1, hγ2, hγ3, hγ4, hα, hε, and hδ) and concentration thereof in serum are determined. Basic procedures are described below.

An antibody to a human immunoglobulin to be measured is diluted and an ELISA plate is coated therewith at 4° C. overnight. In assay of serum samples, PBS supplemented with 5% fetal bovine serum is used for dilution of blocking, samples, and a labelled antibody. After the coated plate is washed, blocking is conducted for at least 1 hour. After the plate is washed, the sample is added, and incubation is carried out for at least 30 minutes. After washing the plate, a diluted enzyme-labeled anti-human immunoglobulin antibody and a diluted mouse immunoglobulin antibody are added, incubation is carried out for at least 1 hour, the plate is washed, and a substrate solution is added to develop color. The assay system may be carried out using basically the same procedures, i.e. by using a biotin-labeled antibody, washing the plate, adding an avidin-enzyme complex and conducting incubation, washing the plate, and then adding a substrate solution. The absorbance is measured using a microplate reader. When the concentration in serum is to be assayed, the standard with known concentration is serially diluted to conduct ELISA at the same time as in assay of a sample, and analysis is conducted using a prepared calibration curve to determine the concentration.

[A.5] Expression Analysis and Sequence Identification of Human Antibody cDNA is synthesized from RNA derived from a chimeric rat spleen, and cloning and nucleotide sequence identification of a human antibody gene variable region can be performed in accordance with the methods disclosed in the patent literature (WO 98/37757).

[A.6] Evaluation of Response for Antigen-Specific Human Antibody Production

A chimeric mouse is evaluated for increase in antigen-specific human antibody titer. In accordance with the method disclosed in the patent literature (WO 98/37757), the chimeric mouse is immunized with human serum albumin to analyze an increase in the antibody titer.

[B] Transmission of IGHK-MAC to Offsprings from IGHK-MAC-Carrying Chimeric Mice

[B.1] Transmission of IGHK-MAC to Offsprings

The female chimeric mice produced in [A] above (chimeric rate: approximately 100%) are subjected to crossbreeding with male ICR mice, and the born pup mice are subjected to observation of GFP fluorescence indicating a dominant inheritance of ES cell-derived IGHK-MAC. Where the GFP fluorescence is observed, the transmission of IGHK-MAC to offsprings and the stable retention thereof in the mice can be confirmed. A mouse lineage in which IGHK-MAC has been transmitted to progeny is called "mTC (IGHK-MAC)."

A chimeric mouse derived from HKD31 6TG-9 IGHK-MAC 14-7-9 #1 (chimeric rate: 90% when determined by coat color) was repeatedly subjected to crossbreeding with a mouse (HKD) in which the Igh and Igk has been destroyed. As a result, 12 offspring mice were obtained, GFP fluorescence was observed in one individual among them, and the transmission of IGHK-MAC was confirmed in the individual (F1). This mouse lineage is called "HKD mTC (IGHK-MAC)." This F1 mouse is further subjected to crossbreeding with an HKLD mouse with a mutation of mouse Igλ low expression. As a result, 8 offspring mice were obtained, and the transmission of IGHK-MAC was observed in 3 offspring mice (F2).

A total of 12 chimeric mice with a high chimeric rate (>80%, when determined by coat color) derived from XO ES9 IGHK-MAC 8-1-1 #1 were subjected to crossbreeding. As a result of crossbreeding between 10 chimeric mice and HKD mice, 97 offspring mice were obtained, GFP fluorescence was observed in 32 individuals, and the transmission of IGHK-MAC to offsprings (F1) was confirmed. As a result of crossbreeding between 2 chimeric mice and HKLD mice, in addition, 18 offspring mice were obtained, GFP fluorescence was observed in 3 individuals, and the transmission of IGHK-MAC to offsprings (F1) was confirmed. As a result of crossbreeding between 3 F1 mice and HKD mice, the transmission of IGHK-MAC was observed in 10 individuals (F2) among 33 offspring mice. In addition, 4 F1 mice were subjected to crossbreeding with HLKD mice, and the transmission of IGHK-MAC to offspring was observed in 21 individuals (F2) among 40 offspring mice. Among the F2 mice in which IGHK-MAC has been transmitted, 12 individuals had the HKD genotype (i.e., HKD mTC (IGHK-MAC)).

[B.2] Confirmation of Retention of IGHK-MAC in IGHK-MAC-Carrying Mice

For the mTC (IGHK-MAC), the transmission of IGHK-MAC to offsprings can be confirmed in detail by analyzing the mTC (IGHK-MAC) in the same manner as in Example 7 [A.2]. As to offspring mice transmitted from XO ES9 IGHK-MAC 8-1-1 #1, PCR using their caudal DNA as a template was conducted, and GFP expression was confirmed in the mice. From the results, both the analyses indicated positive, and the transmission of IGHK-MAC to the offsprings and the stable retention thereof were confirmed.

[B.3] Evaluation of Human IGM Expression in IGHK-MAC-Carrying Mice

Figure 25:
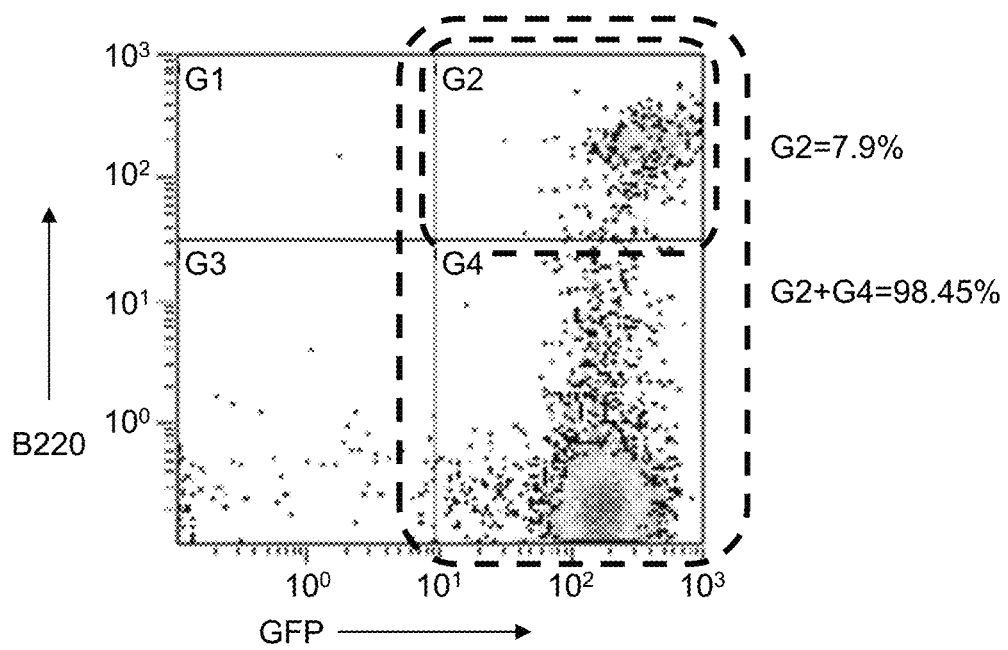
FIG. 25 shows the results of flow cytometry analysis of a mouse that was derived from mouse HKD31 6TG-9 cell carrying IGHK-MAC and that the Igh and Igk were destroyed.
Figure 26:
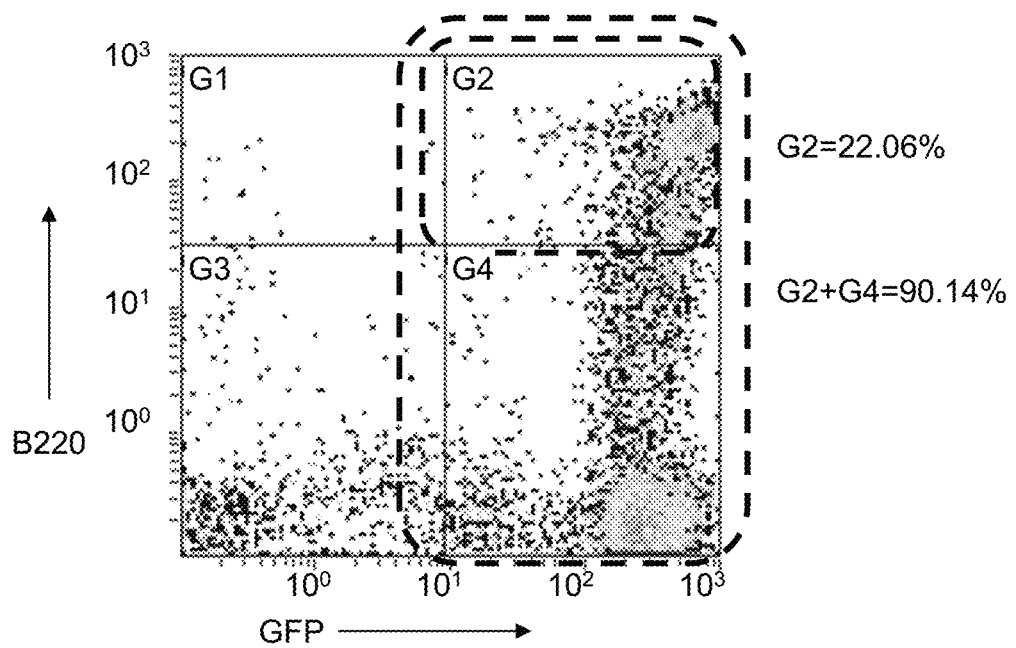
FIG. 26 shows the results of flow cytometry analysis of a mouse that was derived from mouse XO ES9 cell carrying IGHK-MAC and that the Igh and Igk were destroyed.

Mice were analyzed in the same manner as in Example 7 [A.3], and retention of IGHK-MAC and functions thereof in HKD mTC (IGHK-MAC) were indirectly evaluated. HKD mTC (IGHK-MAC) mice derived from HKD31 6TG-9 IGHK-MAC 14-7-9 #1 were subjected to PCR analysis using the caudal DNA as a template, peripheral blood lymphocytes were obtained from those found to exhibit positive results in PCR analysis, the peripheral blood lymphocytes were analyzed for the presence of GFP-positive cells and B220/GFP-co-positive cells. The results of analysis suggested that all the mice were positive for IGHK-MAC, that the transmitted IGHK-MAC was stably maintained, and the IGHK-MAC were functional. As a result of evaluation by flow cytometric analysis, the proportion of GFP-positive cells in peripheral blood lymphocytes (i.e., MAC-retaining cells) was found to be as high as 98.45%, and the proportion of B cells was 7.9% (FIG. 25). Also, with regard to HKD mTC (IGHK-MAC) mice in which IGHK-MAC was transmitted from XO ES9 IGHK-MAC8-1-1 #1, PCR analysis using the caudal DNA as a template was conducted to confirm that they were positive individuals, and, in their peripheral blood lymphocytes, the presence of GFP-positive cells and B220/GFP-co-positive cells was confirmed. The percentage of GFP-positive cells (MAC-carrying cells) in the peripheral blood lymphocytes was as high as 90.14%, and the percentage of B cells was 22.06% (FIG. 26).

[B.4] Evaluation of Human Antibody-Producing Capacity of IGHK-MAC-Carrying Mice mTC (IGHK-MAC) is evaluated in the same manner as in Example 7 [A.4], [A.5], and [A.6].

[C] Production of IGHK-MAC-Carrying Rats

IGHK-MAC-carrying rats are prepared and analyzed. Chimeric rats obtained in the process are also analyzed.

[C.1] Production of Chimeric Rats

Chimeric rats were produced using clone ES cells of the IGHK-MAC-carrying rats obtained in Example 6 in accordance with the method of Hirabayashi et al. (Mol. Reprod. Dev., 2010 February; 77 (2): 94.doi:10. 1002/mrd.21123). As hosts, blastocyst-stage embryos obtained by crossbreeding of female and male Crlj:WI rats (white, purchased from Charles River Laboratories Japan, Inc.) were used. Whether or not pup rats born through the transfer of injected embryos into surrogate mothers are chimeric can be evaluated based on their coat colors.

Figure 27:
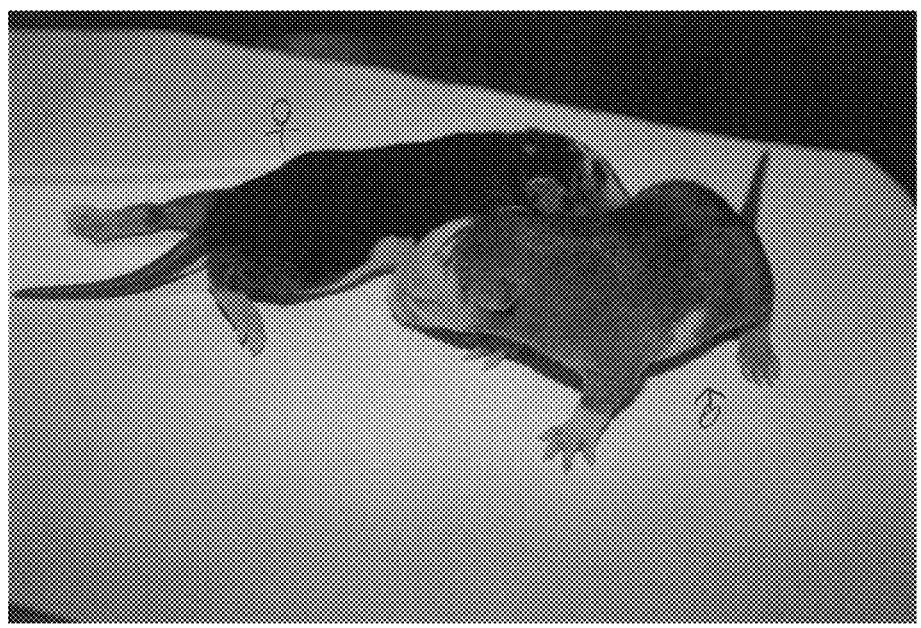
FIG. 27 shows images of chimera rats (males and females) derived from IGHK-MAC-carrying ES cells.

Rat ES (IGHK-MAC) 14-7 #4 and 8-1#3 cells (obtained in Example 6), which are IGHK-MAC-carrying ES cell clones, were injected into 25 and 18 embryos, which were then transferred into surrogate mothers, thereby obtaining 8 and 4 born chimeric rats (where dark brown color was in part observed in the coat color) (FIG. 27). GFP fluorescence indicating a dominant inheritance of ES cell-derived IGHK-MAC was also observed immediately after the birth. Thus, contribution of ES cells was confirmed.

[C.2] Confirmation of Retention of IGHK-MAC in Chimeric Rats Derived from IGHK-MAC-Carrying ES Cells Analysis is carried out in the same manner as in [A.2] above to confirm the retention of IGHK-MAC more precisely. Blood cells are subjected to FISH analysis using Human Cot-1 and Mouse Cot-1 DNAs as probes.

[C.3] Evaluation of Human Antibody-Producing Capacity of Chimeric Rats

Chimeric rats are evaluated in the same manner as in Example 7 [A.3], [A.4], [A.5], and [A.6].

[D] Transmission of IGHK-MAC to Offsprings from IGHK-MAC-Carrying Chimeric Rat

[D.1] Transmission of IGHK-MAC to Offsprings from IGHK-MAC-Carrying Chimeric Rat The chimeric rat produced in [C] above (chimeric rate: approximately 100%) was subjected to crossbreeding with a Crlj:WI rat, and the born pup rat was subjected to observation of GFP fluorescence indicating a dominant inheritance of IGHK-MAC derived from ES cells. Because GFP fluorescence was observed, the transmission of IGHK-MAC and the stable retention thereof therein were confirmed in the rat individuals. A rat lineage in which that the IGHK-MAC was transmitted is called "rTC (IGHK-MAC)." As a result of evaluation of a GFP-positive rate of peripheral blood lymphocytes in three F1 rats derived from rES8-1 #3, the transmitted IGHK-MAC was maintained at high retention rates of 98.23%, 96.62%, and 95.79%.

[D.2] Confirmation of Retention of IGHK-MAC in IGHK-MAC-Carrying Rats rTC (IGHK-MAC) is analyzed in the same manner as in [C.2] above, so that the transmission of IGHK-MAC to the offsprings can be confirmed in detail.

[D.3] Evaluation of Human Antibody-Producing Capacity of IGHK-MAC-Carrying Rat rTC (IGHK-MAC) is evaluated in the same manner as in Example 7 [A.3], [A.4], [A.5], and [A.6]. The rTC was subjected to ELISA analysis to detect human antibodies IgM and IgG. When wild-type rat serum was analyzed as a negative control, the presence of human IgM and IgG was observed in the rTC sera, indicating that the rTC produces human antibodies (FIG. 28).

Example 8

Modification of Human Chromosome 22

Figure 29:
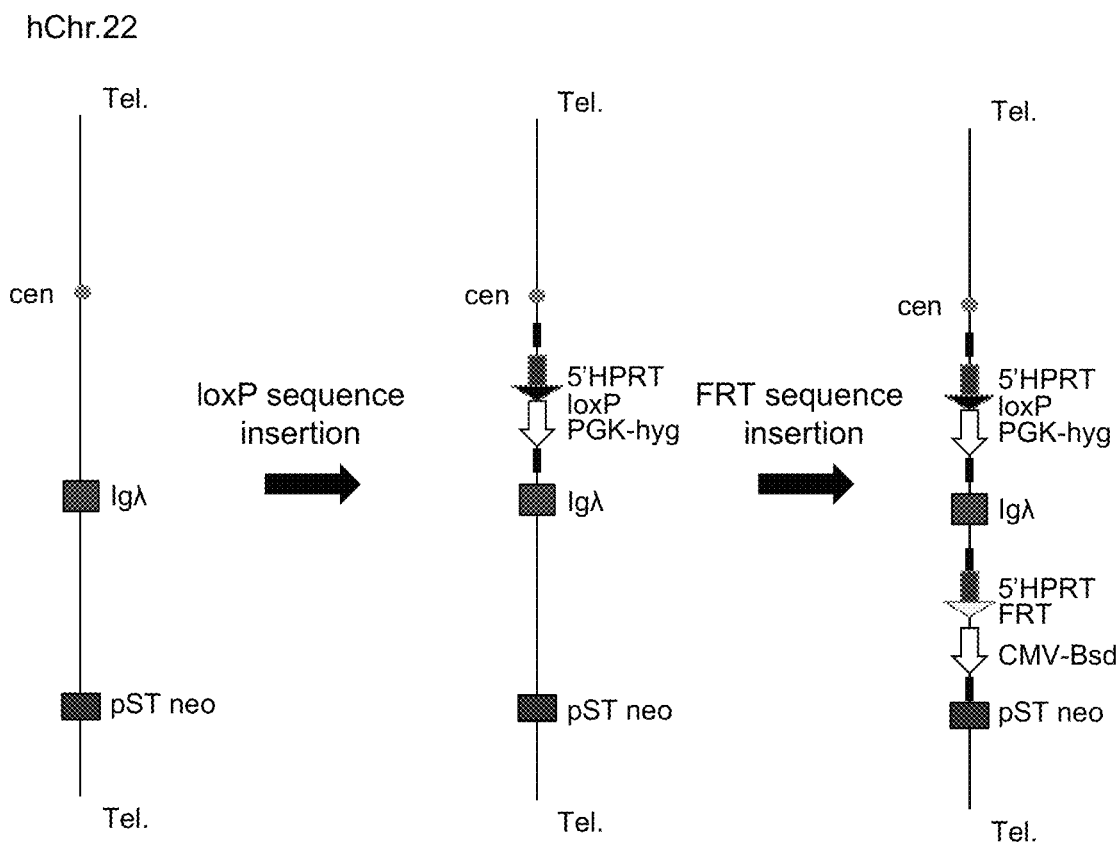
FIG. 29 shows the modification of human chromosome 22 comprising inserting a loxP sequence into a region on the centromere side and an FRT sequence into a region on the telomere side of the light chain λ gene on the human chromosome 22.

In order to clone the IGL and IGH regions into the mouse artificial chromosome vector MAC by translocation, the loxP site and the FRT site are inserted into human chromosome 22 (FIG. 29).

[A] Insertion of loxP Sequence into Human Chromosome 22

[A.1] Preparation of Vector for loxP Insertion into Human Chromosome 22

As a basic plasmid used for inserting the loxP sequence into the DT40 52-18#22 (#22) cell carrying human chromosome 22, pX6.1 (described above) was used. The DNA sequence of human chromosome 22 as a loxP insertion site was obtained from the GenBank database (NC_000022.11).

Genomic DNA extracted from DT40 (#22) was used as a template, and the target sequence of homologous recombination was amplified using primer sequences shown below.

HindIII553La L:
(SEQ ID NO: 54)
5'-TGTAGCTGACTTTAGCCACCCACAAGTAC-3'

AscI553La R:
(SEQ ID NO: 55)
5'-TCGAGGCGCGCCCTCAAACTCCTGGGTGTAAATGATCCTCCTGC-3'

KpnI553Ra L:
(SEQ ID NO: 56)
5'-TGAGGGTACCGTGCAGTAAAGTATGATTGAGC-3'

SalI553Ra R:
(SEQ ID NO: 57)
5'-TCGAGTCGACCTTGCTGATTATACCTCATCTCCTTCCCTC-3'

Figure 30:
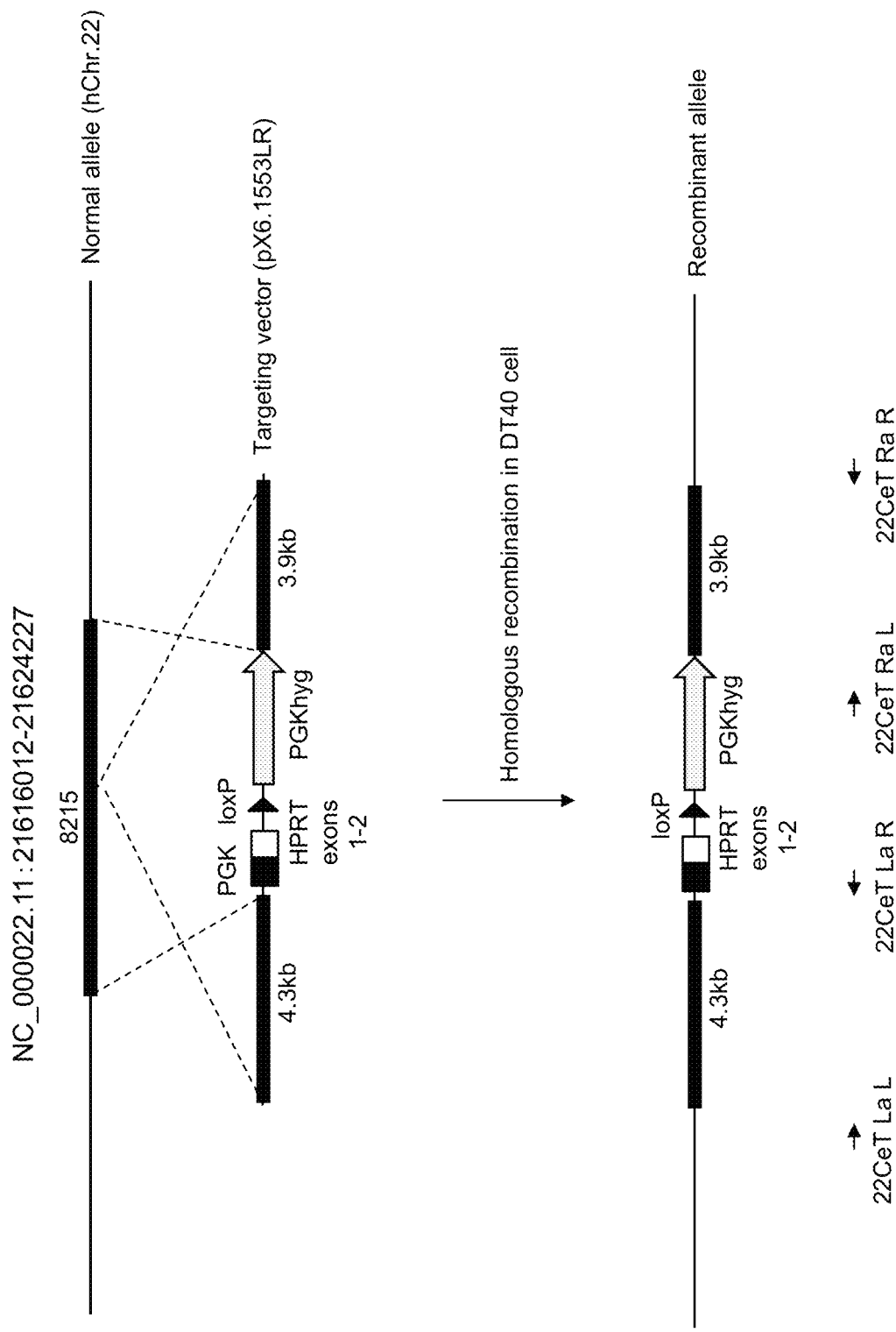
FIG. 30 shows the production of a loxP-inserted recombinant allele obtained by modifying the human chromosome 22 allele by homologous recombination using the targeting vector indicated.

PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 6 minutes was conducted for 30 cycles. The PCR products of HindIII553La L and AscI553La R were digested with HindIII (NEB) and AscI (NEB), separated and purified by agarose gel electrophoresis, and ligated to the protruding end formed by digestion of pX6.1 with HindIII and AscI (vector name: pX6.1553L). In addition, the PCR products of KpnI553Ra L and SalI553Ra R were digested with KpnI (NEB) and SalI (NEB), separated and purified by agarose gel electrophoresis, and ligated to the protruding end formed by digestion of pX6.1553L with KpnI and SalI (vector name: pX6.1553LR). FIG. 30 shows the targeting vector, the target sequence, and the chromosome allele obtained by homologous recombination.

[A.2] Insertion of loxP into Human Chromosome 22 in Chicken DT40 Cell

Chicken DT40 cells were cultured in RPMI 1640 culture medium (Gibco) supplemented with 10% fetal bovine serum (hereafter abbrebyted as FBS, Gibco), 1% chicken serum (Gibco), and 10-4 M 2-mercaptoethanol (Sigma). Approximately $10^7$ DT40 (#22) cells were washed once with additive-free RPMI 1640 culture medium and suspended in 0.5 ml of additive-free RPMI 1640 culture medium. The targeting vector pX6.1553LR (25 μg) linearized with the restriction enzyme NotI (NEB) was added thereto, the resultant was transferred into a cuvette (Bio-Rad Laboratories, Inc.) for electroporation, and the cuvette was allowed to stand at room temperature for 10 minutes. The cuvette was set on Gene Pulser (Bio-Rad Laboratories, Inc.) and voltage was applied under the conditions of 550 V and 25 μF. The cuvette was allowed to stand at room temperature for 10 minutes, the cell suspension was dispensed to twelve 96-well culture plates, and culture was then conducted for 24 hours. The culture medium was exchanged with a culture medium containing Hygromycin (1.0 mg/ml) (Wako, Osaka, Japan) and then subjected to selection culture for about 2 weeks. As a result, 32 drug-resistant cell clones were obtained.

[A.3] Selection of Homologous Recombinant

Genomic DNA was extracted from a hygromycin-resistant cell line and used as a template to select a recombinant. To this end, PCR was carried out using the primers shown below to confirm whether or not site-directed recombination had occurred on human chromosome 22. The primer sequences are shown below.

(SEQ ID NO: 58)
22CeT La L: 5'-CCTGCCTTCTTGTTTCAGCTCTCAACTG-3'

(SEQ ID NO: 59)
22CeT La R: 5'-GACGTGCTACTTCCATTTGTCACGTCCT-3'

(SEQ ID NO: 60)
22CeT Ra L: 5'-ATCCCCATGTGTATCACTGGCAAACTGT-3'

(SEQ ID NO: 61)
22CeT Ra R: 5'-ACACTTTAGTCCCTGTCCCCTCAACGAG-3'

PCR was carried out using TP600 thermal cycler (TAKARA), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

In addition, PCR was carried out to examine whether or not the human chromosome 22 region was also retained. The primer sequences are shown below.

(SEQ ID NO: 62)
553P-F: 5'-AGATCTCTTGAGCCCAGCAGTTTGA-3'

(SEQ ID NO: 63)
553P-R: 5'-TGAAGTTAGCCGGGGATACAGACG-3'

(SEQ ID NO: 64)
PPM1F L: 5'-AACGGCAGCCAAACCAAAGA-3'

(SEQ ID NO: 65)
PPM1F R: 5'-ACCAGGACTGGCTGGGCATA-3'

(SEQ ID NO: 66)
IGLVI-70 L: 5'-AGTCTGCGCTGACCCAGGAA-3'

(SEQ ID NO: 67)
IGLVI-70 R: 5'-TTGAGCCAGAGAAGCGGTCA-3'

(SEQ ID NO: 68)
GNAZ L: 5'-TCCACTTGGGGGTCTGCATT-3'

(SEQ ID NO: 69)
GNAZ R: 5'-TGGTGCTGAGCAGCTGTGTG-3'

(SEQ ID NO: 70)
LIF L: 5'-TGGGACTTAGGTGGGCCAGA-3'

(SEQ ID NO: 71)
LIF R: 5'-GCCTCCCCAAGAGCCTGAAT-3'

(SEQ ID NO: 72)
hVpreB1-F: 5'-TGTCCTGGGCTCCTGTCCTGCTCAT-3'

(SEQ ID NO: 73)
hVpreB1-Rm: 5'-GGCGGCGACTCCACCCTCTT-3'

(SEQ ID NO: 74)
hVpreB3-F: 5'-CACTGCCTGCCCGCTGCTGGTA-3'

(SEQ ID NO: 75)
hVpreB3-R: 5'-GGGCGGGGAAGTGGGGGAGAG-3'

(SEQ ID NO: 76)
hL5-F: 5'-AGCCCCAAGAACCCAGCCGATGTGA-3'

(SEQ ID NO: 77)
hL5-R: 5'-GGCAGAGGGAGTGTGGGGTGTTGTG-3'

(SEQ ID NO: 78)
344-F: 5'-ATCATCTGCTCGCTCTCTCC-3'

```
344-R:  5'-CACATCTGTAGTGGCTGTGG-3'
                                        (SEQ ID NO: 79)

350P-F:  5'-ACCAGCGCGTCATCATCAAG-3'
                                        (SEQ ID NO: 80)

350P-R:  5'-ATCGCCAGCCTCACCATTTC-3'
                                        (SEQ ID NO: 81)

IgL-F:  5'-GGAGACCACCAAACCCTCCAAA-3'
                                        (SEQ ID NO: 82)

IgL-Rm:  5'-GAGAGTTGGAGAAGGGGTGACT-3'
                                        (SEQ ID NO: 83)

SERPIND1 L:  5'-ACCTAGAGGGTCTCACCTCC-3'
                                        (SEQ ID NO: 84)

SERPIND1 R:  5'-CCCTGGACATCAAGAATGG-3'
                                        (SEQ ID NO: 85)
```

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute was conducted for 35 cycles.

As a result, 17 PCR-positive clones were detected.

[A.4] Two-Color FISH Analysis

From among the clones detected above, 10 clones were selected at random and subjected to two-color FISH analysis according to Matsubara et al. (FISH experimental protocol, Shujunsha Co., Ltd., 1994). FISH analysis was carried out using Human cot-1 DNA and pX6.1 as probes. As a result, one copy of human chromosome 22 was retained and a PGKhygloxP5'HPRT-derived signal was observed in 70% or more of 9 clones, but no signal was detected on the human chromosome 22 as a negative control before site-directed insertion of PGKhygloxP5'HPRT.

Figure 31:
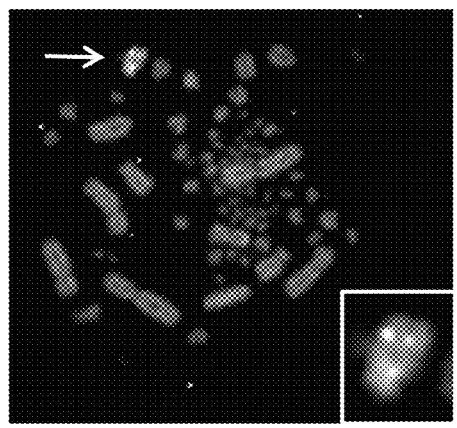
FIG. 31 is a figure obtained by two-color FISH analysis, indicating site-directed insertion of PGKhygloxP5'HPRT (indicated by an arrow) into human chromosome 22.

Thus, site-directed insertion of PGKhygloxP5'HPRT was confirmed (FIG. 31). The 2 clones 22DT40 KloxP3 1-5 and 22DT40 KloxP3 2-1 were subjected to the subsequent experiment.

[B] Insertion of FRT Site into loxP-Carrying Human Chromosome 22

For cloning of the IGL region of the human chromosome 22 and the IGH region of the human chromosome 14 into MAC with the aid of loxP by translocation, the FRT site is inserted into human chromosome 2 into which loxP has been inserted.

[B.1] Preparation of Vector for FRT Insertion into Human Chromosome 22

As a basic plasmid for inserting the FRT sequence in DT40 (#22), pMA-kD9FRTBsd was used. The DNA sequence of human chromosome 22 as a loxP insertion site was obtained from the GenBank database (NC_000022.11). Genomic DNA extracted from DT40 (#22) was used as a template, and the target sequence of homologous recombination was amplified using primer sequences shown below.

```
BamHISL350La L:
                                        (SEQ ID NO: 86)
5'-TCGAGGATCCGGCCTCCCAAAGGATTATAGACGTGAGCCACTGT-3'

AscISL350La R:
                                        (SEQ ID NO: 87)
5'-TCGAGGCGCGCCGGCACCTCTCCTATTTTCTTCACAGCACTT-3'

AscISL350Ra L:
                                        (SEQ ID NO: 88)
5'-TCGAGGCGCGCCAGCATGGTGGCCCGCACGTATAGTCGCAGCTA-3'

NotISL350Ra R:
                                        (SEQ ID NO: 89)
5'-TCGAGCGGCCGCAAAGAAGGGGCCCGCCTCTGCCTCTAAATCCTGA
C-3'
```

Figure 32:
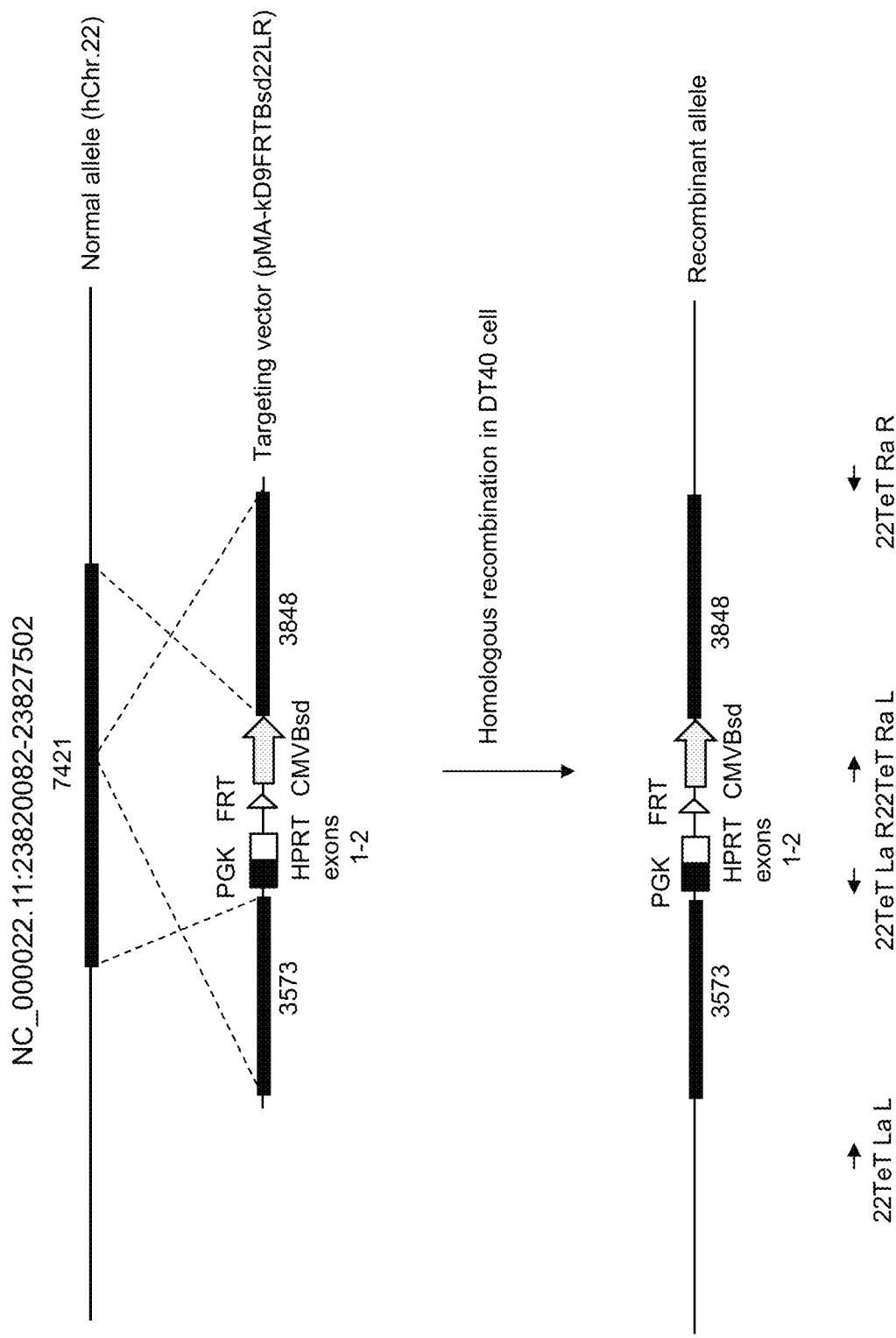
FIG. 32 shows the procedure of inserting an FRT site into the human chromosome 22 allele by homologous recombination using the targeting vector indicated.

PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 30 cycles. The PCR products of BamHISL350La L and AscISL350La R were digested with BamHI (NEB) and AscI (NEB), separated and purified by agarose gel electrophoresis, and ligated to the protruding end formed by digestion of pMA-kD9FRTBsd with BamHI and AscI (vector name pMA-kD9FRTBsd22L:). In addition, the PCR products of AscISL350Ra L and NotISL350Ra R were digested with MluI (NEB) and NotI (NEB), separated and purified by agarose gel electrophoresis, and ligated to the protruding end formed by digestion of pMA-kD9FRTBsd22L with AscI and NotI (vector name: pMA-kD9FRTBsd22LR). FIG. 32 shows the targeting vector, the target sequence, and the chromosome allele obtained by homologous recombination.

[B.2] Insertion of FRT into loxP-Carrying Human Chromosome 22 in Chicken DT40 Cell Chicken DT40 cells were cultured in RPMI 1640 culture medium (Gibco) supplemented with 10% fetal bovine serum (hereafter abbrebyted as FBS, Gibco), 1% chicken serum (Gibco), and 10-4 M 2-mercaptoethanol (Sigma). Approximately $10^7$ 22DT40 KloxP3 1-5 and 22DT40 KloxP3 2-1 cells were washed once with additive-free RPMI 1640 culture medium and suspended in 0.5 ml of additive-free RPMI 1640 culture medium. The targeting vector pMA-kD9FRTBsd22LR (25 µg) linearized with the restriction enzyme NotI (NEB) was added thereto, the resultant was transferred into a cuvette (Bio-Rad Laboratories, Inc.) for electroporation, and the cuvette was allowed to stand at room temperature for 10 minutes. The cuvette was set on Gene Pulser (Bio-Rad Laboratories, Inc.) and voltage was applied under the conditions of 550 V and 25 µF. The cuvette was allowed to stand at room temperature for 10 minutes, the cell suspension was dispensed to twelve 96-well culture plates, and culture was then conducted for 24 hours.

Drug selection was carried out with the aid of 15 µg/ml blasticidin (Funakoshi) and genomic DNA of blasticidin-resistant cell was extracted. In order to select recombinants with the use thereof as templates, PCR was carried out using the primers shown below, and whether or not site-directed recombination had occurred on human chromosome 22 was examined. The primer sequences are shown below.

```
                                        (SEQ ID NO: 90)
22TeT La L:  5'-TGCAGGTATCTGTTGGTGTCCCTGTTTT-3'

(SEQ ID NO: 91)
22TeT La R:  5'-GACGTGCTACTTCCATTTGTCACGTCCT-3'
```

-continued

22TeT Ra L: 5'-AGCAGAGCTCGTTTAGTGAACCGTCAGA-3'
(SEQ ID NO: 92)

22TeT Ra R: 5'-CTGTCCTATCCTTGCAGCTGTCTTCCAG-3'
(SEQ ID NO: 93)

PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles. Thus, recombination was confirmed.

The primers used to confirm whether or not the loxP insertion site was maintained are shown below.
22CeT La L (described above)
22CeT La R (described above)
22CeT Ra L (described above)
22CeT Ra R (described above)

PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

In addition, PCR was carried out to examine whether or not the human chromosome 22 region was also maintained. The primer sequences are shown below.
553P-F (described above)
553P-R (described above)
PPM1F L (described above)
PPM1F R (described above)
IGLVI-70 L (described above)
IGLVI-70 R (described above)
GNAZ L (described above)
GNAZ R (described above)
LIF L (described above)
LIF R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)
SERPIND1 L (described above)
SERPIND1 R (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute was conducted for 35 cycles. Among 24 drug-resistant clones of 22DT40 KloxP3 1-5 and those of 22DT40 KloxP3 2-1, respectively, 21 and 16 clones were found to be PCR-positive, respectively. On the basis of the results, 5 clones each were selected and subjected to the subsequent experiment.

[B.3] Two-Color FISH Analysis

Figure 33:
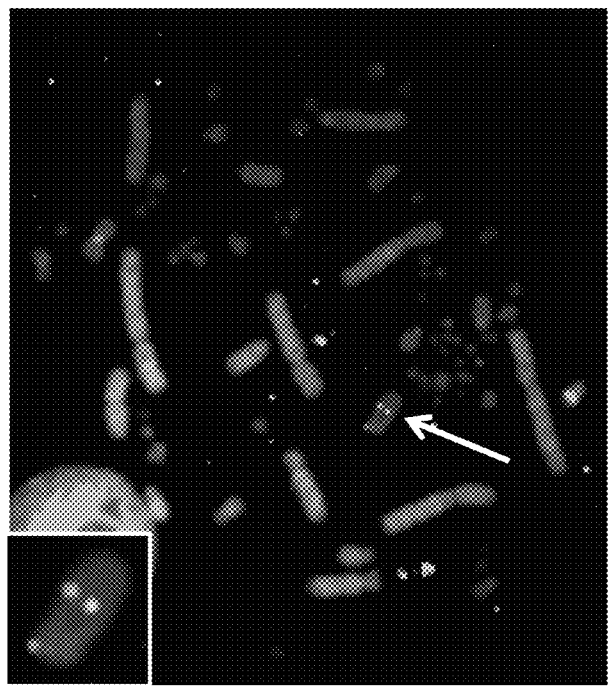
FIG. 33 is a figure obtained by two-color FISH analysis, indicating site-directed insertion of PGK5'HPRTFRTBsd (indicated by an arrow) into human chromosome 22.

FISH analysis was carried out using Human cot-1 DNA and pMA-kD9FRTBsd as probes. One copy of human chromosome 22 was retained and a PGK5'HPRTFRTBsd-derived signal was detected at high frequency, but no signal was detected on the human chromosome 2 as a negative control before site-directed insertion of PGK5'HPRTFRTBsd. Thus, site-directed insertion of PGK5'HPRTFRTBsd was confirmed (FIG. 33). The three clones 22DT40 KL3F1-5#2-1, 22DT40 KL3F2-1#1-2, and 22DT40 KL3F2-1 #1-3 were subjected to the subsequent experiment.

Example 9

Figure 34:
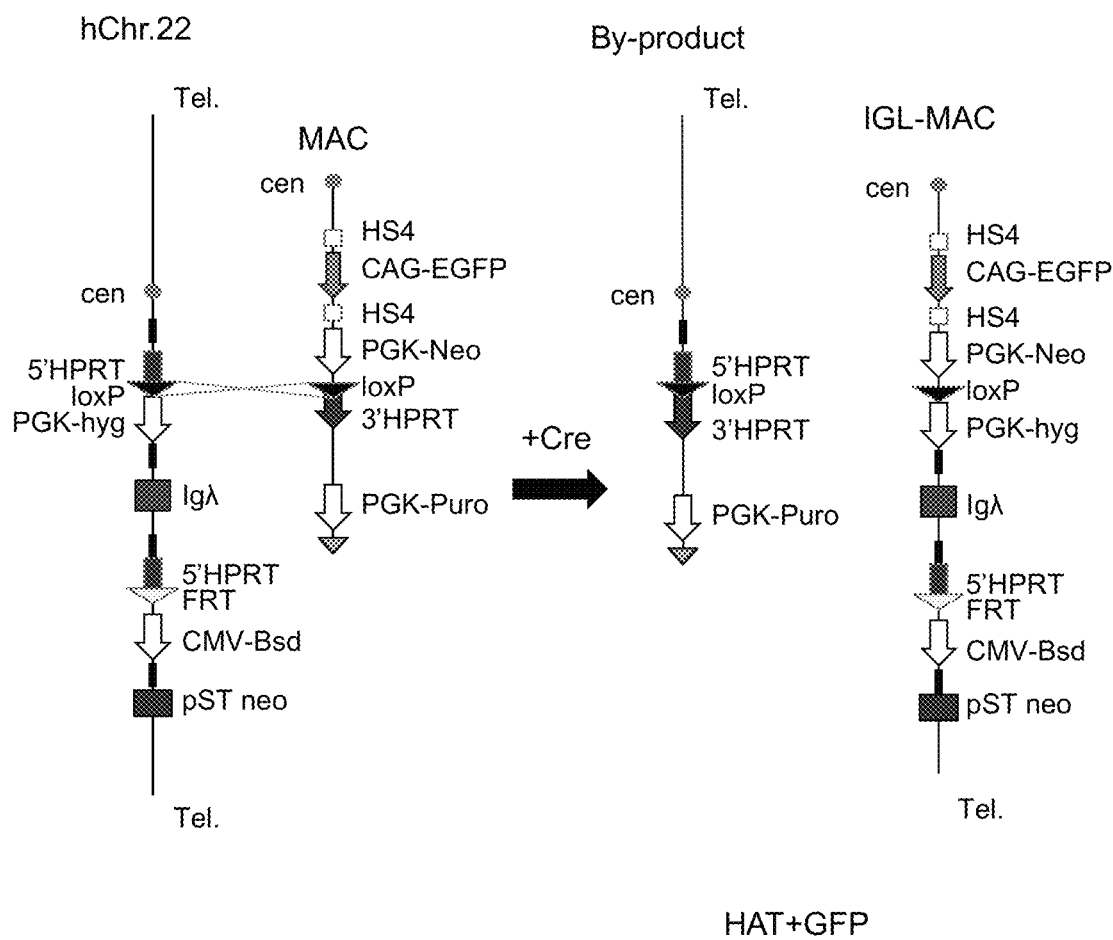
FIG. 34 shows the production of IGL-MAC by cloning the IGL region of human chromosome 22 into the MAC by translocation using the Cre/loxP system.

Incorporating Human Chromosome 22 Region into Mouse Artificial Chromosome (MAC) Vector by Translocation Cloning (FIG. 34)

[A] Chromosome Transfer of Modified Human Chromosome 22 into MAC-Carrying CHO Cell (CHO MAC)

For cloning of the human chromosome 22 region into MAC by translocation using the Cre/Lox system in CHO, the modified human chromosome 22 is transferred into an MAC-carrying CHO cell.

[A.1] Microcell Fusion and Isolation of Drug Resistant Clone

DT40 carrying the modified human chromosome 22 as a donor cell was subjected to microcell fusion to CHO (HPRT$^-$) as a CHO hprt-deficient cell carrying the MAC vector (obtained from the Health Science Research Resources Bank; Registration number: JCRB0218).

When the donor cells reached confluency, the cells were incubated for 12 hours with the addition of 20% FBS and 0.025 µg/ml colcemid to form microcells, the cells were recovered and suspended in a serum-free DMEM medium, the resulting cell suspension was put in a centrifuge flask coated with poly-L lysine (Wako), incubation was carried out for 30 minutes, and the cells were allowed to adhere to the flask. The serum-free DMEM medium was removed, the centrifuge flask was filled with a cytochalasin B (10 µg/ml, Sigma) solution kept warm at 37° C. in advance, and centrifugation was then carried out at 34° C. and 8,000 rpm for 1 hour. The microcells were suspended in the serum-free DMEM medium and purified using 8-µm, 5-µm, and 3-µm filters. The purified microcells were suspended in 2 ml of a solution of 0.05 mg/ml PHA-P (Sigma) in DMEM, the culture medium was removed from the cell suspension, and the resultant was then added to the recipient CHO MAC cells that had reached confluency in a 6-cm cell culture dish. After incubation was carried out for 15 minutes, the microcells were allowed to adhere to the CHO cells. Thereafter, cell fusion was carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells were washed 4 times with 5 ml of serum-free DMEM to remove PEG, and the CHO culture solution was then added. The cells were seeded in ten 10-cm cell culture dishes 24 hours later, 800 µg/ml G418 (Promega) and 8 µg/ml blasticidin were added, and selection culture was then conducted for 10 days. The donor cells 22DT40 KL3F 1-5 #2-1, 22DT40 KL3F 2-1 #1-2, and 22DT40 KL3F 2-1 #1-3 were subjected to reactions twice, and 2, 10, and 12 drug-resistant clones were obtained, respectively. It was confirmed by fluorescence that the EGFP expression cassette was incorporated in the MAC, and that the MAC was retained in the drug-resistant clones.

[A.2] Selection of Drug Resistant Clones by PCR Analysis

In order to confirm that the modified human chromosome 22 had been transferred into the CHO MAC cell line, DNAs of the drug resistant clones were extracted and used as templates to perform PCR analysis.

The primers used to confirm whether or not the loxP insertion site was maintained are shown below.
- 22CeT La L (described above)
- 22CeT La R (described above)
- 22CeT Ra L (described above)
- 22CeT Ra R (described above)

PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

The primers used to confirm whether or not the FRT insertion site was maintained are shown below.
- 22TeT La L (described above)
- 22TeT La R (described above)
- 22TeT Ra L (described above)
- 22TeT Ra R (described above)

PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, s the cycle of 98° C. for 15 seconds and 68° C. for 5 minutes was conducted for 35 cycles.

In addition, PCR was carried out to examine whether or not the human chromosome 22 region was also maintained. The primer sequences are shown below.
- 553P-F (described above)
- 553P-R (described above)
- PPM1F L (described above)
- PPM1F R (described above)
- IGLVI-70 L (described above)
- IGLVI-70 R (described above)
- GNAZ L (described above)
- GNAZ R (described above)
- LIF L (described above)
- LIF R (described above)
- hVpreB1-F (described above)
- hVpreB1-Rm (described above)
- hVpreB3-F (described above)
- hVpreB3-R (described above)
- hL5-F (described above)
- hL5-R (described above)
- 344-F (described above)
- 344-R (described above)
- 350P-F (described above)
- 350P-R (described above)
- IgL-F (described above)
- IgL-Rm (described above)
- SERPIND1 L (described above)
- SERPIND1 R (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute was conducted for 35 cycles. As a result, 2, 9, and 12 clones derived from 22DT40 KL3F 1-5 #2-1, 22DT40 KL3F 2-1 #1-2, and 22DT40 KL3F 2-1 #1-3 were found to be PCR-positive. On the basis of the results, 6 PCR-positive clones were selected and subjected to the subsequent experiment.

[A.3] Two-Color FISH Analysis

Figure 35:
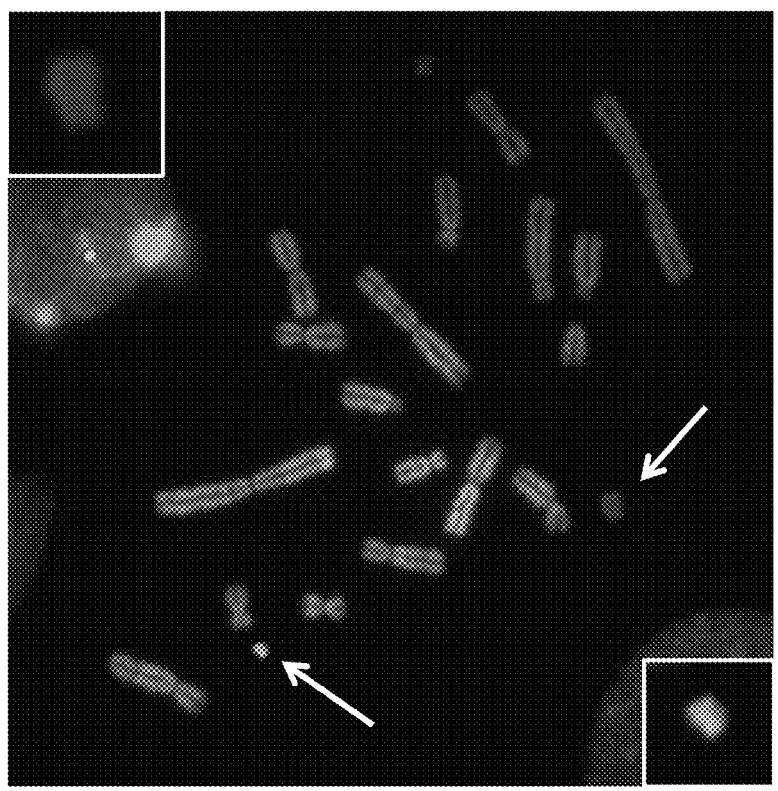
FIG. 35 is a figure obtained by two-color FISH analysis, indicating that the MAC (indicated by a left arrow) and the modified human chromosome 22 (indicated by a right arrow) are independently comprised in a CHO cell.

The PCR-positive clones were subjected to FISH analysis using Human cot-1 DNA and Mouse cot-1 DNA as probes, and positive cells, in which the MAC and the modified human chromosome 22 were independently carried, were selected. As a result of analysis (FIG. 35), the 2 clones CHO(MAC1)KL3F#2-2 and CHO(MAC1)KL3F#3-1 were subjected to the subsequent experiment.

[B] Cloning of MAC into Human Chromosome 22 Region by Translocation

Using the Cre/Lox system, a human chromosome 22 fragment containing the IGL region is translocated to MAC.

[B.1] Obtaining HAT-Resistant Recombinant Chromosome by Cre Expression

MAC comprises a loxP site inserted therein, which site could cause recombination with a loxP site of the modified human chromosome 22 in the presence of Cre recombinase. When recombination takes place, 5'HPRT in the human chromosome 22 region as a by-product that is not inserted in the MAC, is ligated to 3'HPRT at the terminus of the MAC as a by-product, thereby resulting I reconstruction of the HPRT gene, and CHO(hprt-/-) acquires HAT resistance.

When CHO(hprt-/-) carrying the modified human chromosome 22 and MAC reached confluency in a 10-cm cell culture dish, 18 μg of a Cre expression plasmid (vector name: pBS185) was added using Lipofectamine 2000 (Thermo Fisher Scientific) with reference to the manufacturer's instructions. The culture medium was exchanged with a fresh culture medium 6 hours after the addition, the cells were seeded in ten 10-cm cell culture dishes, and drug selection was then carried out using 1× HAT (Sigma) and 8 μg/ml blasticidin.

The 24 and 22 HAT resistant clones of CHO(MAC1) KL3F#2-2 and CHO(MAC1)KL3F#3-1 were subjected to the subsequent analysis.

[B.2] Selection of Drug Resistant Clones by PCR Analysis

Genomic DNA extracted from HAT resistant cells was used as a template, PCR was carried out using the primers shown below in order to select clones in which reciprocal translocation occurred, and whether or not reciprocal translocation had occurred between the human chromosome 22 fragment and the MAC was examined. The primer sequences are shown below.
- TRANS L1 (described above)
- TRANS R1 (described above)
- KJneo (described above)
- PGKr-2 (described above)

PCR was carried out using the primers described above, LA taq (Takara), and buffers and dNTPs (dATP, dCTP, dGTP, and dTTP) included in the kit under the recommended conditions. Temperature and cycle conditions were as follows: after thermal denaturation at 98° C. for 1 minute, the cycle of 94° C. for 10 seconds, 60° C. for 30 seconds, and 72° C. for 3 minutes was conducted for 30 cycles.

The primers used to confirm whether or not the FRT insertion site was maintained are shown below.
- 22TeT La L (described above)
- 22TeT La R (described above)

22TeT Ra L (described above)
22TeT Ra R (described above)
PCR was carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions were as follows: after thermal denaturation at 98° C. for 1 minute, the cycle of 98° C. for 15 seconds and 68° C. for 5 minutes was conducted for 35 cycles.

The human chromosome 22 region was subjected to PCR analysis. The sequences are shown below.

553P-F (described above)
553P-R (described above)
PPM1F L (described above)
PPM1F R (described above)
IGLVI-70 L (described above)
IGLVI-70 R (described above)
GNAZ L (described above)
GNAZ R (described above)
LIF L (described above)
LIF R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)
SERPIND1 L (described above)
SERPIND1 R (described above)

PCR was carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute was conducted for 35 cycles. As a result, 17 and 7 clones of CHO(MAC1)KL3F#2-2 and CHO(MAC1)KL3F#3-1 were found to be positive, respectively, 6 and 4 clones were selected therefrom, respectively, and the selected clones were subjected to the subsequent experiment.

[B.3] Two-Color FISH Analysis

Figure 36:
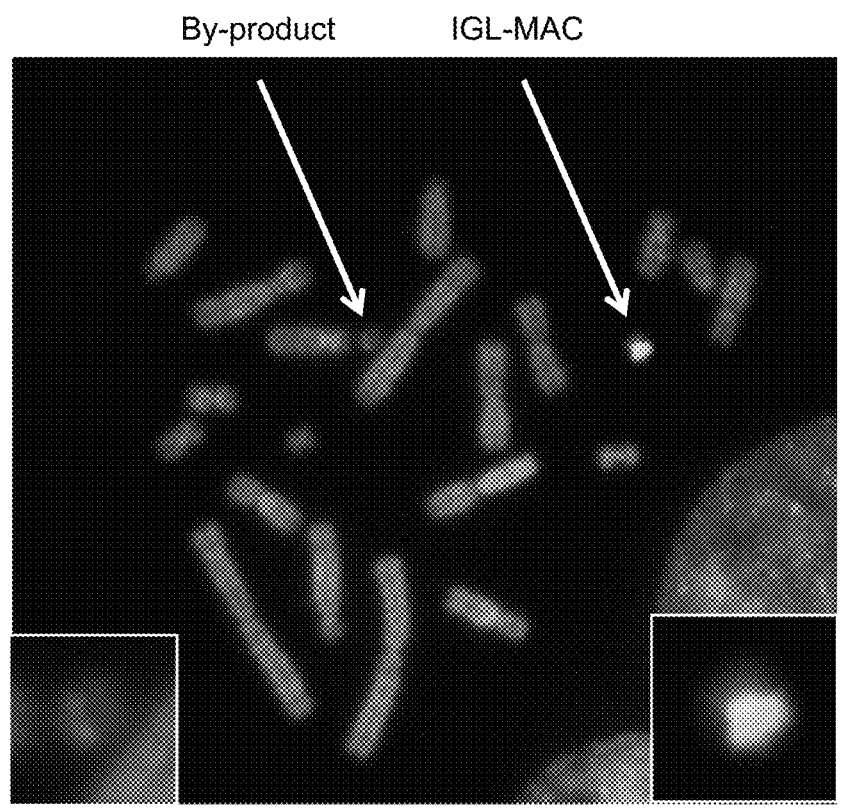
FIG. 36 is a figure obtained by two-color FISH analysis, indicating that the IGL-MAC, in which the IGL region has been carried in the MAC (indicated by a right arrow), and a by-product (indicated by a left arrow) are independently comprised.

The selected clones were subjected to FISH analysis using Human cot-1 DNA and Mouse cot-1 DNA as probes, and it was confirmed that reciprocal translocation occurred between MAC and the modified human chromosome 2 and that IGK-MAC, in which the IGL region was inserted in the MAC, and a by-product were independently retained (FIG. 36). The selected 2 positive clone cells (designated as "CHO IGL-MAC") were subjected to the subsequent experiment.

Example 10

Figure 37:
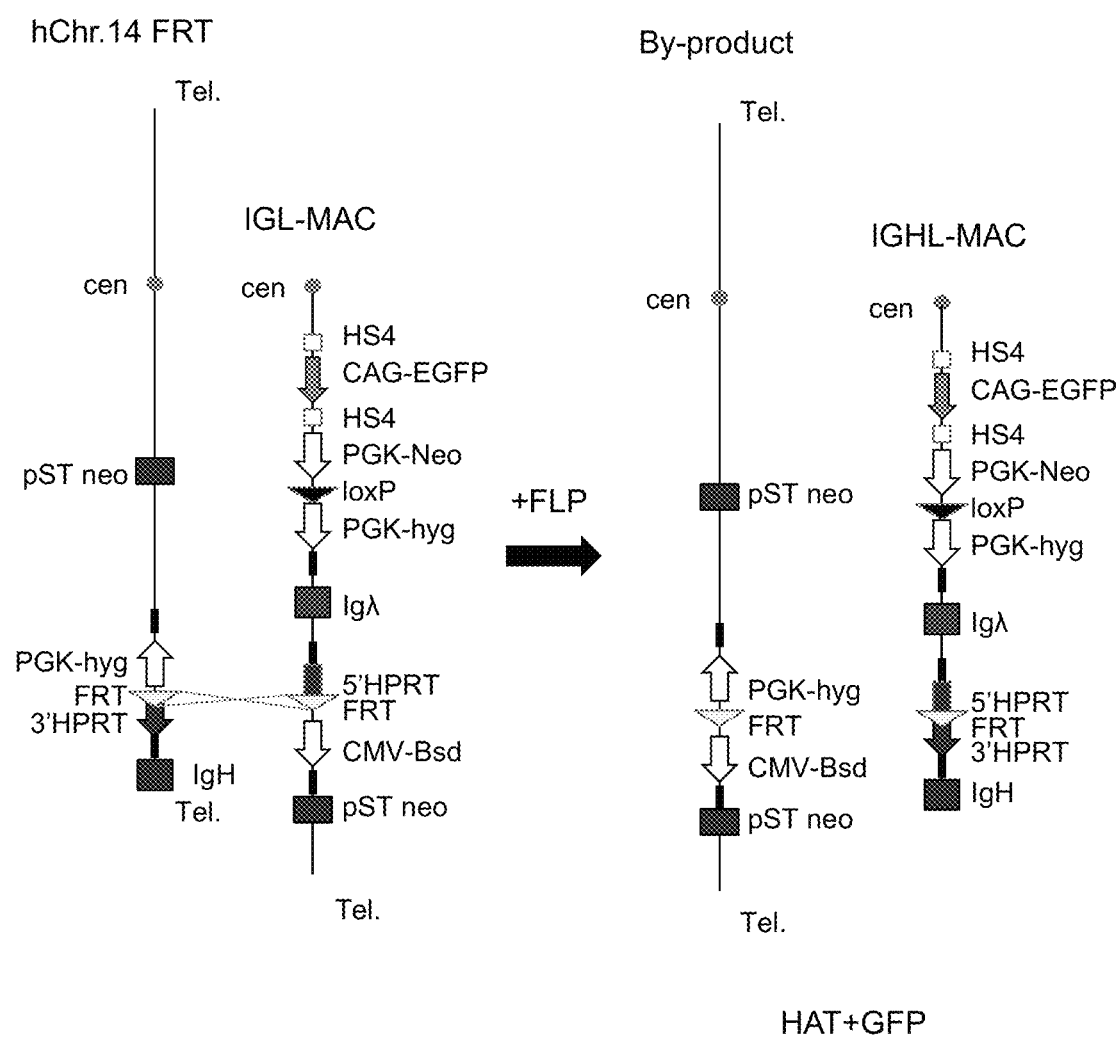
FIG. 37 shows the procedure of producing the IGHL-MAC in which the IGH region is comprised in the IGL-MAC.

Incorporating IGH Region of Human Chromosome 14 into IGL-MAC by Reciprocal Translocation The prepared IGL-MAC is transferred into the CHO (hprt−/−) cell line carrying the modified human chromosome 14, so as to incorporate the IGH region on IGL-MAC by recombination using the FRT/Flp system. Thus, IGHL-MAC is prepared (FIG. 37).

[A] Transfer of IGL-MAC into CHO CHO (hprt−/−) Cell Line Carrying Modified Human Chromosome 14

[A.1] Microcell Fusion and Isolation of Drug Resistant Clone

The donor cell (CHO IGL-MAC) is cultured in a cell culture dish, the culture medium was exchanged with an F12 medium supplemented with 20% FBS and 0.1 µg/ml colcemid when the cells reached confluency, the culture medium is further exchanged with a fresh F12 medium supplemented with 20% FBS and 0.1 µg/ml colcemid 48 hours after the initiation of culture, and the culture is incubated overnight to form microcells. The culture medium was removed, the centrifuge flask is filled with a cytochalasin B (10 µg/ml, Sigma) solution kept warm at 37° C. in advance, and centrifugation is then carried out at 34° C. and 8,000 rpm for 1 hour. Microcells are suspended in the serum-free DMEM medium and purified using 8-µm, 5-µm, and 3-µm filters. Thereafter, the microcells are suspended in 2 ml of a solution of 0.05 mg/ml PHA-P (Sigma) in DMEM, the culture solution is removed from the cell suspension, and the resultant is then added to the recipient CHO hprt−/− 14FRT #3-17_8 and CHO hprt−/− 14FRT #3-17_14 cells that have reached confluency in 6-cm cell culture dishes. After incubation is carried out for 15 minutes, the microcells are allowed to adhere to the CHO cells. Thereafter, cell fusion is carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells are washed 4 times with 5 ml of serum-free DMEM to remove PEG, and the CHO culture solution is then added. The cells are seeded in ten 10-cm cell culture dishes 24 hours later, 800 µg/ml G418 and 8 µg/ml blasticidin are added thereto, and selection culture is then conducted for 10 days. The resulting drug-resistant clones were subjected to the subsequent analysis.

[A.2] Selection of Drug Resistant Clones by PCR Analysis

PCR is carried out to examine whether or not IGL-MAC have been transferred into the CHO (hprt−/−) cell line carrying the modified human chromosome 14 and whether or not the modified human chromosome 14 have been maintained. The primers used are shown below.

KJneo (described above)
PGKr-2 (described above)

PCR is carried out using the primers described above, LA taq (Takara), and buffers and dNTPs (dATP, dCTP, dGTP, and dTTP) included in the kit under the recommended conditions. Temperature and cycle conditions are as follows: after thermal denaturation at 98° C. for 1 minute, the cycle of 94° C. for 10 seconds, 60° C. for 30 seconds, and 72° C. for 3 minutes is conducted for 30 cycles.

The primers used to confirm whether or not the FRT insertion site is maintained are shown below.

22TeT La L (described above)
22TeT La R (described above)
22TeT Ra L (described above)
22TeT Ra R (described above)

PCR is carried out using TP600 thermal cycler (Takara), KOD FX enzyme (TOYOBO), and buffers and dNTPs (dATP, dCTP, dGTP, and dTTP) included in the kit under the recommended conditions. Temperature and cycle conditions are as follows: after thermal denaturation at 98° C. for 1 minute, the cycle of 98° C. for 15 seconds and 68° C. for 5 minutes for 35 cycles.

The human chromosome 22 region is also subjected to PCR using the sequences shown below.
- 553P-F (described above)
- 553P-R (described above)
- PPM1F L (described above)
- PPM1F R (described above)
- IGLVI-70 L (described above)
- IGLVI-70 R (described above)
- GNAZ L (described above)
- GNAZ R (described above)
- LIF L (described above)
- LIF R (described above)
- hVpreB1-F (described above)
- hVpreB1-Rm (described above)
- hVpreB3-F (described above)
- hVpreB3-R (described above)
- hL5-F (described above)
- hL5-R (described above)
- 344-F (described above)
- 344-R (described above)
- 350P-F (described above)
- 350P-R (described above)
- IgL-F (described above)
- IgL-Rm (described above)
- SERPIND1 L (described above)
- SERPIND1 R (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute is conducted for 35 cycles.

Primers for Confirmation of Human Chromosome 14 Region:
- MTA1-F3 (described above)
- MTA1-R3 (described above)
- ELK2P2-F (described above)
- ELK2P2-R (described above)
- g1(g2)-F (described above)
- g1(g2)-R (described above)
- VH3-F (described above)
- VH3-R (described above)
- CH3F3 (described above)
- CH4R2 (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 60° C. for 30 seconds or 56° C. for 30 seconds, and 72° C. for 1 minute is conducted for 35 cycles.

Primers for Confirmation of FRT Insertion Site on Modified Human Chromosome 14:
- 14TarC_La F (described above)
- 14TarC_La R (described above)
- 14TarC_Ra F (described above)
- 14TarC_Ra R (described above)

PCR is carried out using the primers described above, KOD FX (TOYOBO), and buffers and dNTPs (dATP, dCTP, dGTP, and dTTP) included in the kit under the recommended conditions. Temperature and cycle conditions are as follows: after thermal denaturation at 98° C. for 1 minute, the cycle of 98° C. for 15 seconds and 68° C. for 6 minutes is conducted for 35 cycles.

The selected PCR-positive clones were subjected to the subsequent experiment.

[A.3] Two-Color FISH Analysis

The selected clones are subjected to FISH analysis using Human cot-1 DNA and Mouse cot-1 DNA as probes to confirm a clone in which one copy of IGL-MAC and one copy of the modified human chromosome 14 are independently maintained. The positive cells are selected (designated as "CHO #14 IGL-MAC") and subjected to the subsequent experiment.

[B] Construction of IGHL-MA Using FRT/Flp Recombination System

IGL-MAC and the modified human chromosome 14 are subjected to reciprocal translocation using the FRT/Flp system to clone the IGH region derived from human chromosome 14 into IGL-MAC by translocation. Thus, IGHL-MAC is constructed.

[B.1] Obtaining HAT Resistant Recombinant Chromosome by FLP Expression

The FRT site on IGL-MAC is subjected to reciprocal translocation with the FRT site on the modified human chromosome 14 in the presence of FLPo recombinase. When recombination takes place, 5'HPRT is ligated to 3'HPRT on IGHL-MAC, the HPRT gene is reconstructed, and HAT resistance is acquired. When CHO #14 IGL-MAC reaches confluency in a 10-cm cell culture dish, 18 µg of an FLP expression plasmid is added using Lipofectamine 2000 (Thermo Fisher Scientific) with reference to the manufacturer's instructions. The culture medium is exchanged with a fresh culture medium 6 hours after the addition, the cells are seeded in ten 10-cm cell culture dishes 24 hours later, and drug selection is then carried out using 1× HAT (Sigma) and 8 µg/ml blasticidin.

The resulting HAT resistant clones are subjected to the subsequent analysis.

[B.2] Selection of Drug Resistant Clones by PCR Analysis

In order to confirm that reciprocal translocation of interest occurs using the FRT/FLP system and that IGHK-MAC is constructed, DNAs are extracted from the drug resistant clones and used as templates for PCR analysis. The primers are shown below.

Primers for Confirmation of Site of Ligation by Reciprocal Translocation:
- TRANS L1 (described above)
- TRANS R1 (described above)
- CMVr-1 (described above)
- PGKr-2 (described above)
- KJneo (described above)
- PGKr-2 (described above)

PCR is carried out using the primers described above, LA taq (Takara), and buffers and dNTPs (dATP, dCTP, dGTP, and dTTP) included in the kit under the recommended conditions. Temperature and cycle conditions are as follows: after thermal denaturation at 98° C. for 1 minute, the cycle of 94° C. for 10 seconds, 60° C. for 30 seconds, and 72° C. for 3 minutes was conducted for 30 cycles.

The human chromosome 22 region is subjected to PCR analysis using the sequences shown below.
- 553P-F (described above)
- 553P-R (described above)
- PPM1F L (described above)
- PPM1F R (described above)
- IGLVI-70 L (described above)
- IGLVI-70 R (described above)

GNAZ L (described above)
GNAZ R (described above)
LIF L (described above)
LIF R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute was conducted for 35 cycles.

Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 60° C. for 30 seconds or 56° C. for 30 seconds, and 72° C. for 1 minute was conducted for 35 cycles.

[B.3] Two-Color FISH Analysis

Two-color FISH analysis is carried out using, as probes, a combination of BAC clone CH17-95F2 (IGL region) and BAC clone CH17-262H11 (IGH region) and a combination of BAC clone CH17-424L4 (IGL region) and BAC clone CH17-212P11 (IGH region), thereby analyzing in detail whether or not IGHL-MAC had been actually constructed. Clones, in which signals indicating the IGL region and the IGH region had been observed on MAC, are positive clones, construction of IGHL-MAC is verified (designated as "CHO IGHL-MAC"), and the selected clones are subjected to the subsequent experiment.

Example 11

Transfer of IGHL-MAC into CHO K1 Cell Line

Both of IGHL-MAC and a by-product formed upon reciprocal translocation to construct the IGHL-MAC comprise a Neo resistant gene incorporated therein. When IGHL-MAC and the by-product are transferred into the target cell by microcell fusion, accordingly, a cell into which IGHL-MAC and/or the by-product have/has been transferred can be obtained by drug selection with G418. Because MAC comprises EGFP incorporated therein, whether or not IGHL-MAC has been transferred into a target cell can be determined. In order to prepare a donor cell capable of efficient chromosome transfer and carrying only IGHL-MAC, the IGHL-MAC is transferred into the CHO K1 cell line.

[A] Microcell Fusion and Isolation of Drug Resistant Clone

A cell line carrying only IGHL-MAC was prepared by chromosome transfer.

[A.1] Transfer of IGHL-MAC into CHO K1 Cell Line

The donor cell (CHO IGHL-MAC) is cultured in a cell culture dish, the culture medium is exchanged with an F12 medium supplemented with 20% FBS and 0.1 μg/ml colcemid when the cells reach confluency, the culture medium is further exchanged with a fresh F12 medium supplemented with 20% FBS and 0.1 μg/ml colcemid 48 hours after the initiation of culture, and the culture is incubated overnight to form microcells. The culture medium is removed, the centrifuge flask is filled with a cytochalasin B (10 μg/ml, Sigma) solution kept warm at 37° C. in advance, and centrifugation is then carried out at 34° C. and 8,000 rpm for 1 hour. Microcells are suspended in the serum-free DMEM medium and purified through 8-μm, 5-μm, and 3-μm filters. Thereafter, the microcells are suspended in 2 ml of a solution of 0.05 mg/ml PHA-P (Sigma) in DMEM, the culture medium is removed from the cell suspension, and the resultant is then added to the recipient CHO K1 cell line that reaches confluency in a 6-cm cell culture dish. After incubation is carried out for 15 minutes, the microcells are allowed to adhere to the CHO cells. Thereafter, cell fusion is carried out exactly for 1 minute using 1 ml of a PEG1000 (Wako) solution (prepared by completely dissolving 5 g of PEG1000 in 6 ml of the serum-free DMEM medium and adding 1 ml of dimethyl sulfoxide thereto, followed by sterilization by filtration). The cells are washed 4 times with 5 ml of serum-free DMEM to remove PEG, and the CHO culture solution is then added. The cells are seeded in ten 10-cm cell culture dishes 24 hours later, 800 μg/ml G418 is added thereto, and selection culture is then conducted for 10 days. The drug resistant cells obtained are subjected to the subsequent analysis.

[A.2] Selection of Drug Resistant Clones by PCR Analysis

In order to confirm that IGHL-MAC are transferred into the CHO K1 cell line, DNAs are extracted from the drug resistant clones and used as templates to perform PCR analysis. The primers are shown below.

Primers for Confirmation of Site of Ligation By Reciprocal Translocation:
TRANS L1 (described above)
TRANS R1 (described above)
CMVr-1 (described above)
PGKr-2 (described above)
KJneo (described above)
PGKr-2 (described above)

PCR is carried out using the primers described above, LA taq (Takara), and buffers and dNTPs (dATP, dCTP, dGTP, and dTTP) included in the kit under the recommended conditions. Temperature and cycle conditions are as follows: after thermal denaturation at 98° C. for 1 minute, the cycle of 94° C. for 10 seconds, 60° C. for 30 seconds, and 72° C. for 3 minutes was conducted for 30 cycles.

The human chromosome 22 region is subjected to PCR analysis using the sequences shown below.
- 553P-F (described above)
- 553P-R (described above)
- PPM1F L (described above)
- PPM1F R (described above)
- IGLVI-70 L (described above)
- IGLVI-70 R (described above)
- hVpreB1-F (described above)
- hVpreB1-Rm (described above)
- hVpreB3-F (described above)
- hVpreB3-R (described above)
- hL5-F (described above)
- hL5-R (described above)
- 344-F (described above)
- 344-R (described above)
- 350P-F (described above)
- 350P-R (described above)
- IgL-F (described above)
- IgL-Rm (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute was conducted for 35 cycles.

Primers for Confirmation of Human Chromosome 14 Region:
- MTA1-F3 (described above)
- MTA1-R3 (described above)
- ELK2P2-F (described above)
- ELK2P2-R (described above)
- g1(g2)-F (described above)
- g1(g2)-R (described above)
- VH3-F (described above)
- VH3-R (described above)
- CH3F3 (described above)
- CH4R2 (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 60° C. for 30 seconds or 56° C. for 30 seconds, and 72° C. for 1 minute is conducted for 35 cycles. The PCR-positive cell lines are subjected to the subsequent analysis.

[A.3] Two-Color FISH Analysis

FISH analysis is performed using Human cot-1 DNA and Mouse cot-1 DNA as probes to confirm that a copy of IGHL-MAC is independently retained. In addition, two-color FISH analysis is performed using, as probes, a combination of BAC clone CH17-95F2 (IGL region) and BAC clone CH17-262H11 (IGH region) and a combination of BAC clone CH17-424L4 (IGL region) and BAC clone CH17-212P11 (IGH region), thereby analyzing the IGHL-MAC structure in detail. Clones, in which signals indicating the IGL region and the IGH region are observed on MAC, are positive clones (designated as "CHO K1 IGHL-MAC") and are subjected to the subsequent experiment.

Example 12

Transfer of IGHL-MAC into Mouse ES Cells and Rat ES Cells

[A] Transfer of IGHL-MAC into Mouse ES Cells

In order to produce a human antibody-producing mouse, it is needed: to transfer IGHL-MAC into mouse ES cells; to inject the resultant cells into an 8-cell-stage fertilized egg; to prepare chimeric mice; and to allow IGHL-MAC to transmit to offsprings.

[A.1] Microcell Fusion and Isolation of Drug Resistant Clone

As donor cells, CHO K1 IGHL-MAC is used. Microcell fusion is carried out in the same manner as in Example 6 [A.1] to obtain EGFP-positive and drug-resistant clones, and the clones of interest are subjected to the subsequent analysis.

[A.2] Selection of Drug Resistant Clones by PCR Analysis

In order to confirm that IGHL-MAC is transferred into the mouse ES cell line, DNAs are extracted from the drug resistant clones and used as templates for PCR analysis. The primers used are shown below.

Primers for Confirmation of Site of Ligation by Reciprocal Translocation:
- TRANS L1 (described above)
- TRANS R1 (described above)
- CMVr-1 (described above)
- PGKr-2 (described above)
- KJneo (described above)
- PGKr-2 (described above)

PCR is carried out using the primers described above, LA taq (Takara), and buffers and dNTPs (dATP, dCTP, dGTP, and dTTP) included in the kit under the recommended conditions. Temperature and cycle conditions are as follows: after thermal denaturation at 98° C. for 1 minute, the cycle of 94° C. for 10 seconds, 60° C. for 30 seconds, and 72° C. for 3 minutes is conducted for 30 cycles.

The human chromosome 22 region is subjected to PCR analysis using the sequences shown below.
- 553P-F (described above)
- 553P-R (described above)
- PPM1F L (described above)
- PPM1F R (described above)
- IGLVI-70 L (described above)
- IGLVI-70 R (described above)
- hVpreB1-F (described above)
- hVpreB1-Rm (described above)
- hVpreB3-F (described above)
- hVpreB3-R (described above)
- hL5-F (described above)
- hL5-R (described above)
- 344-F (described above)
- 344-R (described above)
- 350P-F (described above)
- 350P-R (described above)
- IgL-F (described above)
- IgL-Rm (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minute, the cycle of 95° C. for 30 seconds, 63° C., 62° C., 60° C., 56° C., 55° C., or 50° C. for 30 seconds, and 72° C. for 1 minute is conducted for 35 cycles.

Primers for Confirmation of Human Chromosome 14 Region:
    MTA1-F3 (described above)
    MTA1-R3 (described above)
    ELK2P2-F (described above)
    ELK2P2-R (described above)
    g1(g2)-F (described above)
    g1(g2)-R (described above)
    VH3-F (described above)
    VH3-R (described above)
    CH3F3 (described above)
    CH4R2 (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 60° C. for 30 seconds or 56° C. for 30 seconds, and 72° C. for 1 minute is conducted for 35 cycles. The PCR-positive cell lines are subjected to the subsequent analysis.

[A.3] Two-Color FISH Analysis

FISH analysis is performed using Human cot-1 DNA and Mouse cot-1 DNA as probes to confirm that the clones carry only IGHL-MAC and maintain the mouse ES normal karyotype.

Two-color FISH analysis is carried out using, as probes, a combination of BAC clone CH17-95F2 (IGL region) and BAC clone CH17-262H11 (IGH region) and a combination of BAC clone CH17-424L4 (IGL region) and BAC clone CH17-212P11 (IGH region), thereby analyzing in detail whether or not IGHL-MAC has been actually constructed. The clone, in which signals indicating the IGL region and the IGH region are observed at expected positions on the MAC, is a positive cell line (HKD31 IGHL-MAC) and is subjected to injection.

[B] Transfer of IGHL-MAC into Rat ES Cells

In order to produce a human antibody-producing mouse, it is needed: to transfer IGHL-MAC into rat ES cells; to inject the resultant cells into an 8-cell-stage fertilized egg; to prepare chimeric mice; and to allow IGHL-MAC to transmit to offsprings.

[B.1] Microcell Fusion and Isolation of Drug Resistant Clone

In the same manner as with the technique of microcell fusion to mouse ES cells described in Example 6 [A.1], IGHL-MAC is introduced into rat ES cells. As donor cells, CHO K1 IGHL-MAC is used. Following fusion, incubation is carried out overnight, G418 is added to a concentration of 150 μg/ml, and selection culture is then carried out for 3 to 4 weeks. The resulting GFP-positive and drug-resistant clones are subjected to the subsequent analysis.

[B.2] Selection of Drug Resistant Clones by PCR Analysis

In order to confirm that IGHL-MAC is transferred into the rat ES cell line, DNAs are extracted from the drug resistant clones and are used as templates for PCR analysis. The primers are shown below.

Primers for Confirmation of Site of Ligation by Reciprocal Translocation:
    TRANS L1 (described above)
    TRANS R1 (described above)
    KJneo (described above)
    PGKr-2 (described above)

PCR is carried out using the primers described above, LA taq (Takara), and buffers and dNTPs (dATP, dCTP, dGTP, and dTTP) included in the kit under the recommended conditions. Temperature and cycle conditions are as follows: after thermal denaturation at 98° C. for 1 minute, the cycle of 94° C. for 10 seconds, 60° C. for 30 seconds, and 72° C. for 3 minutes is conducted for 30 cycles.

The human chromosome 22 region is subjected to PCR analysis using the sequences shown below.
    553P-F (described above)
    553P-R (described above)
    PPM1F L (described above)
    PPM1F R (described above)
    IGLVI-70 L (described above)
    IGLVI-70 R (described above)
    hVpreB1-F (described above)
    hVpreB1-Rm (described above)
    hVpreB3-F (described above)
    hVpreB3-R (described above)
    hL5-F (described above)
    hL5-R (described above)
    344-F (described above)
    344-R (described above)
    350P-F (described above)
    350P-R (described above)
    IgL-F (described above)
    IgL-Rm (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 63° C., 62° C., 60° C., 56° C., 55° C., or 50° C. for 30 seconds, and 72° C. for 1 minute is conducted for 35 cycles.

Primers for Confirmation of Human Chromosome 14 Region:
    MTA1-F3 (described above)
    MTA1-R3 (described above)
    ELK2P2-F (described above)
    ELK2P2-R (described above)
    g1(g2)-F (described above)
    g1(g2)-R (described above)
    VH3-F (described above)
    VH3-R (described above)
    CH3F3 (described above)
    CH4R2 (described above)

PCR is carried out using the primers described above, Ampli Taq Gold (Applied Biosystems) as Taq polymerase, and buffers and dNTPs (dATP, dCTP, dGTP, and dTTP) included in the kit under the recommended conditions. Temperature and cycle conditions are as follows: after thermal denaturation at 95° C. for 10 minutes, the cycle of 95° C. for 30 seconds, 60° C. for 30 seconds or 56° C. for 30 seconds, and 72° C. for 1 minute is conducted for 35 cycles. The PCR-positive cell lines are subjected to the subsequent analysis.

[B.3] Two-Color FISH Analysis

FISH analysis is performed using Human cot-1 DNA and Mouse cot-1 DNA as probes to confirm that the clones independently carry IGHL-MAC and maintain the rat ES normal karyotype (42 chromosomes). In addition, two-color FISH analysis is performed using, as probes, a combination of BAC clone CH17-95F2 (IGL region) and BAC clone CH17-262H11 (IGH region) and a combination of BAC clone CH17-424L4 (IGL region) and BAC clone CH17-212P11 (IGH region), thereby analyzing the IGHL-MAC structure in detail. The clone, in which signals indicating the IGL region and the IGH region have been observed at expected positions on the MAC, is a positive cell line (designated as "rESIGHL-MAC") and is subjected to injection.

Example 13

Production of IGHL-MAC-Carrying Mice and Rats and Production of Progeny-Transmitted Individuals Using IGHL-MAC-carrying mouse and rat ES cells, IGHL-MAC-carrying and progeny-transmitted mice and rats can be produced in the same manner as in Example 7. The progeny-transmitted mice and rats and chimeric mice obtained during the process are analyzed in the same manner as in Example 7 and Example 12 to confirm IGHL-MAC retention and antibody expression (including hλ). The resulting IGHL-MAC-carrying mouse and rat lineages are designated as mTC (IGHL-MAC) and rTC (IGHL-MAC), respectively.

Example 14

Production of Human Antibody-Producing Mouse

A mouse carrying IGHK-MAC and IGHL-MAC is subjected to crossbreeding with a mouse, in which the mouse Igh and Igk genes are destroyed and which has an Igl mutation (a mutation that lowers the Igl expression level), thereby to produce a human antibody-producing mouse.

[A] Production of Mouse Having Igh and Igk Gene Deletion (or Defect) and Expressing Igl at Low Level In order to produce a human antibody-producing mouse, a mouse deleting or expressing the mouse antibody genes at low level is produced.

[A.1] Production of Mouse Having Igh and Igk Gene Deletion (or Defect) and Expressing Igl at Low Level A mouse lineage generated from HKD31 mouse (in which mouse Igh and Igk genes have been destroyed) ES cells is subjected to crossbreeding with CD-1 having a mutation that lowers the mouse Igl expression level (ICR, purchased from Charles River) to produce a mouse having Igh and Igk gene deletion (or defect) and expressing Igl at low level.

A mouse Iglc mutation derived from CD-1 is analyzed by PCR-RFLP.

PCR was carried out using the primers shown below.

```
                                         (SEQ ID NO: 94)
mIglc1VnC L: 5'-CCTCAGGTTGGGCAGGAAGA-3'

(SEQ ID NO: 95)
J3C1: 5'-GACCTAGGAACAGTCAGCACGGG-3'
```

PCR was carried out using Ampli Taq Gold (Applied Biosystems) as Taq polymerase and buffers and dNTPs (dATP, dCTP, dGTP, and dTTP) included in the kit under the recommended conditions. Temperature and cycle conditions were as follows: after thermal denaturation at 95° C. for 10 minutes, the cycle of 95° C. for 30 seconds, 60° C. for 30 seconds, and 72° C. for 1 minute was conducted for 35 cycles.

PCR products were treated with KpnI-HF (NEB) and electrophoresed. Thereafter, PCR products in which no cleavage was observed were evaluated to carry mutant alleles. As a result, a mouse comprising Igλ mutation in both alleles was obtained (called "LD lineage").

[A.2] Evaluation of Mouse Antibody Gene Expression

Flow cytometry (FCM) and ELISA are carried out to evaluate that the expression of mouse antibody genes are lost or substantially lost.

When the Igh gene is destroyed and Iv expression is lost, as described in Example 7 [A.3], B cells are not produced. By determining the presence or absence of B cells, accordingly, Igh gene deletion (or defect) can be evaluated. FCM analysis was carried out as previously reported (Proc. Natl. Acad. Sci., U.S.A., 2000 Jan. 18; 97(2): 722-7), a mouse in which B cell depletion was observed was evaluated that the mouse Igh has been deleted (or deficient). The peripheral blood lymphocytes of the mouse that the mouse Igh and Igκ are considered to have been destroyed (called "HKD lineage") were subjected to FCM analysis, and the peripheral blood lymphocytes were found to be B220-negative, where the B220 is a B cell marker, and thus, in the mouse, the Igh gene has been destroyed. In addition, this mouse was further subjected to crossbreeding with a Igλ mutant mouse. As a result, a mouse in which the Igh and Igκ genes have been destroyed and which comprises Igλ mutation in both alleles was obtained (called "HKLD lineage").

The resulting mice were also subjected to ELISA to analyze expression of mouse Igk and Igl, in addition to expression of mouse Igh, in the same manner as previously reported (Proc. Natl. Acad. Sci., U.S.A., 2000 Jan. 18; 97(2): 722-7), and the lost expression and the low-level expression were observed in the mice.

[A.3] Production of Human Antibody-Producing Mouse

An IGHK-MAC-carrying mouse or an IGHL-MAC-carrying mouse is subjected to crossbreeding with a mouse having IghKO, IgkKO, and Igl mutation to produce a human antibody-producing mouse.

[B] Evaluation of Human Antibody-Producing Mouse

[B.1] FACS Analysis

Flow cytometry analysis is carried out in order to confirm the presence of B cells that carry IGHK-MAC or IGHL-MAC. Blood cells were stained using an antibody to mouse CD45R (B220) to confirm human IGM-, CD45R-, and GFP-positive cells. Blood was drawn from the eye socket using a heparin-coated capillary, and was then transferred to a heparin-PBS-containing tube, and the tube was subjected to inversion mixing, followed by ice cooling. After centrifuged at 2,000 rpm and 4° C. for 3 minutes, the supernatant was removed, various antibodies were added to react at 4° C. for 30 minutes, and the resultant was washed with PBS supplemented with 5% fetal bovine serum (5% FBS/PBS). After the final centrifugation, 1.2% dextran in physiological saline was added to the pellet and, after tapping, the resultant was allowed to stand at room temperature for 45 minutes to naturally precipitate red blood cells. The supernatant was transferred into a new tube, centrifugation was carried out at 2,000 rpm and 4° C. for 3 minutes, the supernatant was removed, a hemolytic agent (0.17 M $NH_4Cl$) was added to the pellet at room temperature, and the resultant was then allowed to stand for 5 minutes. After centrifuged at 2,000 rpm and 4° C. for 3 minutes, the pellet was washed with 5% FBS/PBS, and then suspended in 500 µl of 5% FBS/PBS. The resulting suspension was designated as an analyte sample and analyzed by flow cytometry. For HKD mTC (IGHK-MAC) mouse, flow cytometry analysis was conducted and, as a result, the presence of B220- and GFP-positive cells was confirmed in the peripheral blood lymphocytes, suggesting that human IGH, in particular IgM, has been expressed by function of at least IGHK-MAC.

[B.2] Analysis of Human Antibody Expression

ELISA assay is performed to confirm expression of the human antibody gene light chain, the human antibody gene heavy chain, and various isotypes. In the same manner as Example 7 [A.4], expression of mouse antibodies (mγ, mμ, mκ, and mλ) and human antibodies (hγ, hμ, hκ, hλ, hγ1, hγ2, hγ3, hγ4, hα, hε, and hδ) and concentrations of the antibodies in blood serum are determined, in addition to determining the presence or absence of mouse antibody expression.

[B.3] Expression Analysis and Sequence Identification of Human Antibody

The cDNA is synthesized from RNA obtained from the spleen of a human antibody-producing mouse, and the cloning and nucleotide sequencing of the human antibody gene variable regions were performed. Analysis and evaluation were performed in the same manner as in Example 7 [A.5].

[B.4] Evaluation of Response for Antigen-Specific Human Antibody Production

A human antibody-producing mouse is evaluated as to whether or not the response for production of antigen-specific human antibodies could be observed.

In accordance with the method described in Example 7 [A.6], the mouse is immunized with human serum albumin to analyze an increase in antibody titer.

[B.5] Obtaining Human Antibody-Producing Hybridoma from Human Antibody-Producing Mouse A human antibody-producing hybridoma can be obtained in the same manner as disclosed in the patent literature (WO 98/37757).

Example 15

Production of Human Antibody-Producing Rat

A rat carrying IGHK-MAC and IGHL-MAC is subjected to crossbreeding with a KO rat, which rat Igh, Igk, and Igl have been destroyed, to produce a human antibody-producing rat.

[A] Production and Evaluation of Human Antibody-Producing Rat

[A.1] Production of Human Antibody-Producing Rat

A rat lineage carrying IGHK-MAC or IGHL-MAC is subjected to crossbreeding with a rat lineage, in which rat Igh, Igκ, and Igλ genes have been destroyed, to produce human antibody-producing rats.

[A.2] FACS Analysis

Confirming B cells that carry IGHK-MAC or IGHL-MAC is conducted in the same manner as in Example 14 [B.1] using an anti-rat CD45R (B220) antibody and a hemolytic agent (0.17 M $NH_4Cl$).

[A.3] Analysis of Human Ig Expression

ELISA assay is performed in the same manner as Example 7 [A.4] to confirm expression of the human antibody gene light chain, the human antibody gene heavy chain, and various isotypes. Thus, human antibody production can be evaluated. Also, expression of rat antibodies (rγ, rμ, rκ, and rλ) is evaluated using anti-rat immunoglobulin antibodies.

[A.4] Analysis of Human Antibody Expression and Gene Sequence Identification

In the same manner as in Example 7 [A.5], sequencing, analysis, and evaluation of the antibody genes can be performed.

[A.5] Evaluation of Response for Production of Antigen-Specific Human Antibodies Evaluation can be performed in the same manner as in Example 14 [A.6].

[A.6] Obtaining Human Antibody-Producing Hybridoma from Human Antibody-Producing Rat A human antibody-producing hybridoma can be obtained in the same manner as Example 14 [B.5].

INDUSTRIAL APPLICABILITY

According to the present invention, human antibodies can be produced using a non-human animal, including a rodent such as rat. Thus, the present invention is useful for production of pharmaceutical antibodies.

All publications, patents, and patent applications cited herein are incorporated herein by reference in their entirety.

What is claimed is:

1. A mouse or rat selected from the group consisting of:
   (1) a mouse or rat capable of producing human antibodies, the genome of the mouse or rat comprising a mouse artificial chromosome vector comprising the human antibody heavy chain gene or gene locus derived from human chromosome 14 and the human antibody light chain κ gene or gene locus derived from human chromosome 2 (hIGHK-MAC),
   wherein the mouse artificial chromosome vector comprises, in the following order, telomere, the human antibody heavy chain gene or gene locus, the human antibody light chain κ gene or gene locus, and centromere, and
   wherein at least two endogenous antibody genes or gene loci of the mouse or rat are knocked out,
   wherein B cells of the mouse or rat produce human antibodies,
   wherein human antibodies are present in the peripheral blood of the mouse or rat; and
   (2) a mouse or rat capable of producing human antibodies, the genome of the mouse or rat comprising a mouse artificial chromosome vector comprising the human antibody heavy chain gene or gene locus derived from human chromosome 14 and the human antibody light chain 2 gene or gene locus derived from human chromosome 22 (hIGHL-MAC),
   wherein the mouse artificial chromosome vector(s) comprises, in the following order, telomere, the human antibody heavy chain gene or gene locus, the human antibody light chain λ gene or gene locus, and centromere, and
   wherein at least two endogenous antibody genes or gene loci of the rodent mouse or rat are knocked out,
   wherein B cells of the mouse or rat produce human antibodies,
   wherein human antibodies are present in the peripheral blood of the mouse or rat.

2. The mouse or rat of claim 1, wherein the mouse or rat is a mouse or rat capable of producing human antibodies, the genome of the mouse or rat comprising a mouse artificial chromosome vector comprising the human antibody heavy chain gene or gene locus derived from human chromosome 14 and the human antibody light chain κ gene or gene locus derived from human chromosome 2 (hIGHK-MAC),
   wherein the mouse artificial chromosome vector comprises, in the following order, telomere, the human antibody heavy chain gene or gene locus, the human antibody light chain κ gene or gene locus, and centromere, and
   wherein at least two endogenous antibody genes or gene loci of the mouse or rat are knocked out,
   wherein B cells of the mouse or rat produce human antibodies,
   wherein human antibodies are present in the peripheral blood of the mouse or rat.

3. The mouse or rat of claim 2, wherein the mouse or rat is a mouse.

4. The mouse or rat of claim 2, wherein the mouse or rat is a rat.

5. The mouse or rat of claim 1, wherein the mouse or rat is a mouse or rat capable of producing human antibodies, the genome of the mouse or rat comprising a mouse artificial chromosome vector comprising the human antibody heavy chain gene or gene locus derived from human chromosome 14 and the human antibody light chain λ gene or gene locus derived from human chromosome 22 (hIGHL-MAC),
   wherein the mouse artificial chromosome vector(s) comprises, in the following order, telomere, the human antibody heavy chain gene or gene locus, the human antibody light chain λ gene or gene locus, and centromere, and
   wherein at least two endogenous antibody genes or gene loci of the rodent mouse or rat are knocked out,
   wherein B cells of the mouse or rat produce human antibodies,
   wherein human antibodies are present in the peripheral blood of the mouse or rat.

6. The mouse or rat of claim 5, wherein the mouse or rat is a mouse.

7. The mouse or rat of claim 5, wherein the mouse or rat is a rat.

* * * * *

SEQUENCE LISTING

<160> NUMBER OF SEQ ID NOS: 95

<210> SEQ ID NO 1
<211> LENGTH: 36
<212> TYPE: DNA
<213> ORGANISM: Artificial
<220> FEATURE:
<223> OTHER INFORMATION: primer

<400> SEQUENCE: 1
tcgaggatcc cacatagaca ttcaaccgca aagcag         36

<210> SEQ ID NO 2
<211> LENGTH: 37
<212> TYPE: DNA
<213> ORGANISM: Artificial
<220> FEATURE:
<223> OTHER INFORMATION: primer

<400> SEQUENCE: 2
tcgaggatcc aggccctaca catcaaaaag tgaagca        37

```
<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
ctgagaagag tcattgttta tggtagact                                29

<210> SEQ ID NO 4
<211> LENGTH: 28
<212> TYPE: DNA
<213> ORGANISM: Artificial
<220> FEATURE:
<223> OTHER INFORMATION: primer

<400> SEQUENCE: 4
atccccatgt gtatcactgg caaactgt                                 28

<210> SEQ ID NO 5
<211> LENGTH: 28
<212> TYPE: DNA
<213> ORGANISM: Artificial
<220> FEATURE:
<223> OTHER INFORMATION: primer

<400> SEQUENCE: 5
ggggaataaa caccctttcc aaatcctc                                 28

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
accaagtaac cgatcaaacc aacccttg                                 28

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
agctcagaga cacctctcca                                          20

<210> SEQ ID NO 8
<211> LENGTH: 25
<212> TYPE: DNA
<213> ORGANISM: Artificial
<220> FEATURE:
<223> OTHER INFORMATION: primer

<400> SEQUENCE: 8
ctgtattagg atacttggct attga                                    25

<210> SEQ ID NO 9
<211> LENGTH: 25
<212> TYPE: DNA
<213> ORGANISM: Artificial
<220> FEATURE:
<223> OTHER INFORMATION: primer
```

<400> SEQUENCE: 9
tatcaagggg gtgtcggaaa tcgtg                                              25

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
actgggcctg ggagaacctg agact                                              25

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
aggtgctgct gggtggtcaa gt                                                 22

<210> SEQ ID NO 12
<211> LENGTH: 23
<212> TYPE: DNA
<213> ORGANISM: Artificial
<220> FEATURE:
<223> OTHER INFORMATION: primer

<400> SEQUENCE: 12
gctcctgcaa atgtctcctg tca                                                23

<210> SEQ ID NO 13
<211> LENGTH: 24
<212> TYPE: DNA
<213> ORGANISM: Artificial
<220> FEATURE:
<223> OTHER INFORMATION: primer

<400> SEQUENCE: 13
cttacccagg ctccaggctc tatt                                               24

<210> SEQ ID NO 14
<211> LENGTH: 25
<212> TYPE: DNA
<213> ORGANISM: Artificial
<220> FEATURE:
<223> OTHER INFORMATION: primer

<400> SEQUENCE: 14
ctctacctcc ctaccccatc atcac                                              25

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
tggaaggtgg ataacgccct                                                    20

<210> SEQ ID NO 16
<211> LENGTH: 22

```
<212> TYPE: DNA
<213> ORGANISM: Artificial
<220> FEATURE:
<223> OTHER INFORMATION: primer

<400> SEQUENCE: 16
tcattctcct ccaacattag ca                                            22

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
agtcagggca ttagcagtgc                                               20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gctgctgatg gtgagagtga                                               20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
ctctcctgca gggccagtca                                               20

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
tgctgatggt gagagtgaac tc                                            22

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
ctctaactga atcaagggaa tgaac                                         25

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
```
agcagtttga gtttaggatg aagg                                              24

<210> SEQ ID NO 23
<211> LENGTH: 43
<212> TYPE: DNA
<213> ORGANISM: Artificial
<220> FEATURE:
<223> OTHER INFORMATION: primer

<400> SEQUENCE: 23
tcgagcggcc gcaggatctt tgggggactg aatggggtgt gct                         43

<210> SEQ ID NO 24
<211> LENGTH: 40
<212> TYPE: DNA
<213> ORGANISM: Artificial
<220> FEATURE:
<223> OTHER INFORMATION: primer

<400> SEQUENCE: 24
tcgaacgcgt tggaaccctc atacgttgct ggtggaatgt                             40

<210> SEQ ID NO 25
<211> LENGTH: 45
<212> TYPE: DNA
<213> ORGANISM: Artificial
<220> FEATURE:
<223> OTHER INFORMATION: primer

<400> SEQUENCE: 25
cgaggatcca tttctccaca tcctagccaa cacttgacat ttcct                       45

<210> SEQ ID NO 26
<211> LENGTH: 41
<212> TYPE: DNA
<213> ORGANISM: Artificial
<220> FEATURE:
<223> OTHER INFORMATION: primer

<400> SEQUENCE: 26
tcgaggatcc gccagggaga cagatgccaa gtacggttta g                           41

<210> SEQ ID NO 27
<211> LENGTH: 28
<212> TYPE: DNA
<213> ORGANISM: Artificial
<220> FEATURE:
<223> OTHER INFORMATION: primer

<400> SEQUENCE: 27
tgagaacaca ggggtctcca ttctgact                                          28

<210> SEQ ID NO 28
<211> LENGTH: 28
<212> TYPE: DNA
<213> ORGANISM: Artificial
<220> FEATURE:
<223> OTHER INFORMATION: primer

<400> SEQUENCE: 28
acaatcaaca gcatcccat ctctgaag                                           28

<210> SEQ ID NO 29
<211> LENGTH: 28
<212> TYPE: DNA
<213> ORGANISM: Artificial

```
<220> FEATURE:
<223> OTHER INFORMATION: primer

<400> SEQUENCE: 29
gacgtgctac ttccatttgt cacgtcct                                          28

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30
tggtcactga agctttccat ctgctctt                                          28

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
tggaggccat aaacaagaag ac                                                22

<210> SEQ ID NO 32
<211> LENGTH: 21
<212> TYPE: DNA
<213> ORGANISM: Artificial
<220> FEATURE:
<223> OTHER INFORMATION: primer

<400> SEQUENCE: 32
ccccttgacc cagaaattcc a                                                 21

<210> SEQ ID NO 33
<211> LENGTH: 26
<212> TYPE: DNA
<213> ORGANISM: Artificial
<220> FEATURE:
<223> OTHER INFORMATION: primer

<400> SEQUENCE: 33
catcgccttc tatcgccttc ttgacg                                            26

<210> SEQ ID NO 34
<211> LENGTH: 28
<212> TYPE: DNA
<213> ORGANISM: Artificial
<220> FEATURE:
<223> OTHER INFORMATION: primer

<400> SEQUENCE: 34
atctgcacga gactagtgag acgtgcta                                          28

<210> SEQ ID NO 35
<211> LENGTH: 44
<212> TYPE: DNA
<213> ORGANISM: Artificial
<220> FEATURE:
<223> OTHER INFORMATION: primer

<400> SEQUENCE: 35
tcgagcggcc gcgtacaatc ttggatcact acaacctctg ccta                        44
```

```
<210> SEQ ID NO 36
<211> LENGTH: 46
<212> TYPE: DNA
<213> ORGANISM: Artificial
<220> FEATURE:
<223> OTHER INFORMATION: primer

<400> SEQUENCE: 36
tcgaggcgcg ccaggattat agatgtgagc catcactaag actcct                    46

<210> SEQ ID NO 37
<211> LENGTH: 40
<212> TYPE: DNA
<213> ORGANISM: Artificial
<220> FEATURE:
<223> OTHER INFORMATION: primer

<400> SEQUENCE: 37
tcgagtcgac agcacgttgg gaggccaagg caggagaata                            40

<210> SEQ ID NO 38
<211> LENGTH: 35
<212> TYPE: DNA
<213> ORGANISM: Artificial
<220> FEATURE:
<223> OTHER INFORMATION: primer

<400> SEQUENCE: 38
tcgaggatcc tggctgacac agccagtccc ggatt                                 35

<210> SEQ ID NO 39
<211> LENGTH: 28
<212> TYPE: DNA
<213> ORGANISM: Artificial
<220> FEATURE:
<223> OTHER INFORMATION: primer

<400> SEQUENCE: 39
agcaattagg gcctgtgcat ctcactttt                                         28

<210> SEQ ID NO 40
<211> LENGTH: 28
<212> TYPE: DNA
<213> ORGANISM: Artificial
<220> FEATURE:
<223> OTHER INFORMATION: primer

<400> SEQUENCE: 40
ccagctcatt cctcccactc atgatcta                                          28

<210> SEQ ID NO 41
<211> LENGTH: 28
<212> TYPE: DNA
<213> ORGANISM: Artificial
<220> FEATURE:
<223> OTHER INFORMATION: primer

<400> SEQUENCE: 41
catctggagt cctattgaca tcgccagt                                          28

<210> SEQ ID NO 42
<211> LENGTH: 28
<212> TYPE: DNA
<213> ORGANISM: Artificial
<220> FEATURE:
<223> OTHER INFORMATION: primer
```

```
<400> SEQUENCE: 42
cttattcctc cttctgccca cccttcat                                           28

<210> SEQ ID NO 43
<211> LENGTH: 24
<212> TYPE: DNA
<213> ORGANISM: Artificial
<220> FEATURE:
<223> OTHER INFORMATION: primer

<400> SEQUENCE: 43
agcactttac gcatcccagc atgt                                               24

<210> SEQ ID NO 44
<211> LENGTH: 24
<212> TYPE: DNA
<213> ORGANISM: Artificial
<220> FEATURE:
<223> OTHER INFORMATION: primer

<400> SEQUENCE: 44
ccaagagagt agtcgtgccc ctca                                               24

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
cccactttac cgtgctcatt                                                    20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
atgaaggtcc gtgactttgg                                                    20

<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47
accccaaagg ccaaactctc cactc                                              25

<210> SEQ ID NO 48
<211> LENGTH: 24
<212> TYPE: DNA
<213> ORGANISM: Artificial
<220> FEATURE:
<223> OTHER INFORMATION: primer

<400> SEQUENCE: 48
cacttgtact ccttgccatt cagc                                               24

<210> SEQ ID NO 49
```

```
<211> LENGTH: 20
<212> TYPE: DNA
<213> ORGANISM: Artificial
<220> FEATURE:
<223> OTHER INFORMATION: primer

<400> SEQUENCE: 49
agtgagataa gcagtggatg                                               20

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
cttgtgctac tcccatcact                                               20

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
aggccagcat ctgcgaggat                                               20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
gtggcagcaa gtagacatcg                                               20

<210> SEQ ID NO 53
<211> LENGTH: 28
<212> TYPE: DNA
<213> ORGANISM: Artificial
<220> FEATURE:
<223> OTHER INFORMATION: primer

<400> SEQUENCE: 53
cctattggcg ttactatggg aacatacg                                      28

<210> SEQ ID NO 54
<211> LENGTH: 29
<212> TYPE: DNA
<213> ORGANISM: Artificial
<220> FEATURE:
<223> OTHER INFORMATION: primer

<400> SEQUENCE: 54
tgtagctgac tttagccacc cacaagtac                                     29

<210> SEQ ID NO 55
<211> LENGTH: 44
<212> TYPE: DNA
<213> ORGANISM: Artificial
<220> FEATURE:
<223> OTHER INFORMATION: primer

<400> SEQUENCE: 55
```
tcgaggcgcg ccctcaaact cctgggtgta aatgatcctc ctgc    44

<210> SEQ ID NO 56
<211> LENGTH: 32
<212> TYPE: DNA
<213> ORGANISM: Artificial
<220> FEATURE:
<223> OTHER INFORMATION: primer

<400> SEQUENCE: 56
tgagggtacc gtgcagtaaa gtatgattga gc    32

<210> SEQ ID NO 57
<211> LENGTH: 40
<212> TYPE: DNA
<213> ORGANISM: Artificial
<220> FEATURE:
<223> OTHER INFORMATION: primer

<400> SEQUENCE: 57
tcgagtcgac cttgctgatt atacctcatc tccttccctc    40

<210> SEQ ID NO 58
<211> LENGTH: 28
<212> TYPE: DNA
<213> ORGANISM: Artificial
<220> FEATURE:
<223> OTHER INFORMATION: primer

<400> SEQUENCE: 58
cctgccttct tgtttcagct ctcaactg    28

<210> SEQ ID NO 59
<211> LENGTH: 28
<212> TYPE: DNA
<213> ORGANISM: Artificial
<220> FEATURE:
<223> OTHER INFORMATION: primer

<400> SEQUENCE: 59
gacgtgctac ttccatttgt cacgtcct    28

<210> SEQ ID NO 60
<211> LENGTH: 28
<212> TYPE: DNA
<213> ORGANISM: Artificial
<220> FEATURE:
<223> OTHER INFORMATION: primer

<400> SEQUENCE: 60
atccccatgt gtatcactgg caaactgt    28

<210> SEQ ID NO 61
<211> LENGTH: 28
<212> TYPE: DNA
<213> ORGANISM: Artificial
<220> FEATURE:
<223> OTHER INFORMATION: primer

<400> SEQUENCE: 61
acactttagt ccctgtcccc tcaacgag    28

<210> SEQ ID NO 62
<211> LENGTH: 25
<212> TYPE: DNA

```
<213> ORGANISM: Artificial
<220> FEATURE:
<223> OTHER INFORMATION: primer

<400> SEQUENCE: 62
agatctcttg agcccagcag tttga                                          25

<210> SEQ ID NO 63
<211> LENGTH: 24
<212> TYPE: DNA
<213> ORGANISM: Artificial
<220> FEATURE:
<223> OTHER INFORMATION: primer

<400> SEQUENCE: 63
tgaagttagc cggggataca gacg                                           24

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
aacggcagcc aaaccaaaga                                                20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
accaggactg gctgggcata                                                20

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
agtctgcgct gacccaggaa                                                20

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
ttgagccaga gaagcggtca                                                20

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
tccacttggg ggtctgcatt                                                20
```

<210> SEQ ID NO 69
<211> LENGTH: 20
<212> TYPE: DNA
<213> ORGANISM: Artificial
<220> FEATURE:
<223> OTHER INFORMATION: primer

<400> SEQUENCE: 69
tggtgctgag cagctgtgtg                                               20

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
tgggacttag gtgggccaga                                               20

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
gcctccccaa gagcctgaat                                               20

<210> SEQ ID NO 72
<211> LENGTH: 25
<212> TYPE: DNA
<213> ORGANISM: Artificial
<220> FEATURE:
<223> OTHER INFORMATION: primer

<400> SEQUENCE: 72
tgtcctgggc tcctgtcctg ctcat                                         25

<210> SEQ ID NO 73
<211> LENGTH: 20
<212> TYPE: DNA
<213> ORGANISM: Artificial
<220> FEATURE:
<223> OTHER INFORMATION: primer

<400> SEQUENCE: 73
ggcggcgact ccaccctctt                                               20

<210> SEQ ID NO 74
<211> LENGTH: 22
<212> TYPE: DNA
<213> ORGANISM: Artificial
<220> FEATURE:
<223> OTHER INFORMATION: primer

<400> SEQUENCE: 74
cactgcctgc ccgctgctgg ta                                            22

<210> SEQ ID NO 75
<211> LENGTH: 21
<212> TYPE: DNA
<213> ORGANISM: Artificial
<220> FEATURE:

<223> OTHER INFORMATION: primer

<400> SEQUENCE: 75
gggcggggaa gtgggggaga g                                             21

<210> SEQ ID NO 76
<211> LENGTH: 25
<212> TYPE: DNA
<213> ORGANISM: Artificial
<220> FEATURE:
<223> OTHER INFORMATION: primer

<400> SEQUENCE: 76
agccccaaga acccagccga tgtga                                         25

<210> SEQ ID NO 77
<211> LENGTH: 25
<212> TYPE: DNA
<213> ORGANISM: Artificial
<220> FEATURE:
<223> OTHER INFORMATION: primer

<400> SEQUENCE: 77
ggcagaggga gtgtggggtg ttgtg                                         25

<210> SEQ ID NO 78
<211> LENGTH: 20
<212> TYPE: DNA
<213> ORGANISM: Artificial
<220> FEATURE:
<223> OTHER INFORMATION: primer

<400> SEQUENCE: 78
atcatctgct cgctctctcc                                               20

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
cacatctgta gtggctgtgg                                               20

<210> SEQ ID NO 80
<211> LENGTH: 20
<212> TYPE: DNA
<213> ORGANISM: Artificial
<220> FEATURE:
<223> OTHER INFORMATION: primer

<400> SEQUENCE: 80
accagcgcgt catcatcaag                                               20

<210> SEQ ID NO 81
<211> LENGTH: 20
<212> TYPE: DNA
<213> ORGANISM: Artificial
<220> FEATURE:
<223> OTHER INFORMATION: primer

<400> SEQUENCE: 81
atcgccagcc tcaccatttc                                               20

-continued

```
<210> SEQ ID NO 82
<211> LENGTH: 22
<212> TYPE: DNA
<213> ORGANISM: Artificial
<220> FEATURE:
<223> OTHER INFORMATION: primer

<400> SEQUENCE: 82
ggagaccacc aaaccctcca aa                                              22

<210> SEQ ID NO 83
<211> LENGTH: 22
<212> TYPE: DNA
<213> ORGANISM: Artificial
<220> FEATURE:
<223> OTHER INFORMATION: primer

<400> SEQUENCE: 83
gagagttgga gaagggtga ct                                               22

<210> SEQ ID NO 84
<211> LENGTH: 20
<212> TYPE: DNA
<213> ORGANISM: Artificial
<220> FEATURE:
<223> OTHER INFORMATION: primer

<400> SEQUENCE: 84
acctagaggg tctcacctcc                                                 20

<210> SEQ ID NO 85
<211> LENGTH: 19
<212> TYPE: DNA
<213> ORGANISM: Artificial
<220> FEATURE:
<223> OTHER INFORMATION: primer

<400> SEQUENCE: 85
ccctggacat caagaatgg                                                  19

<210> SEQ ID NO 86
<211> LENGTH: 44
<212> TYPE: DNA
<213> ORGANISM: Artificial
<220> FEATURE:
<223> OTHER INFORMATION: primer

<400> SEQUENCE: 86
tcgaggatcc ggcctcccaa aggattatag acgtgagcca ctgt                      44

<210> SEQ ID NO 87
<211> LENGTH: 42
<212> TYPE: DNA
<213> ORGANISM: Artificial
<220> FEATURE:
<223> OTHER INFORMATION: primer

<400> SEQUENCE: 87
tcgaggcgcg ccggcacctc tcctattttc ttcacagcac tt                        42

<210> SEQ ID NO 88
<211> LENGTH: 44
<212> TYPE: DNA
<213> ORGANISM: Artificial
<220> FEATURE:
<223> OTHER INFORMATION: primer
```

```
<400> SEQUENCE: 88
tcgaggcgcg ccagcatggt ggcccgcacg tatagtcgca gcta                    44

<210> SEQ ID NO 89
<211> LENGTH: 47
<212> TYPE: DNA
<213> ORGANISM: Artificial
<220> FEATURE:
<223> OTHER INFORMATION: primer

<400> SEQUENCE: 89
tcgagcggcc gcaaagaagg ggcccgcctc tgcctctaaa tcctgac                 47

<210> SEQ ID NO 90
<211> LENGTH: 28
<212> TYPE: DNA
<213> ORGANISM: Artificial
<220> FEATURE:
<223> OTHER INFORMATION: primer

<400> SEQUENCE: 90
tgcaggtatc tgttggtgtc cctgtttt                                      28

<210> SEQ ID NO 91
<211> LENGTH: 28
<212> TYPE: DNA
<213> ORGANISM: Artificial
<220> FEATURE:
<223> OTHER INFORMATION: primer

<400> SEQUENCE: 91
gacgtgctac ttccatttgt cacgtcct                                      28

<210> SEQ ID NO 92
<211> LENGTH: 28
<212> TYPE: DNA
<213> ORGANISM: Artificial
<220> FEATURE:
<223> OTHER INFORMATION: primer

<400> SEQUENCE: 92
agcagagctc gtttagtgaa ccgtcaga                                      28

<210> SEQ ID NO 93
<211> LENGTH: 28
<212> TYPE: DNA
<213> ORGANISM: Artificial
<220> FEATURE:
<223> OTHER INFORMATION: primer

<400> SEQUENCE: 93
ctgtcctatc cttgcagctg tcttccag                                      28

<210> SEQ ID NO 94
<211> LENGTH: 20
<212> TYPE: DNA
<213> ORGANISM: Artificial
<220> FEATURE:
<223> OTHER INFORMATION: primer

<400> SEQUENCE: 94
cctcaggttg ggcaggaaga                                               20

<210> SEQ ID NO 95
<211> LENGTH: 23
```

```
<212> TYPE: DNA
<213> ORGANISM: Artificial
<220> FEATURE:
<223> OTHER INFORMATION: primer

<400> SEQUENCE: 95
gacctaggaa cagtcagcac ggg                                              23
```